(12) United States Patent
Hughes et al.

(10) Patent No.: US 8,293,903 B2
(45) Date of Patent: Oct. 23, 2012

(54) 3-AMINOCYCLOPENTANECARBOXAMIDES AS CHEMOKINE RECEPTOR AGONISTS

(75) Inventors: Robert O. Hughes, Eureka, MO (US); Rajesh V. Devraj, Chesterfield, MO (US); Donald J. Rogier, Chesterfield, MO (US); John I. Trujillo, St. Charles, MO (US); Steve R. Turner, Chesterfield, MO (US); Wei Huang, Wildwood, MO (US)

(73) Assignee: Pfizer Inc., New York, NY (US)

( * ) Notice: Subject to any disclaimer, the term of this patent is extended or adjusted under 35 U.S.C. 154(b) by 313 days.

(21) Appl. No.: 12/795,266

(22) Filed: Jun. 7, 2010

(65) Prior Publication Data

US 2011/0144129 A1    Jun. 16, 2011

Related U.S. Application Data

(63) Continuation of application No. PCT/IB2009/055232, filed on Nov. 20, 2009.

(60) Provisional application No. 61/118,053, filed on Nov. 26, 2008.

(51) Int. Cl.
*C07D 403/04* (2006.01)
*C07D 403/14* (2006.01)
*C07D 487/08* (2006.01)
*A61K 31/506* (2006.01)
*A61P 25/02* (2006.01)

(52) U.S. Cl. ........................................ 544/295; 514/248
(58) Field of Classification Search .................. 544/295; 514/248
See application file for complete search history.

(56) References Cited

U.S. PATENT DOCUMENTS

| | | | |
|---|---|---|---|
| 7,449,467 B2 | 11/2008 | Xue et al. | 514/253.01 |
| 7,576,089 B2 | 8/2009 | Xue et al. | 514/256 |
| 7,618,970 B2 | 11/2009 | Xue et al. | 514/253.01 |
| 7,700,624 B2 | 4/2010 | Xue | 514/318 |
| 2005/0101628 A1 | 5/2005 | Jiao et al. | 514/300 |
| 2005/0234034 A1 | 10/2005 | Pennell et al. | 514/210.16 |
| 2006/0020133 A1 | 1/2006 | Xue et al. | 544/295 |

FOREIGN PATENT DOCUMENTS

WO   WO 2005105092   11/2005
WO   WO 2007072201   6/2007

OTHER PUBLICATIONS

Pasternak et al., Bioorganic & Medicinal Chemistry Letters, 18, 2008, pp. 994-998.
Kothandaraman et al., Bioorganic & Medicinal Chemistry Letters, 19, 2009, pp. 1830-1834.

*Primary Examiner* — Venkataraman Balasubramanian

(57) ABSTRACT

There is provided a compound of Formula I(a) or I(b)

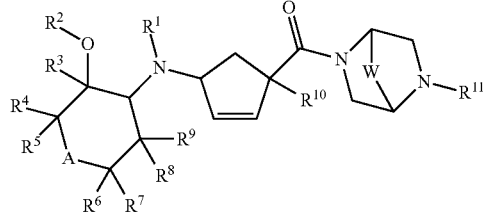

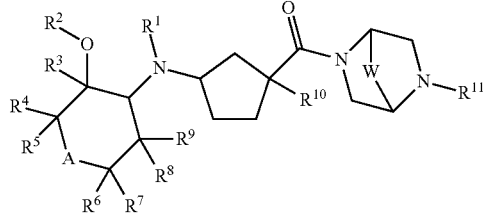

or a pharmaceutically acceptable salt thereof, wherein the various substituents are defined herein.

4 Claims, No Drawings

3-AMINOCYCLOPENTANECARBOXAMIDES AS CHEMOKINE RECEPTOR AGONISTS

This application is a continuation of International Patent Application Number PCT/IB09/055232 which was filed Nov. 20, 2009, which claims the benefit of U.S. Provisional Patent Application No. 61/118,053 filed Nov. 26, 2008.

FIELD OF THE INVENTION

The present invention relates to compounds that modulate the activity of chemokine receptors, such as CCR2 and CCR5. The compounds can be used, for example, to treat diseases associated with chemokine receptor expression or activity.

BACKGROUND OF THE INVENTION

The migration and transport of leukocytes from blood vessels into diseased tissues is involved in the initiation of normal disease-fighting inflammatory responses. The process, also known as leukocyte recruitment, is also related to the onset and progression of inflammatory and autoimmune diseases. The resulting pathology of these diseases derives from the attack of the body's immune system defenses on normal tissues. Accordingly, preventing and blocking leukocyte recruitment to target tissues in inflammatory, autoimmune disease and cancer would be an effective approach to therapeutic intervention.

The infiltration of monocytes/macrophages into sites of inflammation is related to proteins, such as monocyte chemoattractant protein-1 (MCP-1, CCL2). Macrophages produce chemokines, such as macrophage inflammatory protein-1-beta (MIP-1β, CCL4). Such proteins interacts with chemokine receptors, for example, CCR2 and CCR5. Modulation, such as antagonism or inhibition, of CCR2 or CCR5 would be helpful to treat a wide range of diseases.

The identification of compounds that modulate the activity of chemokine receptors represents a desirable drug design approach to develop pharmacological agents for the treatment of diseases associated with chemokine receptor activity. The compounds of the present invention help fulfill these and other needs.

SUMMARY OF THE INVENTION

In an embodiment of the present invention, there is provided a compound of Formula I(a) or I(b):

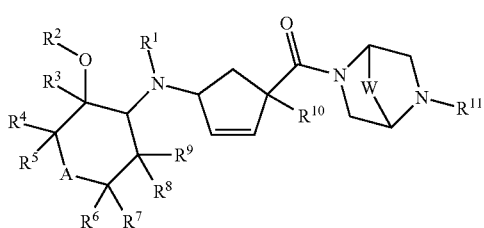

I(a)

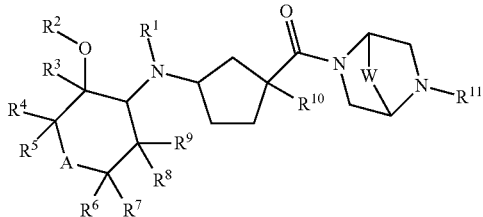

I(b)

or a pharmaceutically acceptable salt thereof, wherein:
A is O or $CF_2$;
W is $CR^{13}R^{14}$, C(O), $CHOR^{15}$, CHF, $CF_2$, O or S
$R^1$ is H or $C_{1-6}$ alkyl optionally substituted by 1-3 substituents selected from halo, OH, $CO_2H$, $CO_2$—($C_{1-6}$ alkyl), or $C_{1-3}$ alkoxy;
$R^2$ and $R^3$ are each, independently, H, $(C_1$-$C_6)$alkyl, $(C_1$-$C_6)$haloalkyl, halo, $(C_3$-$C_6)$cycloalkyl, CN, OH, $CO_2R$, $OCOR^{12}$; wherein said $(C_1$-$C_6)$alkyl is optionally substituted with one or more substituents selected from F, $(C_1$-$C_3)$ alkoxy, OH, CN or $CO_2R^{12}$;
$R^5$ and $R^9$ are each, independently, H, $(C_1$-$C_6)$alkyl, $(C_1$-$C_6)$haloalkyl, $(C_3$-$C_6)$cycloalkyl, $(C_3$-$C_6)$cycloalkyloxy, CN, OH, $CO_2R$, $OCOR^{12}$; wherein said $(C_1$-$C_6)$alkyl is optionally substituted with one or more substituents selected from F, $(C_1$-$C_3)$alkoxy, OH, CN or $CO_2R^{12}$;
$R^2$ and $R^9$, taken together may form a 5-8 membered ring;
$R^4$ and $R^7$, taken together may form a 5-8 membered ring.
$R^4$ and $R^5$ are each, independently, H, CN, $(C_1$-$C_6)$alkyl, halo, $(C_1$-$C_3)$ alkoxy, $(C_1$-$C_3)$haloalkoxy, $(C_3$-$C_6)$cycloalkyl, OH, $CO_2R^{12}$, $OCOR^{12}$, wherein said $(C_1$-$C_6)$alkyl is optionally substituted with one or more substituents selected from F, $(C_1$-$C_3)$ alkoxy, OH or $CO_2R^{12}$;
$R^6$ and $R^7$ are each, independently, H, CN, $(C_1$-$C_6)$alkyl, halo, $(C_1$-$C_3)$alkoxy, $(C_1$-$C_3)$haloalkoxy, $(C_3$-$C_6)$cycloalkyl, OH, $CO_2R^{12}$, $OCOR^{12}$, wherein said $(C_1$-$C_6)$alkyl is optionally substituted with one or more substituents selected from F, $(C_1$-$C_3)$alkoxy, OH or $CO_2R^{12}$;
or $R^2$ and $R^3$ together with the carbon atom to which they are attached form a 3-7 membered spirocyclyl group;
or $R^4$ and $R^5$ together with the carbon atom to which they are attached form a 4-7 membered spirocyclyl group;
or $R^3$ and $R^4$ together with the C atoms to which they are attached form a fused 3-7 membered cycloalkyl group or 3-7 membered heterocycloalkyl group;
$R^{10}$ is $(C_1$-$C_6)$alkyl, $(C_1$-$C_6)$haloalkyl, $(C_1$-$C_6)$hydroxyalkyl, $(C_1$-$C_6)$alkoxy, $(C_3$-$C_6)$cycloalkyl, hydroxy$(C_3$-$C_6)$cycloalkyl, $(C_1$-$C_6)$alkoxy cycloalkyl, OH, $(C_1$-$C_5)$heterocyclyl, amino, aryl or CN,
$R^{11}$ is aryl or heteroaryl, said $R^{11}$ optionally, independently substituted by one or more $(C_1$-$C_6)$ alkyl, halo, $(C_1$-$C_6)$haloalky $(C_1$-$C_6)$alkoxy, OH, amino, $C(O)NH_2$, $NH_2SO_2$, $SF_5$, or CN;
$R^{12}$ is H, $(C_1$-$C_4)$alkyl, or $(C_3$-$C_6)$cycloalkyl;
$R^{13}$ is H, halo, $(C_1$-$C_4)$alkyl, $(C_1$-$C_4)$alkoxy, or OH;
$R^{14}$ is H, halo, $(C_1$-$C_4)$alkyl, $(C_1$-$C_4)$alkoxy or OH; and
$R^{15}$ is H, $(C_1$-$C_6)$alkyl or $(C_3$-$C_6)$cycloalkyl.

DETAILED DESCRIPTION OF THE INVENTION

These inventions are not limited to the embodiments described in this specification, and may be modified.

A. Definitions

For the following defined terms, these definitions shall be applied, unless a different definition is given in the claims or elsewhere in this specification.

The term aryl groups is intended to include aromatic carbocyclic groups such as phenyl, biphenylyl, indenyl, naphthyl as well as aromatic carbocycles fused to a heterocycle such as benzothienyl, benzofuranyl, indolyl, quinolinyl, benzothiazole, benzooxazole, benzimidazole, isoquinolinyl, isoindolyl, benzotriazole, indazole, and acridinyl.

The term heteroaryl includes mono- and poly-cyclic aromatic rings containing from 3 to 20, or from 4 to 10 ring atoms, at least one of which is a heteroatom such as oxygen, sulphur, phosphorus or nitrogen. Examples of such groups include furyl, thienyl, pyrrolyl, imidazolyl, triazolyl, thiazolyl, tetrazolyl, oxazolyl, isoxazolyl, pyrazolyl, pyridyl, pyrimidinyl, pyrazinyl, pyridazinyl, triazinyl, quinolinyl, isoquinolinyl, quinoxalinyl, benzothiazole, benzoxazolyl, benzothienyl or benzofuryl.

The term "cycloalkyl," refer to cyclized hydrocarbons (mono and polycyclic) such as cyclized alkyl, alkenyl, or alkynyl groups. In some embodiments, the cycloalkyl group is $C_{3-14}$, $C_{3-10}$, $C_{3-8}$, $C_{3-7}$, $C_{3-6}$, or $C_{3-5}$. In some embodiments, cycloalkyl moieties each have from 3 to 14, from 3 to 10, or from 3 to 6 ring-forming carbon atoms. In some embodiments, the cycloalkyl group has 0, 1 or 2 double or triple bonds. Examples of cycloalkyl groups include cyclopropyl, cyclobutyl, cyclopentyl, cyclohexyl, cycloheptyl, cyclopentenyl, etc. In the present application, cycloalkyl is also intended to include bridged cyclic hydrocarbons such as adamantyl groups and the like.

Heterocycles are carbocyclic rings (mono or polycyclic) which include one or more heteroatoms such as nitrogen, oxygen or sulfur in the ring. In some embodiments, the heterocycle contains 3 to 8 ring members. In some embodiments, the heterocycle contains 3 to 6 ring members. In some embodiments, the heterocycle contains 1, 2 or 3 heteroatoms. Heterocycles can be saturated or unsaturated. In some embodiments, heterocycles contain 0, 1 or 2 double bonds or triple bonds. Ring-forming carbon atoms and heteroatoms can also bear oxo or sulfide substituents (such as, CO, CS, SO, $SO_2$, NO, and the like). Examples of heterocycles include tetrahydrofuranyl, tetrahydrothiophenyl, morpholino, thiomorpholino, azetidinyl, pyrrolidinyl, piperazinyl, piperidinyl, pyrane, dioxane, and thiazolidinyl.

Monosubstituted aryl refers to an aryl group having one substituent. Polysubstituted aryl refers to aryl having 2 or more substituents (such as 2-4 substituents). Monosubstituted heteroaryl refers to a heteroaryl group having one substituent. Polysubstituted heteroaryl refers to heteroaryl having 2 or more substituents (such as 2-4 substituents). Monosubstituted cycloalkyl (or carbocycle) refers to a cycloalkyl group having one substituent. Polysubstituted cycloalkyl (or carbocycle) refers to cycloalkyl having 2 or more substituents (such as 2-4 substituents). Monosubstituted heterocycle refers to a heterocycle having one substituent. Polysubstituted heterocycle refers to heterocycle having 2 or more substituents (such as 2-4 substituents).

The term halo, by itself or as part of another substituent, means, unless otherwise stated, a fluorine, chlorine, bromine, or iodine. Similarly, terms such as haloalkyl, are meant to include monohaloalkyl and polyhaloalkyl. For example, the term haloalkyl, such as halo($C_1$-$C_4$)alkyl, is meant to include trifluoromethyl, 2,2,2-trifluoroethyl, 4-chlorobutyl, 3-bromopropyl, and the like.

The term alkyl when used either alone or as a suffix includes straight chain and branched structures such as primary alkyl groups, secondary alkyl groups and tertiary alkyl groups. These groups may contain up to 15, or up to 8, or up to 4 carbon atoms. In some embodiments, the alkyl group is $C_{1-10}$, $C_{1-5}$, $C_{1-6}$, $C_{1-5}$, $C_{1-4}$, or $C_{1-3}$. Examples of alkyl radicals include groups such as methyl, ethyl, n-propyl, isopropyl, n-butyl, t-butyl, isobutyl, and sec-butyl. Similarly the terms alkenyl and alkynyl refer to unsaturated straight or branched structures containing for example from 2 to 12, or from 2 to 6 carbon atoms. In some embodiments, the alkenyl or alkynyl group is $C_{2-10}$, $C_{2-8}$, $C_{2-6}$, $C_{2-5}$, $C_{2-4}$, or $C_{2-3}$. Examples of alkenyl and alkynyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "carrier" describes an ingredient other than a compound. Carriers may be pharmaceutically acceptable material or vehicle. Examples include liquid or solid filler, diluent, excipient, solvent or encapsulating material.

The phrase "contacting a chemokine receptor" means in vivo, ex vivo, or in vitro contact is made with a chemokine receptor and includes administration of a compound or salt of the present invention to a subject having a chemokine receptor, as well as, for example, introducing a compound or salt of the invention into a sample containing a cellular, unpurified, or purified preparation containing a chemokine receptor. For example, contacting includes interactions between the compound and the receptor, such as binding.

The term "subject" refers to any animal, including mammals, such as mice, rats, other rodents, rabbits, dogs, cats, pigs, cattle, sheep, horses, primates, or humans.

The term "treating" (and corresponding terms "treat" and "treatment") includes palliative, restorative, or preventative ("prophylactic") treating of a subject. The term "palliative treating" refers to treatment that eases or reduces the effect or intensity of a condition in a subject without curing the condition. The term "preventative treating" (and the corresponding term "prophylactic treating") refers to treatment that prevents the occurrence of a condition in a subject. The term "restorative treating" ("curative") refers to treatment that halts the progression of, reduces the pathologic manifestations of, or entirely eliminates a condition in a subject. Treating can be done with a therapeutically effective amount of compound, salt or composition that elicits the biological or medicinal response of a tissue, system or subject that is being sought by an individual such as a researcher, doctor, veterinarian, or clinician.

B. Compounds

In an embodiment of the present invention, there is provided a compound of I(a) or I(b):

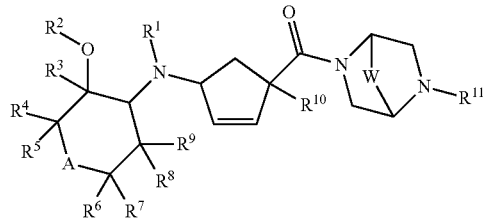

I(a)

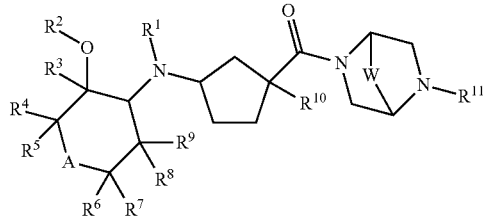

I(b)

or a pharmaceutically acceptable salt thereof, wherein:
A is O or $CF_2$;
W is $CR^{13}R^{14}$, C(O), $CHOR^{15}$, CHF, $CF_2$, O or S
$R^1$ is H or $C_{1-6}$ alkyl optionally substituted by 1-3 substituents selected from halo, OH, $CO_2H$, $CO_2$—($C_{1-6}$ alkyl), or $C_{1-3}$ alkoxy;

$R^2$ and $R^3$ are each, independently, H, $(C_1-C_6)$alkyl, $(C_1-C_6)$haloalkyl, halo, $(C_3-C_6)$cycloalkyl, CN, OH, $CO_2R$, $OCOR^{12}$; wherein said $(C_1-C_6)$alkyl is optionally substituted with one or more substituents selected from F, $(C_1-C_3)$alkoxy, OH, CN or $CO_2R^{12}$;

$R^8$ and $R^9$ are each, independently, H, $(C_1-C_6)$alkyl, $(C_1-C_6)$haloalkyl, $(C_3-C_6)$cycloalkyl, CN, OH, $CO_2R$, $OCOR^{12}$; wherein said $(C_1-C_6)$alkyl is optionally substituted with one or more substituents selected from F, $(C_1-C_3)$alkoxy, OH, CN or $CO_2R^{12}$;

$R^2$ and $R^9$, taken together may form a 5-8 membered ring;

$R^4$ and $R^7$, taken together may form a 5-8 membered ring.

$R^4$ and $R^5$ are each, independently, H, CN, $(C_1-C_6)$alkyl, halo, $(C_1-C_3)$alkoxy, $(C_1-C_3)$haloalkoxy, $(C_3-C_6)$ cycloalkyl, OH, $CO_2R^{12}$, $OCOR^{12}$, wherein said $(C_1-C_6)$alkyl is optionally substituted with one or more substituents selected from F, $C_{1-3}$ alkoxy, OH or $CO_2R^{12}$;

$R^6$ and $R^7$ are each, independently, H, CN, $(C_1-C_6)$alkyl, halo, $(C_1-C_3)$alkoxy, $(C_1-C_3)$haloalkoxy, $(C_3-C_6)$cycloalkyl, OH, $CO_2R^{12}$, $OCOR^{12}$, wherein said $(C_1-C_6)$alkyl is optionally substituted with one or more substituents selected from F, $(C_1-C_3)$ alkoxy, OH or $CO_2R^{12}$;

or $R^2$ and $R^3$ together with the carbon atom to which they are attached form a 3-7 membered spirocyclyl group;

or $R^4$ and $R^5$ together with the carbon atom to which they are attached form a 3-7 membered spirocyclyl group;

or $R^3$ and $R^4$ together with the C atoms to which they are attached form a fused 3-7 membered cycloalkyl group or 3-7 membered heterocycloalkyl group;

$R^{10}$ is $(C_1-C_6)$alkyl, $(C_1-C_6)$haloalkyl, $(C_1-C_6)$hydroxyalkyl, $(C_1-C_6)$alkoxy, $(C_3-C_6)$cycloalkyl, hydroxy$(C_3-C_6)$cycloalkyl, alkoxy cycloalkyl, OH, $(C_1-C_5)$heterocyclyl, amino, aryl or CN, $R^{11}$ is aryl or heteroaryl, said $R^{11}$ optionally, independently substituted by one or more $(C_1-C_6)$ alkyl, halo, $(C_1C_6)$haloalky $(C_1-C_6)$alkoxy, OH, amino, $C(O)NH_2$, $NH_2SO_2$, $SF_5$, or CN;

$R^{12}$ is H, $(C_1-C_4)$alkyl, or $(C_3-C_6)$cycloalkyl;

$R^{13}$ is H, halo, $(C_1-C_4)$alkyl, $(C_1-C_4)$alkoxy, or OH;

$R^{14}$ is H, halo, $(C_1-C_4)$alkyl, $(C_1-C_4)$alkoxy or OH; and $R^{15}$ is H, $(C_1-C_6)$alkyl or $(C_3-C_6)$cycloalkyl.

In another embodiment of the present invention, there is provided a compound of Formula II:

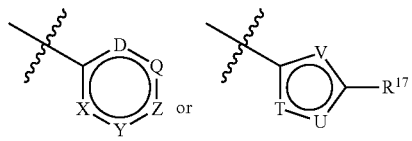

(II)

or a pharmaceutically acceptable salt thereof, wherein:

$R^1$ is H, $(C_1-C_6)$alkyl or cyclopropyl, said $(C_1-C_6)$alkyl optionally substituted by halo, CN, C(O)OH or OH;

$R^2$ is $(C_1-C_6)$alkyl $(C_1-C_6)$haloalkyl or $(C_3-C_6)$cycloalkyl;

$R^3$ $R^4$, $R^5$, $R^6$, $R^7$, $R^8$ and $R^9$ are independently H, $(C_1-C_4)$alkyl, CN, halo or amino;

$R^{10}$ is $(C_1-C_6)$alkyl, $(C_1-C_6)$haloalkyl, $(C_1-C_6)$hydroxyalkyl, $(C_1-C_6)$alkoxy, $(C_3-C_6)$cycloalkyl, hydroxy$(C_3-C_6)$cycloalkyl, alkoxy $(C_3-C_6)$cycloalkyl, OH, $(C_1-C_5)$heterocyclyl, amino, aryl or CN;

$R^{11}$ is aryl or heteroaryl, said $R^{11}$ optionally, independently substituted by one or more $(C_1-C_6)$ alkyl, halo, $(C_1-C_6)$haloalky $(C_1-C_6)$alkoxy, OH, amino, $C(O)NH_2$, $NH_2SO_2$, $SF_5$ or CN;

W is $CR^{13}R^{14}$, C(O), $CHOR^{15}$, CHF, $CF_2$, O or S;

$R^{13}$ and $R^{14}$ are independently H, halo, $(C_1-C_4)$alkyl, $(C_1-C_4)$alkoxy, or OH; and $R^{15}$ is H, $(C_1-C_6)$alkyl or $(C_3-C_6)$cycloalkyl.

In another embodiment, there is provided a compound of Formula II, or a pharmaceutically acceptable salt thereof, wherein:

$R^1$ is H or $(C_1-C_6)$alkyl $R^2$ is $(C_1-C_6)$alkyl or $(C_1-C_6)$haloalkyl $R^3$, $R^4$, $R^5$, $R^6$, $R^7$, $R^8$ and $R^9$ are each H;

$R^{11}$ is

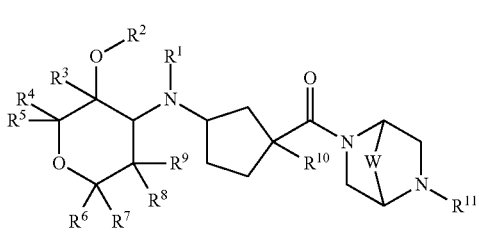

wherein X, Y, Z, Q and D are independently N or $CR^{16}$, and wherein 0, 1, 2 or 3 of X, Y, Z, Q and D are N; and wherein T, U and V are independently selected from CH, N, S, or O, provided that T and U are not both simultaneously O or S;

each $R^{16}$ is independently H, halo, $(C_1-C_6)$alkyl, $(C_1-C_6)$haloalkyl, $(C_1-C_6)$alkoxy or CN;

$R^{17}$ is H, $(C_1-C_6)$alky, $(C_1-C_6)$haloalky, or $(C_1-C_6)$alkoxy; and

W is $CR^{13}R^{14}$, C(O), $CHOR^{15}$, CHF or $CF_2$.

In some embodiments of the compound of Formula II, or a pharmaceutically acceptable salt thereof, $R^2$ is methyl.

In some embodiments of the compound of Formula II, or a pharmaceutically acceptable salt thereof, $R^1$ is H, $(C_1-C_6)$alkyl or cyclopropyl, said $(C_1-C_6)$alkyl optionally substituted by halo, CN, C(O)OH or OH;

$R^2$ is methyl;

$R^3$ $R^4$, $R^5$, $R^6$, $R^7$, $R^8$ and $R^9$ are independently H, $C_1-C_4$ alkyl, CN, halo or amino;

$R^{10}$ is $(C_1-C_6)$alkyl, $(C_1-C_6)$haloalkyl, $(C_1-C_6)$hydroxyalkyl, $(C_1-C_6)$alkoxy, $(C_3-C_6)$cycloalkyl, hydroxy$(C_3-C_6)$cycloalkyl, alkoxy $(C_3-C_6)$cycloalkyl, OH, $(C_1-C_5)$heterocyclyl, amino, aryl or CN;

$R^{11}$ is aryl or heteroaryl, said $R^{11}$ optionally, independently substituted by one or more $(C_1-C_6)$ alkyl, halo, $(C_1-C_6)$haloalky $(C_1-C_6)$alkoxy, OH, amino, $C(O)NH_2$, $NH_2SO_2$, $SF_5$ or CN;

W is $CR^{13}R^{14}$, C(O), $CHOR^{15}$, CHF, $CF_2$, O or S;

$R^{13}$ and $R^{14}$ are independently H halo, $(C_1-C_4)$alkyl, $(C_1-C_4)$alkoxy, or OH; and $R^{15}$ is H, $(C_1-C_6)$alkyl or $(C_3-C_6)$cycloalkyl.

In some embodiments of the compound of Formula II, or a pharmaceutically acceptable salt thereof, $R^{10}$ is

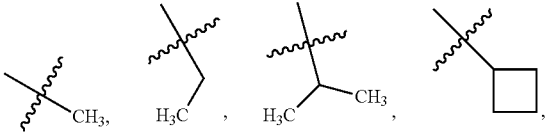

-continued

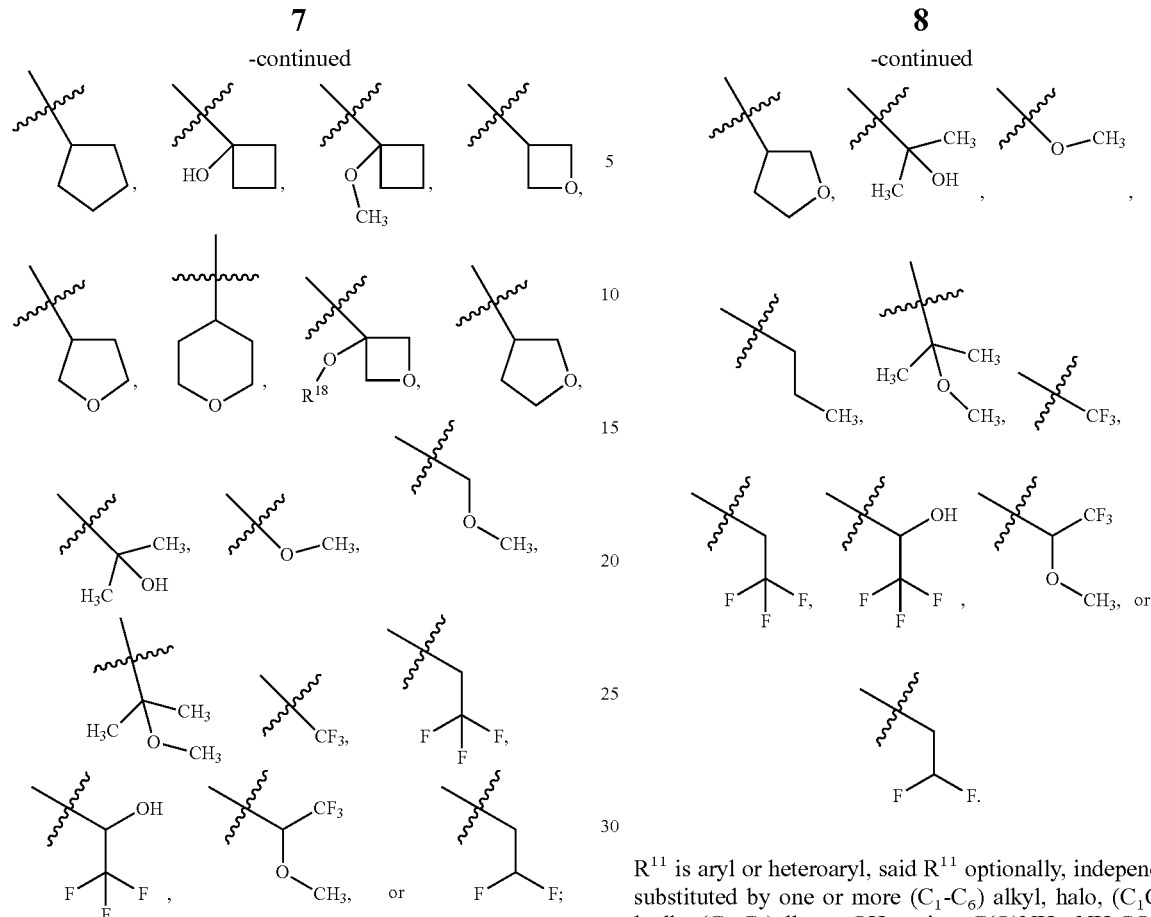

wherein R$^{18}$ is H or (C$_1$-C$_6$)alkyl

In some embodiments of the compound of Formula II, or a pharmaceutically acceptable salt thereof, R$^1$ is H, (C$_1$-C$_6$)alkyl or cyclopropyl, said (C$_1$-C$_6$)alkyl optionally substituted by halo, CN, C(O)OH or OH;

R$^2$ is methyl;

R$^3$ R$^4$, R$^5$, R$^6$, R$^7$, R$^8$ and R$^9$ are independently H, C$_1$-C$_4$ alkyl, CN, halo or amino;

R$^{10}$ is

R$^{11}$ is aryl or heteroaryl, said R$^{11}$ optionally, independently substituted by one or more (C$_1$-C$_6$) alkyl, halo, (C$_1$C$_6$)haloalky (C$_1$-C$_6$)alkoxy, OH, amino, C(O)NH$_2$, NH$_2$SO$_2$, SF$_5$ or CN;

W is CR$^{13}$R$^{14}$, C(O), CHOR$^{15}$, CHF, CF$_2$, O or S;

R$^{13}$ and R$^{14}$ are independently H halo, (C$_1$-C$_4$)alkyl, (C$_1$-C$_4$) alkoxy, or OH;

R$^{15}$ is H, (C$_1$-C$_6$)alkyl or (C$_3$-C$_6$)cycloalkyl; and

R$^{18}$ is H or (C$_1$-C$_6$)alkyl.

In some embodiments of the present invention, there is provided a compound of Formula II, or a pharmaceutically acceptable salt thereof, wherein R$^{11}$ is

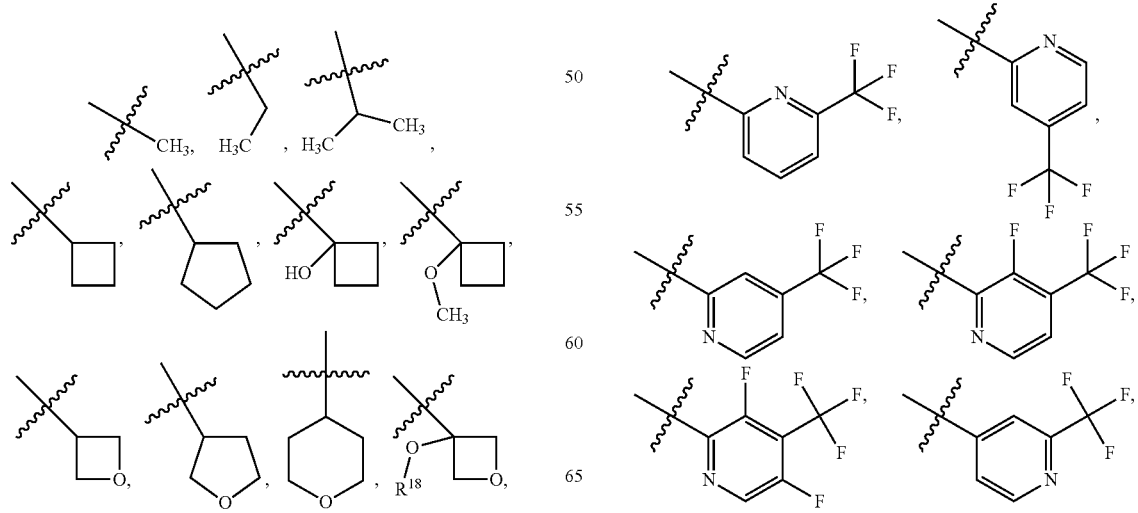

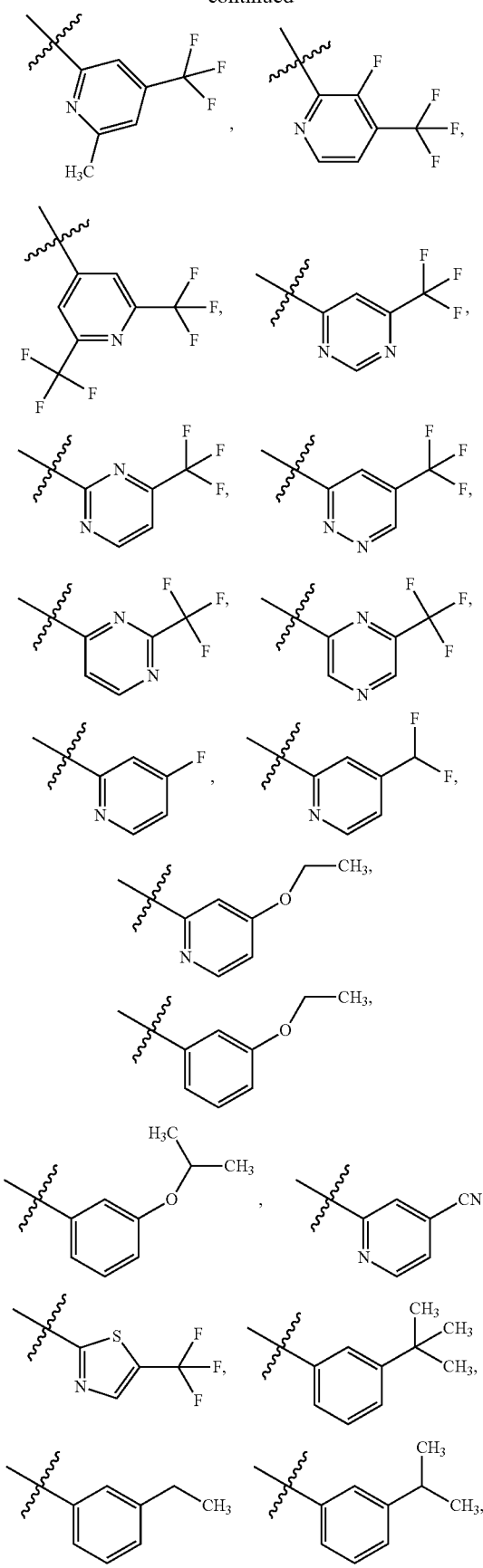

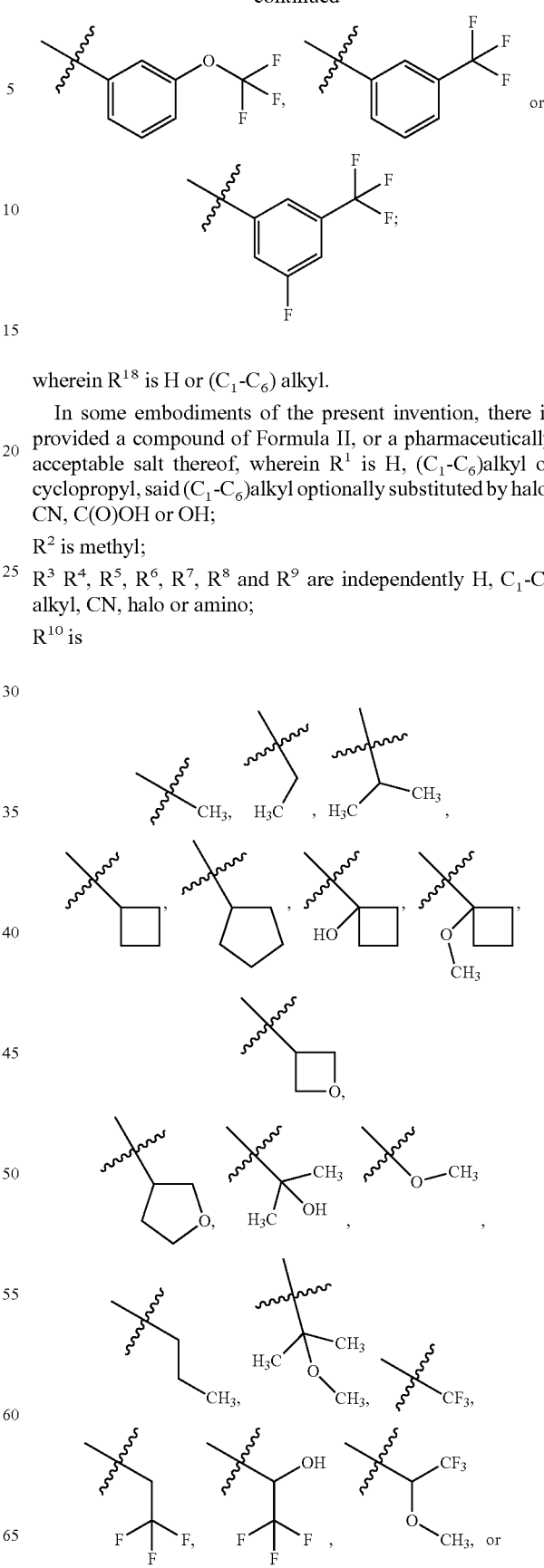

wherein R¹⁸ is H or $(C_1-C_6)$ alkyl.

In some embodiments of the present invention, there is provided a compound of Formula II, or a pharmaceutically acceptable salt thereof, wherein $R^1$ is H, $(C_1-C_6)$alkyl or cyclopropyl, said $(C_1-C_6)$alkyl optionally substituted by halo, CN, C(O)OH or OH;

$R^2$ is methyl;

$R^3$ $R^4$, $R^5$, $R^6$, $R^7$, $R^8$ and $R^9$ are independently H, $C_1$-$C_4$ alkyl, CN, halo or amino;

$R^{10}$ is

-continued
R¹¹ is
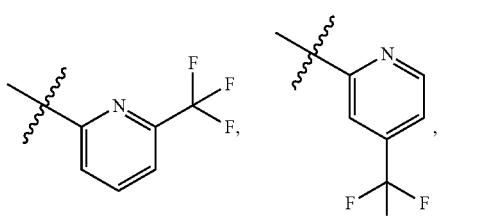
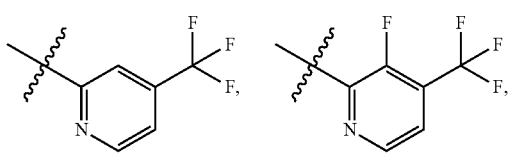
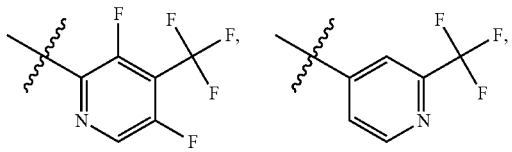
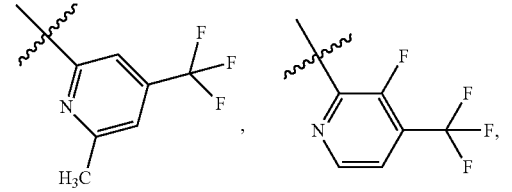
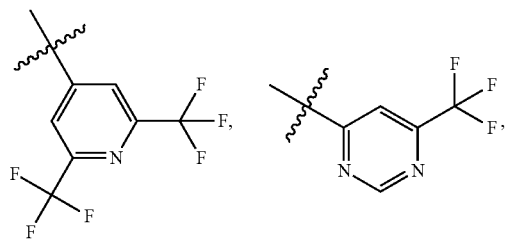
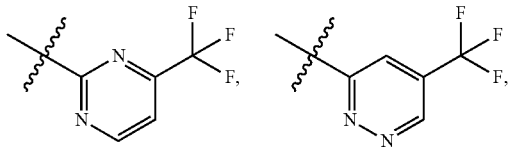
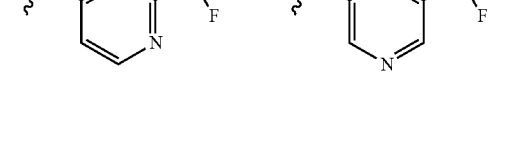
-continued
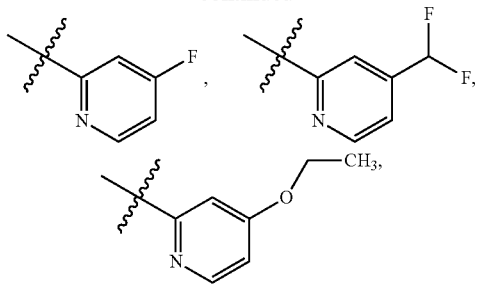
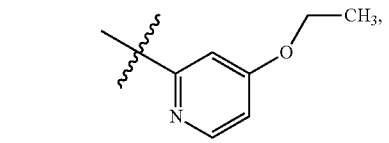
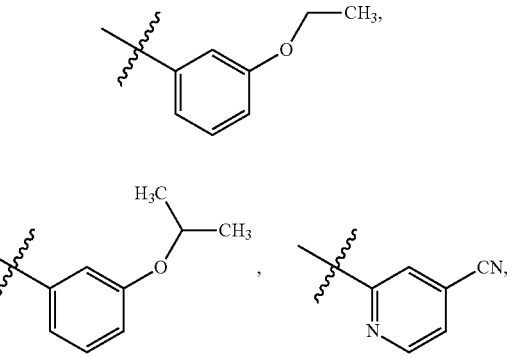
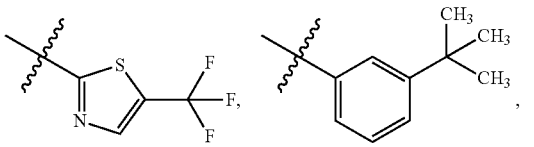
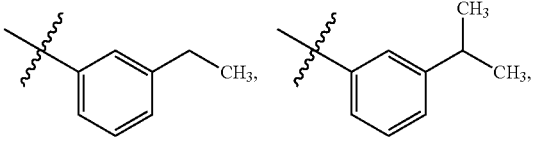
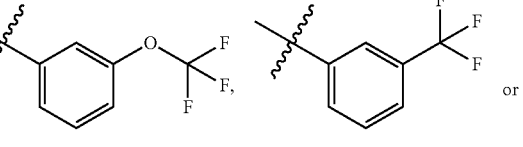
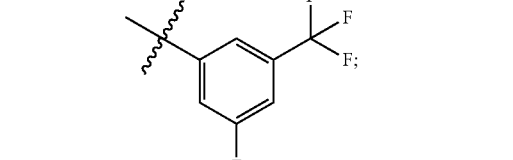
wherein R¹⁸ is H or $(C_1-C_6)$ alkyl;
W is $CR^{13}R^{14}$, C(O), $CHOR^{15}$, CHF, $CF_2$, O or S;
$R^{13}$ and $R^{14}$ are independently H halo, $(C_1-C_4)$alkyl, $(C_1-C_4)$ alkoxy, or OH; and
$R^{15}$ is H, $(C_1-C_6)$alkyl or $(C_3-C_6)$cycloalkyl.
In some embodiments, there is provided a compound of Formula II, or pharmaceutically acceptable salt thereof, wherein $R^{10}$ is

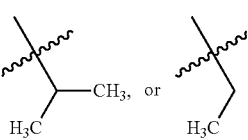

and
R¹¹ is

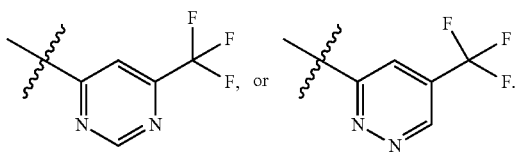

In some embodiments, there is provided a compound of Formula II, or pharmaceutically acceptable salt thereof, wherein
R¹ is H;
R² is methyl;
R³ R⁴, R⁵, R⁶, R⁷, R⁹ and R⁹ are each H;
R¹⁰ is

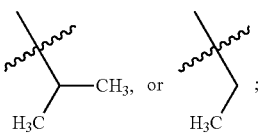

R¹¹ is

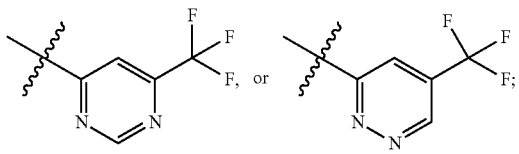

and
W is CH₂.

In another embodiment, there is provided compound, or pharmaceutically acceptable salt thereof, selected from the group consisting of:

1,5-anhydro-2,3-dideoxy-3-{[(1R,3S)-3-ethyl-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-ethyl-3-({(1S,4S)-5-[3-fluoro-4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-methyl-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-methyl-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[5-(trifluoromethyl)pyridazin-3-yl]-2,5-diazabicyclo[2.2.1]hept-2-yl}carbonyl)cyclopentyl]amino}-4-O-methyl-D-erythro-pentitol;

1,5-anhydro-3-{[(1R,3S)-3-isopropyl-3-({(1S,4S)-5-[2,6-bis(trifluoromethyl)pyridin-4-yl]-2,5-diazabicyclo[2.2.1]hept-2-yl}carbonyl)-3-isopropylcyclopentyl]amino}-2,3-dideoxy-4-O-methyl-D-erythro-pentitol;

1,5-anhydro-2,3-dideoxy-3-{[(1R,3S)-3-({(1S,4S)-5-[3-fluoro-4-(trifluoromethyl)pyridin-2-yl]-2,5-diazabicyclo[2.2.1]hept-2-yl}carbonyl)-3-isopropylcyclopentyl]amino}-4-O-methyl-D-erythro-pentitol;

1,5-anhydro-2,3-dideoxy-3-{[(1R,3S)-3-isopropyl-3-({(1S,4S)-5-[6-methyl-4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-isopropyl-3-({(1S,4S)-5-[3-(trifluoromethyl)phenyl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-({(1S,4S)-5-[3-fluoro-5-(trifluoromethyl)phenyl]-2,5-diazabicyclo[2.2.1]hept-2-yl}carbonyl)-3-isopropylcyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol 1,5-anhydro-2,3-dideoxy-3-{[(1R,3S)-3-(2,2-difluoroethyl)-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-anhydro-2,3-dideoxy-3-{[(1R,3S)-3-(2,2-difluoroethyl)-3-({(1S,4S)-5-[5-(trifluoromethyl)pyridazin-3-yl]-2,5-diazabicyclo[2.2.1]hept-2-yl}carbonyl)cyclopentyl]amino}-4-O-methyl-D-erythro-pentitol;

1,5-anhydro-2,3-dideoxy-4-O-methyl-3-{[(1R,3S)-3-(2,2,2-trifluoroethyl)-3-({(1S,4S)-5-[6-(trifluoromethyl)pyrimidin-4-yl]-2,5-diazabicyclo[2.2.1]hept-2-yl}carbonyl)cyclopentyl]amino}-D-erythro-pentitol;

1,5-anhydro-2,3-dideoxy-4-O-methyl-3-{[(1R,3S)-3-(2,2,2-trifluoroethyl)-3-({(1S,4S)-5-[4-(trifluoromethyl)pyridin-2-yl]-2,5-diazabicyclo[2.2.1]hept-2-yl}carbonyl)cyclopentyl]amino}-D-erythro-pentitol;

1,5-anhydro-2,3-dideoxy-4-O-methyl-3-{[(1R,3S)-3-(2,2,2-trifluoroethyl)-3-({(1S,4S)-5-[2-(trifluoromethyl)pyridin-4-yl]-2,5-diazabicyclo[2.2.1]hept-2-yl}carbonyl)cyclopentyl]amino}-D-erythro-pentitol;

1,5-anhydro-2,3-dideoxy-4-O-methyl-3-{[(1R,3S)-3-(2,2,2-trifluoroethyl)-3-({(1S,4S)-5-[4-(trifluoromethyl)pyrimidin-2-yl]-2,5-diazabicyclo[2.2.1]hept-2-yl}carbonyl)cyclopentyl]amino}-D-erythro-pentitol;

1,5-anhydro-2,3-dideoxy-4-O-methyl-3-{[(1R,3S)-3-(2,2,2-trifluoroethyl)-3-({(1S,4S)-5-[6-(trifluoromethyl)pyrimidin-2-yl]-2,5-diazabicyclo[2.2.1]hept-2-yl}carbonyl)cyclopentyl]amino}-D-erythro-pentitol;

1,5-anhydro-2,3-dideoxy-4-O-methyl-3-{[(1R,3S)-3-(2,2,2-trifluoroethyl)-3-({(1S,4S)-5-[6-(trifluoromethyl)pyrazin-2-yl]-2,5-diazabicyclo[2.2.1]hept-2-yl}carbonyl)cyclopentyl]amino}-D-erythro-pentitol;

1,5-anhydro-2,3-dideoxy-4-O-methyl-3-{[(1R,3S)-3-(2,2,2-trifluoroethyl)-3-({(1S,4S)-5-[2-(trifluoromethyl)pyridin-4-yl]-2,5-diazabicyclo[2.2.1]hept-2-yl}carbonyl)cyclopentyl]amino}-D-erythro-pentitol 1,5-anhydro-2,3-dideoxy-4-O-methyl-3-{[(1R,3S)-3-(2,2,2-trifluoroethyl)-3-({(1S,4S)-5-[5-(trifluoromethyl)pyridazin-3-yl]-2,5-diazabicyclo[2.2.1]hept-2-yl}carbonyl)cyclopentyl]amino}-D-erythro-pentitol;

1,5-anhydro-2,3-dideoxy-3-{[(1S,4S)-4-isopropyll-4-({(1S,4S)-5-[4-(trifluoromethyl)pyridin-2-yl]-2,5-diazabicyclo[2.2.1]hept-2-yl}carbonyl)cyclopent-2-en-1-yl]amino}-4-O-methyl-D-erythro-pentitol;

1,5-anhydro-2,3-dideoxy-3-{[(1S,4S)-4-isopropyll-4-({(1S,4S)-5-[4-(trifluoromethyl)pyrimidin-2-yl]-2,5-diazabicyclo[2.2.1]hept-2-yl}carbonyl)cyclopent-2-en-1-yl]amino}-4-O-methyl-D-erythro-pentitol;

1,5-anhydro-2,3-dideoxy-3-{[(1S,4S)-4-isopropyll-4-({(1S,4S)-5-[6-(trifluoromethyl)pyridin-2-yl]-2,5-diazabicyclo[2.2.1]hept-2-yl}carbonyl)cyclopent-2-en-1-yl]amino}-4-O-methyl-D-erythro-pentitol;

1,5-anhydro-2,3-dideoxy-3-{[(1S,4S)-4-isopropyll-4-({(1S,4S)-5-[6-(trifluoromethyl)pyrazin-2-yl]-2,5-diazabicyclo[2.2.1]hept-2-yl}carbonyl)cyclopent-2-en-1-yl]amino}-4-O-methyl-D-erythro-pentitol;

1,5-anhydro-3-{[(1R,3S)-3-{[(1S,4S)-5-(tert-butoxycarbonyl)-2,5-diazabicyclo[2.2.1]hept-2-yl]carbonyl}-3-ethylcyclopentyl]amino}-2,3-dideoxy-4-O-methyl-D-erythro-pentitol;

1,5-anhydro-3-{[(1R,3S)-3-{[(1S,4S)-5-(tert-butoxycarbonyl)-2,5-diazabicyclo[2.2.1]hept-2-yl]carbonyl}-3-(2,2,2-trifluoroethyl)cyclopentyl]amino}-2,3-dideoxy-4-O-methyl-D-erythro-pentitol;

1,5-Anhydro-2,3-dideoxy-3-{[(1R,3S)-3-(1-hydroxycyclobutyl)-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-Anhydro-2,3-dideoxy-3-{[(1R,3S)-3-(1-hydroxycyclobutyl)-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol;

1,5-Anhydro-2,3-dideoxy-3-{[(1R,3S)-3-(1-hydroxycyclobutyl)-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol;

1,5-Anhydro-2,3-dideoxy-3-{[(1R,3S)-3-(1-hydroxycyclobutyl)-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol 1,5-anhydro-2,3-dideoxy-3-{[(1R,3S)-3-(1-hydroxycyclobutyl)-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol;

1,5-Anhydro-2,3-dideoxy-3-{[(1R,3S)-3-(1-hydroxycyclobutyl)-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol;

1,5-Anhydro-2,3-dideoxy-3-{[(1R,3S)-3-(1-hydroxycyclobutyl)-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol;

1,5-Anhydro-2,3-dideoxy-3-{[3-(1-hydroxy-1-methylethyl)-3-({5-[4-(trifluoromethyl)pyridin-2-yl]-2,5-diazabicyclo[2.2.1]hept-2-yl}carbonyl)cyclopentyl]amino}-4-O-methylpentitol;

1,5-Anhydro-2,3-dideoxy-3-{[3-(1-hydroxy-1-methylethyl)-3-({5-[6-(trifluoromethyl)pyrimidin-4-yl]-2,5-diazabicyclo[2.2.1]hept-2-yl}carbonyl)cyclopentyl]amino}-4-O-methylpentitol;

1,5-Anhydro-2,3-dideoxy-3-{[3-(1-hydroxy-1-methyl-ethyl)-3-({5-[4-(trifluoromethyl)pyrimidin-2-yl]-2,5-diazabicyclo[2.2.1]hept-2-yl}carbonyl)cyclopentyl]amino}-4-O-methylpentitol;

1,5-Anhydro-2,3-dideoxy-3-{[3-(1-hydroxy-1-methyl-ethyl)-3-({5-[5-(trifluoromethyl)pyridazin-3-yl]-2,5-diazabicyclo[2.2.1]hept-2-yl}carbonyl)cyclopentyl]amino}-4-O-methylpentitol;

1,5-Anhydro-2,3-dideoxy-3-{[3-(1-hydroxy-1-methyl-ethyl)-3-({5-[2-(trifluoromethyl)pyrimidin-4-yl]-2,5-diazabicyclo[2.2.1]hept-2-yl}carbonyl)cyclopentyl]amino}-4-O-methylpentitol;

1,5-Anhydro-2,3-dideoxy-3-{[3-(1-hydroxy-1-methyl-ethyl)-3-({5-[6-(trifluoromethyl)pyridin-2-yl]-2,5-diazabicyclo[2.2.1]hept-2-yl}carbonyl)cyclopentyl]amino}-4-O-methylpentitol;

1,5-Anhydro-2,3-dideoxy-3-{[3-(1-hydroxy-1-methyl-ethyl)-3-({5-[2-(trifluoromethyl)pyridin-4-yl]-2,5-diazabicyclo[2.2.1]hept-2-yl}carbonyl)cyclopentyl]amino}-4-O-methylpentitol; and 1,5-Anhydro-2,3-dideoxy-3-{[3-(1-hydroxy-1-methyl-ethyl)-3-({5-[6-(trifluoromethyl)pyrazin-2-yl]-2,5-diazabicyclo[2.2.1]hept-2-yl}carbonyl)cyclopentyl]amino}-4-O-methylpentitol.

In another embodiment, there is provided a compound of formula:

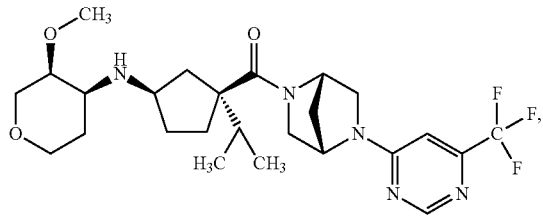

or a pharmaceutically acceptable salt thereof.

In another embodiment, there is provided a compound of formula

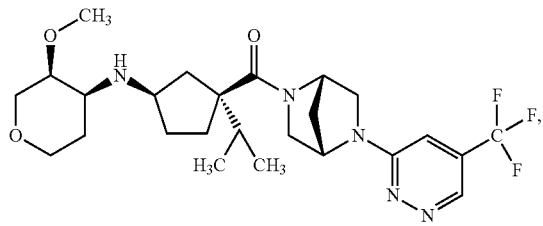

or a pharmaceutically acceptable salt thereof.

In another embodiment of the present invention, there is provided a composition comprising a compound of Formula I or II, or a pharmaceutically acceptable salt thereof, and a carrier.

In another embodiment, there is provided a method of treating a disease associated with expression or activity of a chemokine receptor in a patient comprising administering to said patient a compound of Formula I or II, or a pharmaceutically acceptable salt thereof.

In one embodiment of the method, said chemokine receptor is CCR2 or CCR5.

In another embodiment of the method, the disease is rheumatoid arthritis, atherosclerosis, lupus, multiple sclerosis, pain, transplant rejection, diabetes, diabetic nephropathy, diabetic conditions, liver fibrosis, viral disease, cancer, asthma, seasonal and perennial allergic rhinitis, sinusitis, conjunctivitis, age-related macular degeneration, food allergy, scombroid poisoning, psoriasis, undifferentiated spondyloarthropy, gout, urticaria, pruritus, eczema, inflammatory bowel disease, thrombotic disease, otitis media, fibrosis, liver cirrhosis, cardiac disease, Alzheimer's disease, sepsis, restenosis, Crohn's disease, ulcerative colitis, irritable bowel syndrome, hypersensitivity lung diseases, drug-induced pulmonary fibrosis, chronic obstructive pulmonary disease, arthritis, nephritis, atopic dermatitis, stroke, acute nerve injury, sarcoidosis, hepatitis, endometriosis, neuropathic pain, hypersensitivity pneumonitis, eosinophilic pneumonias, delayed-type hypersensitivity, interstitial lung disease, eye disorders or obesity.

In anther embodiment of the present invention, there is provided the use of a compound of Formula I or II, or a pharmaceutically acceptable salt thereof, in the manufacture of a medicament for the treatment of rheumatoid arthritis, atherosclerosis, lupus, multiple sclerosis, pain, transplant rejection, diabetes, diabetic nephropathy, diabetic conditions, liver fibrosis, viral disease, cancer, asthma, seasonal and perennial allergic rhinitis, sinusitis, conjunctivitis, age-related macular degeneration, food allergy, scombroid poisoning, psoriasis, undifferentiated spondyloarthropy, gout, urticaria, pruritus, eczema, inflammatory bowel disease, thrombotic disease, otitis media, fibrosis, liver cirrhosis, cardiac disease, Alzheimer's disease, sepsis, restenosis, Crohn's disease, ulcerative colitis, irritable bowel syndrome, hypersensitivity lung diseases, drug-induced pulmonary fibrosis, chronic obstructive pulmonary disease, arthritis, nephritis, atopic dermatitis, stroke, acute nerve injury, sarcoidosis, hepatitis, endometriosis, neuropathic pain, hypersensitivity pneumonitis, eosinophilic pneumonias, delayed-type hypersensitivity, interstitial lung disease, eye disorders or obesity.

In another embodiment, the present invention relates to a combination for treating a CCR2 or CCR2/CCR5 mediated disease, disorder or condition, said combination comprising a compound of Formula I or II as defined above, or a pharmaceutically acceptable salt thereof, and one or more additional therapeutic agents.

In another embodiment, the present invention relates to a compound of formula I or II as defined above, or a pharmaceutically acceptable salt thereof, as defined above, for use as a medicament.

In another embodiment, the present invention is directed to a method of treating a CCR2 or CCR2/CCR5 mediated disease, disorder or condition in a subject in need of such treatment, by administering a therapeutically effective amount of a compound of Formula I or II as defined above, or a pharmaceutically acceptable salt or solvate thereof to said subject.

In another embodiment, the present invention is directed to a compound of Formula I or II as defined above, or a pharmaceutically acceptable salt thereof, for use in treating a CCR2 or CCR2/CCR5 mediated disease, disorder or condition.

In another embodiment, the present invention is directed to the use of a compound of Formula I or II as defined above, or a pharmaceutically acceptable salt or solvate thereof, for the manufacture of a medicament for treating a CCR2 or CCR2/CCR5 mediated disease, disorder or condition.

Salts of compounds of the invention can include the acid addition salts or base addition salts (including disalts) thereof. The salts can be pharmaceutically acceptable.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

A salt may be readily prepared by mixing together solutions of compounds of the present invention and the desired acid or base, as appropriate. The salt may precipitate from solution and be collected by filtration or may be recovered by evaporation of the solvent. The degree of ionization in the salt may vary from completely ionized to almost non-ionized.

The compounds of the present invention may be administered as prodrugs. Thus, certain derivatives which may have little or no pharmacological activity themselves can, when administered into or onto the body, be converted into compounds of the present invention having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T Higuchi and W Stella) and 'Bioreversible Carriers in Drug Design', Pergamon Press, 1987 (ed. E B Roche, American Pharmaceutical Association).

Prodrugs can, for example, be produced by replacing appropriate functionalities present in the compounds of the present invention with certain moieties known to those skilled in the art as 'pro-moieties' as described, for example, in "Design of Prodrugs" by H Bundgaard (Elsevier, 1985).

Some examples of such prodrugs include:

(i) where the compound contains an alcohol functionality (—OH), an ether thereof, for example, replacement of the hydrogen with $(C_1-C_6)$alkanoyloxymethyl; and (ii) where the compound contains a secondary amino functionality, an amide thereof, for example, replacement of hydrogen with $(C_1-C_{10})$alkanoyl. All isomers, such as stereoisomers, geometric (cis/trans or Z/E) isomers and tautomeric forms of the compounds or salts are included in the scope of the present invention, including compounds or salts having more than one type of isomerism, and mixtures of one or more thereof.

Also included are acid addition or base salts wherein the counterion is optically active, for example, D-lactate or L-lysine, or racemic, for example, DL-tartrate or DL-arginine.

Isomers may be separated by conventional techniques well known to those skilled in the art.

The present invention includes isotopically-labelled compounds of the invention wherein one or more atoms are replaced by atoms having the same atomic number, but an atomic mass or mass number different from the atomic mass or mass number usually found in nature.

Isotopically-labeled compounds of the invention can generally be prepared by conventional techniques known to those skilled in the art or by processes analogous to those described in the accompanying Examples and Preparations using an appropriate isotopically-labelled reagent in place of the non-labeled reagent previously employed.

For the treatment of the conditions referred to below, the compounds of the present invention can be administered. Salts of the compounds of the present invention could also be used.

C. Compositions

Compounds or salts of the present invention could be part of a composition. Compositions can also include one or more compounds or salts of the present invention. The composition can also include an enantiomeric excess of one or more compounds of the present invention. Other pharmacologically active substances and carriers can be included in the composition.

One embodiment is a composition comprising a compound of Formula I or II, or a salt thereof. Another embodiment is a composition comprising a compound of Formula I or II, or a salt thereof and a carrier.

For example, the carrier can be an excipient. The choice of excipient will to a large extent depend on factors such as the particular mode of administration, the effect of the excipient on solubility and stability, and the nature of the dosage form.

The composition can be a solid, a liquid, or both, and may be formulated with the compound as a unit-dose composition, for example, a tablet, which can contain from 0.05% to 95% by weight of the active compounds. Compounds or salts of the present invention may be coupled with suitable polymers as targetable drug carriers.

D. Methods

In some embodiments, compounds of the invention can be used in methods that modulate activity of one or more chemokine receptors. Accordingly, the invention includes methods comprising contacting a chemokine receptor with a compound of Formula I or II, or a salt thereof. In some embodiments, the chemokine receptor is CCR2. In other embodiments, the chemokine receptor is CCR5. In other embodiments, the invention includes methods of modulating a chemokine receptor by contacting the receptor with any one or more of the compounds or compositions described herein. In some embodiments, compounds of the present invention can act as inhibitors or antagonist of chemokine receptors. In further embodiments, the compounds of the invention can be used to modulate activity of a chemokine receptor in an individual in need of modulation of the receptor by administering a modulating amount of a compound of Formula I or II, or a slat thereof.

Chemokine receptors to which the present compounds bind and/or modulate include any chemokine receptor. In some embodiments, the chemokine receptor belongs to the CC family of chemokine receptors including, for example, CCR1, CCR2, CCR3, CCR4, CCR5, CCR6, CCR7, CCR8, and CCR10. In some embodiments, the chemokine receptor is CCR2 or CCR5. In other embodiments, the chemokine receptor is CCR2. In some embodiments, the chemokine receptor is CCR5. In some embodiments, the chemokine receptor binds and/or modulates both CCR2 and CCR5.

The compounds of the invention can be selective, that is a compound binds to or inhibits a chemokine receptor with greater affinity or potency, respectively, compared to at least one other chemokine receptor.

Compounds of the invention can be dual inhibitors or binders of CCR2 and CCR5, meaning that the compounds of the invention can bind to or inhibit both CCR2 and CCR5 with greater affinity or potency, respectively, than for other chemokine receptors such as CCR1, CCR3, CCR4, CCR6, CCR7, CCR8, and CCR10. In some embodiments, the compounds of the invention have binding or inhibition selectivity for CCR2 and CCR5 over any other chemokine receptor. Binding affinity and inhibitor potency can be measured according to routine methods in the art, such as according to the assays provided herein.

The present invention further provides methods of treating a chemokine receptor-associated disease or disorder in an individual (e.g., patient) by administering to the individual in need of such treatment a therapeutically effective amount or dose of a compound of the present invention or a pharmaceutical composition thereof. In other embodiments, the invention includes method of treating a condition mediated by chemokine receptor activity in a subject comprising administering to the subject a compound of Formula I or II, or a pharmaceutically acceptable salt thereof.

A chemokine receptor-associated disease or condition can include any disease, disorder or condition that is directly or indirectly linked to expression or activity of the chemokine receptor. A chemokine receptor-associated disease or condition can also include any disease, disorder or condition that can be prevented, ameliorated, or cured by modulating chemokine receptor activity. A chemokine receptor-associated disease can further include any disease, disorder or condition that is characterized by binding of an infectious agent such as a virus or viral protein with a chemokine receptor. In some embodiments, the chemokine receptor-associated disease is a CCR5-associated disease such as HIV infection.

Examples of a condition mediated by chemokine receptor include inflammation, inflammatory diseases, immune disorders, pains; cancers, or viral infections.

Examples of a condition mediated by chemokine receptor include inflammation, inflammatory diseases, immune disorders, pains, cancers, or viral infections.

Examples of inflammatory diseases include diseases believed to have an inflammatory component such as asthma, seasonal and perennial allergic rhinitis, sinusitis, conjunctivitis, age-related macular degeneration, food allergy, scombroid poisoning, psoriasis, undifferentiated spondyloarthropy, juvenile-onset spondyloarthritis, gout, urticaria, pruritus, eczema, inflammatory bowel disease, thrombotic disease, otitis media, fibrosis, liver fibrosis, liver cirrhosis, cardiac disease, Alzheimer's disease, sepsis, restenosis, atherosclerosis, multiple sclerosis, Crohn's disease, ulcerative colitis, irritable bowel syndrome, inflammatory bowel disease, hypersensitivity lung diseases, drug-induced pulmonary fibrosis, chronic obstructive pulmonary disease (COPD), arthritis, nephritis, ulcerative colitis, atopic dermatitis, stroke, acute nerve injury, sarcoidosis, hepatitis, endometriosis, neuropathic pain, hypersensitivity pneumonitis, eosinophilic pneumonias, delayed-type hypersensitivity, interstitial lung disease (ILD) (e.g., idiopathic pulmonary fibrosis, or ILD associated with rheumatoid arthritis, systemic lupus erythematosus, ankylosing spondylitis, systemic sclerosis, Sjogren's syndrome, polymyositis or dermatomyositis, eye disorders (e.g., retinal neurodegeneration, choroidal neovascularization, etc.) and the like.

Example immune disorders include rheumatoid arthritis, psoriatic arthritis, systemic lupus erythematosus, myastenia gravis, juvenile onset diabetes; glomerulonephritis, autoimmune throiditis, organ transplant rejection including allograft rejection and graft-versus-host disease.

Examples of pain include nociceptive and neuropathic pain. The pain can be acute or chronic. Pain includes cutaneous pain, somatic pain, visceral pain, and phantom limb pain. Pain also includes fibromyalgia, rheumatoid arthritis pain, osteoarthritis pain, and pain associated with the other diseases and conditions detailed herein.

Example cancers include breast cancer, ovarian cancer, multiple myeloma and the like that are characterized by infiltration of macrophages (e.g., tumor associated macrophages, TAMs) into tumors or diseased tissues.

Example viral infections include influenza, avian influenza, herpes infection, HIV infection or AIDS.

Further inflammatory or immune diseases treatable by administration of a compound of the present invention include, for example, autoimmune nephritis, lupus nephritis, Goodpasture's syndrome nephritis and Wegeners granulomatosis nephritis, lupus erythematosus, Goodpasture's syndrome and Wegeners granulomatosis.

Examples of diabetic conditions include diabetes, insulin resistance, diabetic neuropathy, diabetic nephropathy, diabetic retinopathy, cataracts, hyperglycemia, hypercholesterolemia, hypertension, hyperinsulinemia, hyperlipidemia, atherosclerosis, tissue ischemia, diabetic cardiomyopathy, diabetic microangiopathy, diabetic macroangiopathy and foot ulcers. Included in the treatment of diabetes is the prevention or attenuation of long term conditions such as neuropathy, nephropathy, retinopathy or cataracts.

In some embodiments, the condition to be treated is rheumatoid arthritis, atherosclerosis, lupus, multiple sclerosis, neuropathic pain, transplant rejection, diabetes, diabetic nephropathy, diabetic conditions, or obesity.

In some embodiments, the condition is rheumatoid arthritis.

In some embodiments, the condition is diabetes.

In some embodiments, the condition is diabetic nephropathy.

In some embodiments, the condition is liver fibrosis.

In some embodiments, the condition is osteoarthritis pain.

In some embodiments, the condition is breast cancer, ovarian cancer or multiple myeloma.

In some embodiments, the condition is HIV infection.

E. Dosage and Administration

Pharmaceutical Formulations and Dosage Forms

When employed as pharmaceuticals, the compounds of Formula I or II can be administered in the form of pharmaceutical compositions. These compositions can be prepared in a manner well known in the pharmaceutical art, and can be administered by a variety of routes depending upon whether local or systemic treatment is desired and upon the area to be treated. Administration can be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or can be, for example, by a continuous perfusion pump. Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

This invention also includes pharmaceutical compositions which contain, as the active ingredient, one or more of the compounds of Formula I or II above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1000 mg (1 g), more usually about 100 to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

In some embodiments, the compounds or compositions of the invention contain from about 5 to about 50 mg of the active ingredient. One having ordinary skill in the art will appreciate that this embodies compounds or compositions containing from about 5 to about 10, from about 10 to about 15, from about 15 to about 20, from about 20 to about 25, from about 25 to about 30, from about 30 to about 35, from about 35 to about 40, from about 40 to about 45, or from about 45 to about 50 mg of the active ingredient. In another embodiment, the dose can be 35-45 mg.

In some embodiments, the compounds or compositions of the invention contain from about 50 to about 500 mg of the active ingredient. One having ordinary skill in the art will appreciate that this embodies compounds or compositions containing from about 50 to about 75, from about 75 to about 100, from about 100 to about 125, from about 125 to about 150, from about 150 to about 175, from about 175 to about 200, from about 200 to about 225, from about 225 to about 250, from about 250 to about 275, from about 275 to about 300, from about 300 to about 325, from about 325 to About 350, from about 350 to about 375, from about 375 to about 400, from about 400 to about 425, from about 425 to about 450, from about 450 to about 475, or from about 475 to about 500 mg of the active ingredient.

In some embodiments, the compounds or compositions of the invention contain from about 500 to about 1000 mg of the active ingredient. One having ordinary skill in the art will appreciate that this embodies compounds or compositions containing from about 500 to about 550, from about 550 to about 600, from about 600 to about 650, from about 650 to about 700, from about 700 to about 750, from about 750 to about 800, from about 800 to about 850, from about 850 to about 900, from about 900 to about 950, or from about 950 to about 1000 mg of the active ingredient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patients symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, or from 5 to 9, or from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antibodies, immune suppressants, anti-inflammatory agents, chemotherapeutics, lipid lowering agents, HDL elevating agents, insulin secretagogues or sensitizers, drugs used for the treatment of rheumatoid arthritis and the like.

Rheumatoid Arthritis (RA) Treatment Regimen

Rheumatoid arthritis (RA) patients, treated aggressively with disease modifying agents (methotrexate, antimalarials, gold, penicillamine, sulfasalazine, dapsone, leflunamide, or biologicals), can achieve varying degrees of disease control, including complete remissions. These clinical responses are associated with improvement in standardized scores of disease activity, specifically the ACR criteria which includes: pain, function, number of tender joints, number of swollen joints, patient global assessment, physician global assessment, laboratory measures of inflammation (CRP and ESR), and radiologic assessment of joint structural damage. Current disease-modifying drugs (DMARDs) require continued administration to maintain optimal benefit. Chronic dosing of these agents is associated with significant toxicity and host defense compromise. Additionally, patients often become refractory to a particular therapy and require an alternative regimen. For these reasons, a novel, effective therapy which allows withdrawal of standard DMARDs would be a clinically important advance.

Patients with significant response to anti-TNF therapies (infliximab, etanercept, adalimumab), anti-IL-1 therapy (kinaret) or other disease modifying anti-rheumatic drugs (DMARDs) including but not limited to methotrexate, cyclosporine, gold salts, antimalarials, penicillamine or leflunamide, who have achieved clinical remission of disease can be treated with a substance that inhibits expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art).

In some embodiments, the substance that inhibits expression and/or activity of CCR2 is a small molecule CCR2 inhibitor (or antagonist). The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Treating patients with a combination of CCR2 antagonist and their current therapy can be carried out for, for example, about one to about two days, before discontinuing or dose reducing the DMARD and continuing on CCR2 antagonist.

Advantages of substituting traditional DMARDS with CCR2 antagonists are numerous. Traditional DMARDs have serious cumulative dose-limiting side effects, the most common being damage to the liver, as well as immunosuppressive actions. CCR2 antagonism is expected to have an improved long-term safety profile and will not have similar immunosuppressive liabilities associated with traditional DMARDs. Additionally, the half-life of the biologicals is typically days or weeks, which is an issue when dealing with adverse reactions. The half-life of an orally bioavailable CCR2 antagonist is expected to be on the order of hours so the risk of continued exposure to the drug after an adverse event is very minimal as compared to biological agents. Also, the current biologic agents (infliximab, etanercept, adalimumab, kinaret) are typically given either i.v. or s.c., requiring doctor's administration or patient self-injection. This leads to the possibility of infusion reaction or injection site reactions. These are avoidable using an orally administered CCR2 antagonist.

Diabetes and Insulin Resistance Treatment Regimen

Type 2 diabetes is one of the leading causes of morbidity and mortality in western societies. In the vast majority of patients, the disease is characterized by pancreatic beta-cell dysfunction accompanied by insulin resistance in the liver and in peripheral tissues. Based on the primary mechanisms that are associated with disease, two general classes of oral therapies are available to treat type 2 diabetes: insulin secretagogues (sulfonylureas such as glyburide) and insulin sensitizers (metformin and thiazolidinediones such as rosiglitazone). Combination therapy that addresses both mechanisms has been shown to manage the metabolic defects of this disease and in many instances can be shown to ameliorate the need for exogenous insulin administration. However, with time, insulin resistance often progresses, leading to the need for further insulin supplementation. In addition, a prediabetic state, referred to as the metabolic syndrome, has been demonstrated to be characterized by impaired glucose tolerance, particularly in association with obesity. The majority of patients who develop type 2 diabetes begin by developing insulin resistance, with the hyperglycemia occurring when these patients can no longer sustain the degree of hyperinsulinemia necessary to prevent loss of glucose homeostasis. The onset of the insulin resistance component is highly predictive of disease onset and is associated with an increase in the risk of developing type 2 diabetes, hypertension and coronary heart disease.

One of the strongest correlates of impaired glucose tolerance and of the progression from an insulin resistant state to type 2 diabetes is the presence of central obesity. Most patients with type 2 diabetes are obese and obesity itself is associated with insulin resistance. It is clear that central adiposity is a major risk factor for the development of insulin resistance leading to type 2 diabetes, suggesting that signals from visceral fat contribute to the development of insulin resistant and progression to disease. In addition to the secreted protein factors, obesity induces a cellular inflammatory response in which bone-marrow derived macrophages accumulate in adipose depots, becoming adipose tissue macrophages. Adipose tissue macrophages accumulate in adipose tissue in proportion to measures of adiposity. Tissue infiltrating macrophages are a source of many of the inflammatory cytokines that have been demonstrated to induce insulin resistance in adipocytes.

Adipose tissue produces MCP-1 in proportion to adiposity, suggesting that its activity by signaling through CCR2 also might play an important role in the accumulation of macrophages in adipose tissue. It is unknown whether the MCP-1/CCR2 interaction is directly responsible for monocyte recruitment to adipose tissue, whether reduced recruitment of macrophages to adipose tissue in humans will directly lead to the reduced production of proinflammatory molecules and whether the proinflammatory molecule production is directly linked to insulin resistance.

Patients who demonstrate insulin resistance, either prediabetic (normoglycemic) or diabetic (hyperglycemic), could be treated with a substance that inhibits the expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art). In some embodiments, the substance that inhibits expression and/or activity of CCR2 is a small molecule CCR2 inhibitor (or antagonist). The CCR2 antagonist can be dosed orally q.d. or b.i.d. The patients can be withdrawn from or have a decrease in the dosage of their current therapy and would be maintained on treatment with the CCR2 antagonist. Alternately CCR2 antagonist treatment may be used to supplement their current therapy to enhance its effectiveness or to prevent progression to further insulin dependence.

Advantages of substituting or supplementing traditional agents with CCR2 antagonists are numerous. Such agents may be useful, for example, to preclude progression from a prediabetic, insulin resistant state to a diabetic state. Such agents may reduce or replace the need for the use of insulin sensitizers, with their attendant toxicities. Such agents may also reduce the need for, or prolong the period until, exogenous insulin supplementation is required.

Atherosclerosis Treatment Regimen

Atherosclerosis is a condition characterized by the deposition of fatty substances in arterial walls. Plaque encompasses such deposits of fatty substances, cholesterol, cellular waste products, calcium and other substances that build up in the inner lining of an artery. Plaques can grow large enough to significantly reduce the blood's flow through an artery. However, more significant damage occurs when the plaque becomes unstable and ruptures. Plaques that rupture cause blood clots to form that can block blood flow or break off and travel to other parts of the body. If the clot blocks a blood vessel that feeds the heart, it causes a heart attack. If it blocks a blood vessel that feeds the brain, it causes a stroke. Atherosclerosis is a slow, complex disease that typically starts in childhood and often progresses as people grow older.

A high level of cholesterol in the blood is a major risk factor for coronary heart disease. Based on cholesterol as a primary composition of plaque, the advance of plaque formation has been managed by the reduction of circulating cholesterol or by elevation of cholesterol-carrying high density lipoproteins (HDL). Circulating cholesterol can be reduced, for example, by inhibiting its synthesis in the liver using or by reducing update from food. Such medicaments that act through these mechanism may include medicines that are used to lower high cholesterol levels: bile acid absorbers, lipoprotein synthesis inhibitors, cholesterol synthesis inhibitors and fibric acid derivatives. Circulating HDL can additionally be elevated by administration of, for example, probuchol or high doses of niacin. Therapy that addresses multiple mechanisms has been shown to slow disease progression and progression to plaque rupture.

Atherosclerosis is typically accompanied by a cellular inflammatory response in which bone-marrow derived macrophages accumulate in fatty streaks along the vessel wall, becoming foam cells. Foam cells are a source of many of the inflammatory cytokines that have been demonstrated to induce plaque progression and of the enzymes that can promote plaque destabilization. Atherosclerotic tissue also produces MCP-1, suggesting that its activity by signaling through CCR2 also might play an important role in the accumulation of macrophages as foam cells in plaques. CCR2−/− mice have been demonstrated to have significantly reduced macrophages in fatty streaks generated as a result of high fat diet or genetic alteration in lipid metabolism.

Patients who demonstrate high circulating cholesterol, low HDL, or elevated circulating CRP or present with vessel wall plaque by imaging, or any other evidence of the presence of atherosclerosis could be treated with a substance that inhibits the expression and/or activity of CCR2 including, for example, nucleic acids (e.g., antisense or siRNA molecules), proteins (e.g., anti-CCR2 antibodies), small molecule inhibitors (e.g., the compounds disclosed herein and other chemokine receptor inhibitors known in the art). In some embodiments, the substance that inhibits expression and/or activity of CCR2 is a small molecule CCR2 inhibitor (or antagonist) such as a compound of the invention. The CCR2 antagonist can be dosed orally q.d. or b.i.d at a dose not to exceed about 500 mgs a day. The patients can be withdrawn from or have a decrease in the dosage of their current therapy and would be maintained on treatment with the CCR2 antagonist. Alternately CCR2 antagonist treatment may be used to supplement their current therapy to enhance its effectiveness in, for example, preventing plaque progression, stabilizing plaque that has already formed or inducing plaque regression.

Advantages of substituting or supplementing traditional agents with CCR2 antagonists are numerous. Such agents may be useful, for example, to preclude progression of the plaque to a stage of instability with its associated risk of plaque rupture. Such agents may reduce or replace the need for the use of cholesterol modifying drugs or HDL elevating drugs, with their attendant toxicities including, but not limited to, flushing, liver damage and muscle damage such as myopathy. Such agents may also reduce the need for, or prolong the period until, surgery is required to open the vessel wall or until use of anticoagulants is required to limit damage due to potential plaque rupture.

Labeled Compounds and Assay Methods

Another aspect of the present invention relates to fluorescent dye, spin label, heavy metal or radio-labeled compounds of Formula I that would be useful not only in imaging but also in assays, both in vitro and in vivo, for localizing and quantitating the chemokine receptor in tissue samples, including human, and for identifying chemokine receptor ligands by inhibition binding of a labeled compound. Accordingly, the present invention includes chemokine receptor assays that contain such labeled compounds.

The present invention further includes isotopically-labeled compounds of Formula I. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H, $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro chemokine receptor labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$I, $^{35}$S and $^{82}$Br.

Synthetic methods for incorporating radio-isotopes into organic compounds are applicable to compounds of the invention and are well known in the art. A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the chemokine receptor. Accordingly, the ability of a test compound to compete with the radio-labeled compound for binding to the chemokine receptor directly correlates to its binding affinity.

Kits

The present invention also includes pharmaceutical kits useful, for example, in the treatment or prevention of chemokine-associated diseases which include one or more containers containing a pharmaceutical composition comprising a therapeutically effective amount of a compound of Formula I. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Combination

The compounds or salts of the invention, or mixtures thereof, may be administered in combination with one or more other therapeutic agents, such as a drug. The compound of the present invention or salt thereof may be administered at the same time or different time as one or more other therapeutic agents.

For example, "in combination" includes: simultaneous administration of a combination of compound or salt of the invention and a therapeutic agent to a subject, when such components are formulated together into a single dosage form which releases said components at substantially the same time to said subject; substantially simultaneous administration of a combination of compound or salt of the invention and a therapeutic agent to a subject in need of treatment, when such components are formulated apart from each other into separate dosage forms which are taken at substantially the same time by said subject, whereupon said components are released at substantially the same time to said subject; sequential administration of a combination of compound or salt of the invention and a therapeutic agent to a subject, when such components are formulated apart from each other into separate dosage forms which are taken at consecutive times by said subject with a significant time interval between each administration, whereupon said components are released at substantially different times to said subject; and sequential administration of such combination of compound or salt of the invention and a therapeutic agent to a subject, when such components are formulated together into a single dosage form which releases said components in a controlled manner whereupon they are concurrently, consecutively, and/or over-lappingly administered at the same and/or different times by said subject, where each part may be administered by either the same or different route.

One or more additional pharmaceutical agents such as, for example, antibodies, anti-inflammatory agents, immunosuppressants, chemotherapeutics can be used in combination with the compounds of the present invention for treatment of chemokine receptor-associated diseases, disorders or conditions.

One or more additional pharmaceutical agents such as, for example, anti-viral agents, antibodies, anti-inflammatory agents, insulin secretagogues and sensitizers, serum lipid and lipid-carrier modulating agents, and/or immunosuppressants can be used in combination with the compounds of the present invention for treatment of chemokine receptor-associated diseases, disorders or conditions. The agents can be combined with the present compounds in a single or continuous dosage form, or the agents can be administered simultaneously or sequentially as separate dosage forms.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors and other antiviral drugs.

Suitable antiviral agents contemplated for use in combination with the compounds of the present invention can comprise nucleoside and nucleotide reverse transcriptase inhibitors (NRTIs), non-nucleoside reverse transcriptase inhibitors (NNRTIs), protease inhibitors, entry inhibitors, fusion inhibitors, maturation inhibitors, and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-LAN (also called beta-L-D4C and named beta-L-2',3'-dicleoxy-5-fluoro-cytidene); DAPD, ((−)-beta-D-2,6,-diamino-purine dioxolane); and lodenosine (FddA).

Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4(1H,3H)-pyrimidinedione); and (+)-calanolide A (NSC-675451) and B.

Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549.

Other antiviral agents include hydroxyurea, ribavirin, IL-2, IL-12, pentafuside, enfuvirtide, C-34, the cyclotriazadisulfonamide CADA, PA-457 and Yissum Project No. 11607.

In some embodiments, anti-inflammatory or analgesic agents contemplated for use in combination with the compounds of the present invention can comprise, for example, an opiate agonist, a lipoxygenase inhibitor such as an inhibitor of 5-lipoxygenase, a cyclooxygenase inhibitor such as a cyclooxygenase-2 inhibitor, an interleukin inhibitor such as an interleukin-1 inhibitor, a TNF inhibitor such as infliximab, etanercept, or adalimumab an NNMA antagonist, an inhibitor of nitric oxide or an inhibitor of the synthesis of nitric oxide, a non-steroidal antiinflammatory agent, or a cytokine-suppressing antiinflammatory agent, for example, such as acetaminophen, aspirin, codeine, fentanyl, ibuprofen, indomethacin, ketodolac, morphine, naproxen, phenacetin, piroxicam, a steroidal analgesic, sufentanyl, sunlindac, tenidap, and the like. Similarly, the instant compounds can be administered with a pain reliever; a potentiator such as caffeine, an H2-antagonist, simethicone, aluminum or magnesium hydroxide; a decongestant such as phenylephrine, phenylpropanolamine, pseudophedrine, oxymetazoline, ephinephrine, naphazoline, xylometazoline, propylhexedfine, or levo-desoxyephedrine; an antfitussive such as codeine, hydrocodone, caramiphen, carbetapentane, or dextramethorphan; a diuretic; and a sedating or non-sedating antihistamine.

In some embodiments, pharmaceutical agents contemplated for use in combination with the compounds of the present invention can comprise but are not limited to (a) VLA-4 antagonists such as those described in U.S. Pat. No. 5,510,332, W095/15973, W096/01644, W096/06108, W096/20216, W096/229661, W096/31206, W096/4078, W097/030941, W097/022897 WO 98/426567 W098/53814, W098/53817, W098/538185, W098/54207, and W098/58902; (b) steroids such as beclornethasone, methylpi-ednisolone, betarnethasone, prednisone, dexamethasone, and hydrocortisone; (c) immunosuppressants such as cyclosporin, tacrolimus, raparnycin and other FK506 type immunosuppressants; (d) antihistamines (HI-histamine antagonists) such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilarnine, asternizole, terfenadine, loratadine, cetirizine, fexofenadine, desearboethoxyloratadine, and the like; (e) non-steroidal anti-asthmatics such as terbutaline, metaproterenol, fenoterol, isoethaiine, albuterol, bitolterol, pirbuterol, theophylline, cromolyn sodium, atropine, ipratropium bromide, leukotriene antagonists (e.g., zafirlukast, montelukast, pranlukast, iralukast, pobilukast, SKB-106, 203), leukotriene biosynthesis inhibitors (e.g., zileuton, BAY-1005); (f) nonsteroidal antiinflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (e.g., indomethacin, acernetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenarnic acid derivatives (flufenarnic acid, meclofenamic acid, rnefenamic acid, niflumic acid and tolfenarnic acid), biphenylcarboxylic acid derivatives (diflunisal and flufenisal), oxicarns (isoxicarn, piroxicam, sudoxicam and tenoxican), salicylates (acetyl salicylic acid, sulfasalazine) and the pyrazolones (apazone, bezpiperylon, feprazone, mofebutazone, oxyphenbutazone, phenylbutazone); (g) cyclooxygenase-2 (COX-2) inhibitors; (h) inhibitors of phosphodiesterase type IV (PDE-IV); (i) other antagonists of the chemokine receptors, especially CXCR-4, CCR1, CCR2, CCR3 and CCR5; (j) cholesterol lowering agents such as HMG-CoA reductase inhibitors (lovastatin, sirrivastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (k) anti-inflammatory biologic agents such as anti-TNF therapies, anti-IL-1 receptor, CTLA-4Ig, anti-CD20, and anti-VLA4 antibodies; (I) anti-diabetic agents such as insulin, sulfonylureas, biguanides (metformin), U.-glucosidase inhibitors (acarbose) and orlitazones (troglitazone and pioglitazone); (m) preparations of interferon beta (interferon beta-lo., interferon beta-1 P); (n) other compounds such as aminosalicylic acids, antimetabolites such as azathioprine and 6-mercaptopurine, and cytotoxic cancer chemotherapeutic agents. The weight ratio of the compound of the compound of the present invention to the second active ingredient may be varied and will depend upon the effective dose of each ingredient.

For example, a CCR2 and/or CCR5 antagonist can be used in combination with an anti-inflammatory pharmaceutical agent in the treatment of inflammation, metabolic disease, autoimmune disease, pain, cancer or viral infection to improve the treatment response as compared to the response to the therapeutic agent alone, without exacerbation of its toxic effects. Additive or synergistic effects are desirable outcomes of combining a CCR2 and/or CCR5 antagonist of the present invention with an additional agent. Furthermore, resistance of cancer cells to agents such as dexamethasone can be reversible upon treatment with a CCR2 and/or CCR5 antagonist of the present invention.

F. Use in the Preparation of a Composition or Medicament

In one embodiment, the present invention comprises methods for the preparation of a composition or medicament comprising the compounds or salts of the present invention for use in treating condition mediated by chemokine receptors.

In another embodiment, the invention comprises the use of one or more compounds or salts of the present invention in the preparation of a composition or a medicament for inflammation, inflammatory disease, immune disorder, pain, cancer, or viral infection.

The present invention also includes the use of one or more compounds or salts of the present invention for preparation of a composition or a medicament for treating one or more conditions detailed in the Methods section.

G. Schemes

The compounds of the present invention may be prepared using the methods illustrated in the general synthetic schemes and experimental procedures detailed below. The reactions of the synthetic methods herein are carried out in suitable solvents which may be readily selected by one skilled in the art of organic synthesis, said suitable solvents generally being any solvent which is substantially nonreactive with the starting materials (reactants), the intermediates, or products at the temperatures at which the reactions are carried out. A given reaction may be carried out in one solvent or a mixture of more than one solvent. Depending on the particular reaction step, suitable solvents for a particular reaction step may be selected.

Preparation of compounds of the invention can involve the protection and deprotection of various chemical groups. The need for protection and deprotection, and the selection of appropriate protecting groups can be readily determined by one skilled in the art. The chemistry of protecting groups can be found, for example, in T. W. Greene and P. G. M. Wuts, *Protective Groups in Organic Synthesis,* 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The starting materials used herein are either commercially available or may be prepared by routine synthetic methods.

The general synthetic schemes are presented for purposes of illustration and are not intended to be limiting.

Scheme 1 Preparation of Examples 1-23

Scheme 1

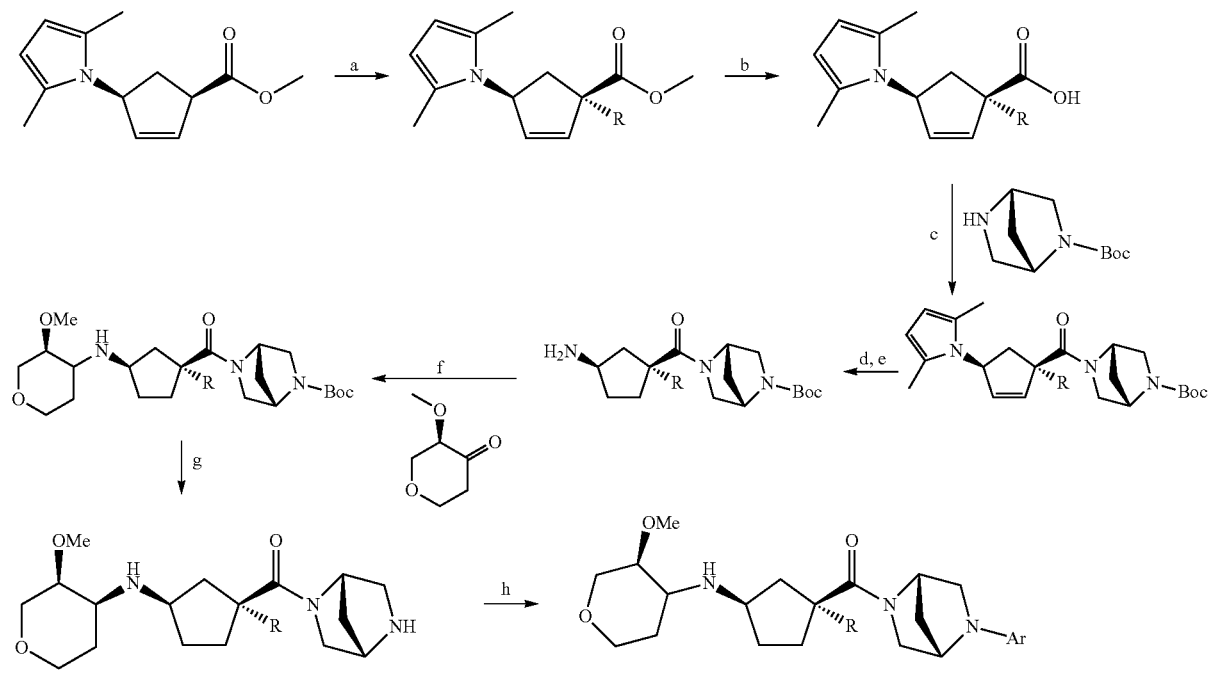

n = 1 or 2
a) LDA or NaHDMS, R—X, THF; b) 2.5N NaOH, MeOH; c) 2.2.1-Boc, DMF, DIPEA, Bop; d) H₂NOH•HCl, MeOH; NH₂OH(aq); e) 5% Pd/C, MeOH, 50 psi H₂; f) pyranone, DCM, Na(OAc)₃BH; g) 4N HCl/1,4-dioxane; h) cond a or cond b or cond c or cond d
cond a = Ar—X, DMSO, Et₃N, 120° C.
cond b = Ar—X, Cs₂CO₃, XantPhos, Pd₂(dba)₃, dioxane, DMSO
cond c = Ar—X, 1,4-dioxane, Et₃N, 100° C.
cond d = Ar—X, NaOtBu, catalyst 1, Pd₂(dba)₃, dioxane, DMSO

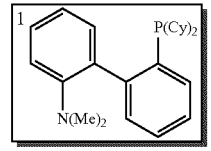

Example 1

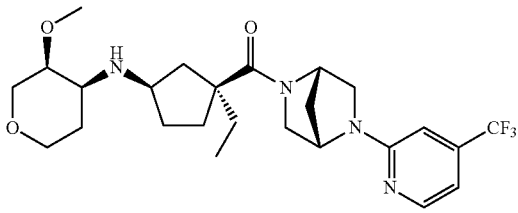

1,5-anhydro-2,3-dideoxy-3-{[(1R,3S)-3-ethyl-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol

Step 1: Preparation of methyl (1R,4S)-4-(2,5-dimethyl-1H-pyrrol-1-yl)-1-ethylcyclopent-2-ene-1-carboxylate

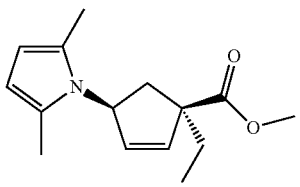

A –40° C. solution of 2M (in THF/ethylbenzene/heptane) LDA (68 ml, 138 mmol) in tetrahydrofuran (120 ml) was treated with methyl (1R,4S)-4-(2,5-dimethyl-1H-pyrrol-1-yl)cyclopent-2-ene-1-carboxylate (14.02 g, 63.9 mmol) while keeping the temperature less than –33° C. The cold reaction was stirred for 40 minutes and then a solution of ethyl iodide (13.63 g, 87.4 mmol) in tetrahydrofuran (5 ml) was added slowly while keeping the temperature less than –33° C. The reaction was stirred with the cold bath in place for four hours and allowed to slowly warm. The reaction was poured into NH4Cl soln (300 ml), then extracted with ethyl acetate (2×200 ml), washed with brine dried over MgSO₄, and concentrated under reduced pressure. The resulting brown oil was passed through a column of silica gel with 10% ethyl acetate/hexanes to give methyl (1R,4S)-4-(2,5-dimethyl-1H-pyrrol-1-yl)-1-ethylcyclopent-2-ene-1-carboxylate as a brown oil (12.96 g, 82%).

$^1$H NMR (400 MHz, CDCl₃) δ ppm 5.98-5.96 (1H), 5.93-5.91 (1H), 5.73 (2H), 5.30-5.24 (1H), 3.71 (3H), 2.45-2.34 (2H), 2.19 (6H), 1.79-1.73 (2H), 0.91-0.87 (3H).

Step 2: Preparation of (1R,4S)-4-(2,5-dimethyl-1H-pyrrol-1-yl)-1-ethylcyclopent-2-ene-1-carboxylic acid

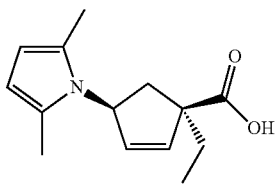

A solution of methyl (1R,4S)-4-(2,5-dimethyl-1H-pyrrol-1-yl)-1-ethylcyclopent-2-ene-1-carboxylate (12.94 g, 52.3 mmol) in methanol (100 ml) was treated with 2.5N NaOH (30 ml, 75.0 mmol) and stirred at room temperature. After 15 hours more 2.5N NaOH (10 ml, 25.0 mmol) was added and the reaction was stirred for an additional four days. The methanol was removed under reduced pressure and the residue partitioned between diethyl ether and water. The layers were separated and the aqueous was acidified with 4N HCl, extracted twice with ethyl acetate, washed with brine, dried over MgSO₄, and concentrated under reduced pressure to give (1R,4S)-4-(2,5-dimethyl-1H-pyrrol-1-yl)-1-ethylcyclopent-2-ene-1-carboxylic acid as a brown oil (11.83 g, 97%).

$^1$H NMR (400 MHz, CDCl₃) δ ppm 5.98-5.96 (2H), 5.73 (2H), 5.30-5.26 (1H), 2.47-2.35 (2H), 2.20 (6H), 1.82-1.77 (2H), 0.96-0.92 (3H).

Step 3: Preparation of tert-butyl (1S,4S)-5-{[(1R,4S)-4-(2,5-dimethyl-1H-pyrrol-1-yl)-1-ethylcyclopent-2-en-1-yl]carbonyl}-2,5-diazabicyclo[2.2.1]heptane-2-carboxylate

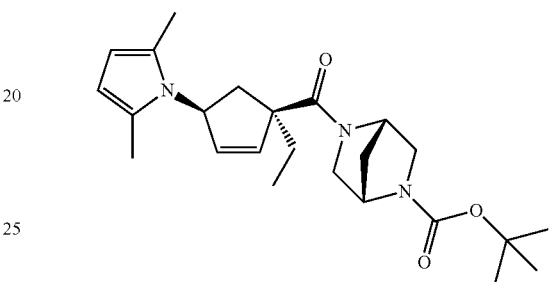

BOP=benzotriazol-1-yloxytris(dimethylamino)phosphonium hexafluorophosphate

A solution of (1R,4S)-4-(2,5-dimethyl-1H-pyrrol-1-yl)-1-ethylcyclopent-2-ene-1-carboxylic acid (6.59 g, 28.2 mmol) in DMF (40 ml) was treated with N,N-diisopropylethylamine (14.7 ml, 84.4 mmol) and BOP (14.51 g, 32.8 mmol) and stirred under nitrogen at room temperature for 20 minutes. A solution of (1S,4S)-2-BOC-2,5-diazabicyclo[2.2.1]heptane (5.66 g, 28.5 mmol) in DMF (5 ml) was added and the reaction was stirred for 24 hours. The reaction was diluted with ethyl acetate (100 ml) and washed with 60% saturated NaHCO₃ (125 ml). The aqueous layer was extracted with ethyl acetate. The organic layers were combined, washed with brine, dried over MgSO₄ and concentrated under reduced pressure to give a brown oil (21.25 g). The oil was passed through a column of silica gel with 50% ethyl acetate/hexanes to give tert-butyl (1S,4S)-5-{[(1R,4S)-4-(2,5-dimethyl-1H-pyrrol-1-yl)-1-ethylcyclopent-2-en-1-yl]carbonyl}-2,5-diazabicyclo[2.2.1]heptane-2-carboxylate as a white foam (8.14 g, 70%). $^1$H NMR (400 MHz, CDCl₃) δ ppm 6.24-6.17 (1H), 5.90-5.86 (1H), 5.73-5.68 (2H), 5.34-5.22 (1H), 5.02-4.41 (2H), 3.71-3.24 (4H), 2.61-2.39 (1H), 2.27-2.16 (7H), 1.89-1.59 (4H), 1.49-1.32 (9H), 0.95-0.85 (3H).

Step 4: Preparation of tert-butyl (1S,4S)-5-{[(1R,4S)-4-amino-1-ethylcyclopent-2-en-1-yl]carbonyl}-2,5-diazabicyclo[2.2.1]heptane-2-carboxylate

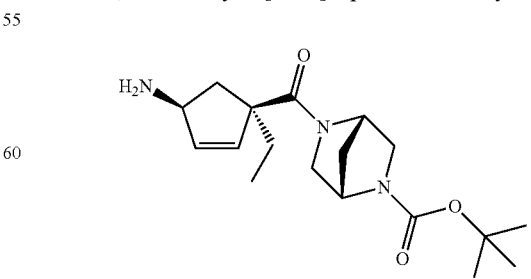

A solution of tert-butyl (1S,4S)-5-{[(1R,4S)-4-(2,5-dimethyl-1H-pyrrol-1-yl)-1-ethylcyclopent-2-en-1-yl]carbonyl}-2,5-diazabicyclo[2.2.1]heptane-2-carboxylate (2.61 g, 6.3 mmol) in methanol (40 ml) and water (10 ml) was treated with hydroxylamine hydrochloride (2.73 g, 39.1 mmol) and 50 weight % solution of hydroxylamine (2.4 ml, 39.2 mmol). The reaction was stirred under nitrogen and heated to 68° C. for 38.5 hours. The reaction was cooled to room temperature, diluted with water, and made basic (pH~11) by the addition of 2.5N NaOH. The reaction mixture was extracted with ethyl acetate (3×100 ml), washed with brine, dried over MgSO$_4$ and concentrated under reduced pressure to give a crude mixture of tert-butyl (1S,4S)-5-{[(1R,4S)-4-amino-1-ethylcyclopent-2-en-1-yl]carbonyl}-2,5-diazabicyclo[2.2.1]heptane-2-carboxylate as a yellow oil (2.68 g, theoretical yield 2.12 g) which was used without further purification in the next step.

Step 5: Preparation of tert-butyl (1S,4S)-5-{[(1S,3R)-3-amino-1-ethylcyclopentyl]carbonyl}-2,5-diazabicyclo[2.2.1]heptane-2-carboxylate

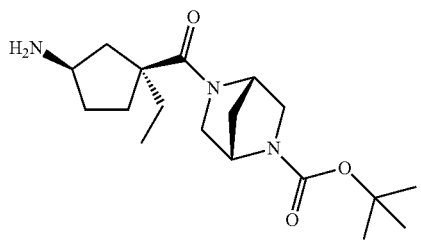

A mixture of tert-butyl (1S,4S)-5-{[(1R,4S)-4-amino-1-ethylcyclopent-2-en-1-yl]carbonyl}-2,5-diazabicyclo[2.2.1]heptane-2-carboxylate (2.12 g, 6.32 mmol) and 5% palladium on carbon in methanol (35 ml) was stirred at room temperature under 48 psi of hydrogen for 21 hours. The reaction was filtered through celite and the filter cake washed with methanol. The filtrate and washings were concentrated under reduced pressure to give tert-butyl (1S,4S)-5-{[(1S,3R)-3-amino-1-ethylcyclopentyl]carbonyl}-2,5-diazabicyclo[2.2.1]heptane-2-carboxylate as a brown oil/foam (2.46 g, theoretical yield 2.13 g) which was used without further purification in the next step.

Step 6: Preparation of (1S,4S)-tert-butyl 5-((1S,3R)-1-ethyl-3-((3S,4R)-3-methoxy-tetrahydro-2H-pyran-4-ylamino)cyclopentanecarbonyl)-2,5-diaza-bicyclo[2.2.1]heptane-2-carboxylate

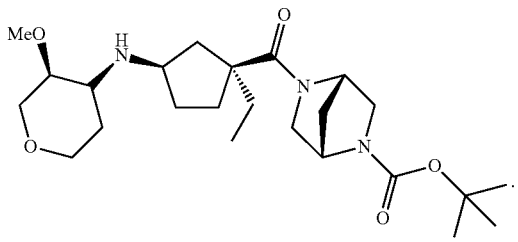

A 0° C. solution of tert-butyl (1S,4S)-5-{[(1S,3R)-3-amino-1-ethylcyclopentyl]carbonyl}-2,5-diazabicyclo[2.2.1]heptane-2-carboxylate (1.58 g, 4.7 mmol) in dichloromethane (25 ml) was treated with sodium triacetoxyborohydride (2.36 g, 11.1 mmol) and 3R)-3-meth- oxytetrahydro-4H-pyran-4-one (0.76 g, 7.6 mmol). The reaction was stirred under nitrogen at 0° C. for 30 minutes then allowed to warm to room temperature and stirred for 15 hours. The reaction was treated with 2.5N NaOH (10 mL) and stirred for 10 minutes. The reaction was diluted with water and the layers separated. The aqueous layer was extracted twice with ethyl acetate. The dichloromethane layer was concentrated under reduced pressure and partitioned between ethyl acetate and water. The organic layers were combined, washed with brine, dried over MgSO$_4$, concentrated under reduced pressure and purified with the Biotage (0-100% methanol/ethyl acetate, 15 column volumes) to give the desired product, 1,5-anhydro-3-{[(1R,3S)-3-{[(1S,4S)-5-(tert-butoxycarbonyl)-2,5-diazabicyclo[2.2.1]hept-2-yl]carbonyl}-3-ethylcyclopentyl]amino}-2,3-dideoxy-4-O-methyl-D-erythro-pentitol. LC/MS (M+H)=452.3124 exp, 452.3135 obs; $^1$H NMR (400 MHz, CDCl$_3$) δ ppm 4.94-4.41 (2H), 4.11-4.04 (1H), 3.97-3.91 (1H), 3.53-3.18 (11H), 2.83-2.75 (1H), 2.60-2.30 (1H), 2.03-1.55 (10H), 1.48-1.37 (11H), 0.85-0.78 (3H)

Step 7: Preparation of (1S,4S)-2,5-diaza-bicyclo[2.2.1]heptan-2-yl((1S,3R)-1-ethyl-3-((3S,4R)-3-methoxy-tetrahydro-2H-pyran-4-ylamino)cyclopentyl)methanone

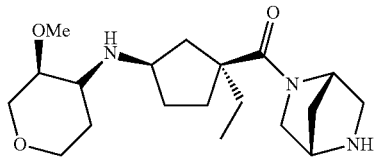

To a solution of (1S,4S)-tert-butyl 5-((1S,3R)-1-ethyl-3-((3S,4R)-3-methoxy-tetrahydro-2H-pyran-4-ylamino)cyclopentanecarbonyl)-2,5-diaza-bicyclo[2.2.1]heptane-2-carboxylate (1.22 g, 2.89 mmol) in 1,4-dioxane (15 ml) was added 4N HCl/1,4-dioxane (15 ml). The reaction was stirred at room temperature for 18 hours. The liquid was decanted leaving a gummy solid which was dissolved in methanol and concentrated under reduced pressure. The residue was dissolved in methylene chloride and concentrated to give the product HCl salt of as a brown foam (1.23 g, theoretical yield 1.03 g) which was used in the next step without further purification.

Step 8: Preparation of 1,5-anhydro-2,3-dideoxy-3-{[(1R,3S)-3-ethyl-3-({(1S,4S)-5-[4-(trifluoromethyl)pyridin-2-yl]-2,5-diazabicyclo[2.2.1]hept-2 yl}carbonyl)cyclopentyl]amino}-4-O-methyl-D-erythro-pentitol

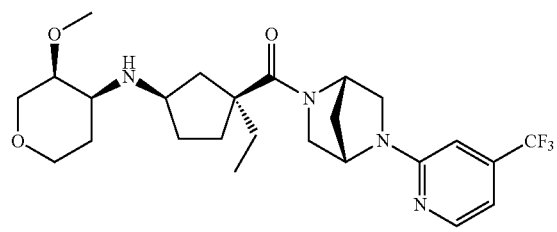

To a solution of HCl salt of (1S,4S)-2,5-diaza-bicyclo[2.2.1]heptan-2-yl((1S,3R)-1-ethyl-3-((3S,4R)-3-methoxy-tetrahydro-2H-pyran-4-ylamino)cyclopentyl)methanone (118 mg, 0.33 mmol) in DMSO (2 ml) was added triethylamine (0.15 ml, 1.08 mmol) and the 2-chloro-4-(trifluoromethyl)pyridine (183 mg, 1.01 mmol). The reaction was heated to 120° C. for 15 hours. The reaction was cooled to room temperature, and added to stirring ice water. The mixture was extracted with ethyl acetate (3×). The combined organics were washed with brine, dried over MgSO$_4$ concentrated under reduced pressure and purified with the Biotage (0-100% methanol/ethyl acetate, 15 column volumes) to give the product as a brown foam (40 mg 26%). LC/MS (M+H)=497.2739 exp, 497.2884 obs; $^1$H NMR (400 MHz, CDCl$_3$) δ ppm 8.25-8.24 (1H), 6.75-6.74 (1H), 6.51-6.45 (1H), 5.13-4.76 (2H), 4.10-4.03 (1H), 3.95-3.90 (1H), 3.72-3.16 (11H), 2.82-2.67 (1H), 2.58-2.36 (1H), 2.06-1.36 (12H), 0.86-0.67 (3H)

Example 2

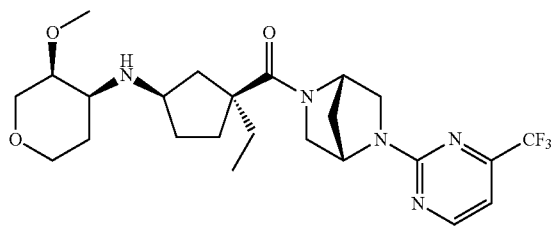

1,5-anhydro-2,3-dideoxy-3-{[(1R,3S)-3-ethyl-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol Prepared as described in example 1 using 2-chloro-4-(trifluoromethyl)pyrimidine in place of 2-chloro-4-(trifluoromethyl)pyridine and modifying step 8 as follows. The HCl salt of amine (91 mg, 0.25 mmol) was placed in flask with 1,4-dioxane (3 ml). Triethylamine (0.12 ml, 0.86 mmol) was added as well as 2-chloro-4-(trifluoromethyl)pyrimidine (148 mg, 0.81 mmol). DMSO (0.3 ml) was added for solubility and the reaction was heated to 100° C. for 20 hours. The reaction was cooled to room temperature and concentrated under reduced pressure. The residue was partitioned between ethyl acetate and water. The aqueous layer was extracted with ethyl acetate and the combined organics were washed with brine, dried over MgSO$_4$, concentrated under reduced pressure and purified with the Biotage (0-100% methanol/ethyl acetate 15 column volumes) to give the product as a brown foam (43 mg, 58%). LC/MS (M+H)=498.2692 exp, 498.2799 obs; $^1$H NMR (400 MHz, CDCl$_3$) δ ppm 8.48-8.47 (1H), 6.80-6.78 (1H), 5.16-4.71 (2H), 4.09-4.00 (1H), 3.93-3.86 (1H), 3.70-3.51 (3H), 3.45-3.13 (8H), 2.85-2.66 (1H), 2.60-2.33 (1H), 2.06-1.35 (12H), 0.87-0.66 (3H)

Example 3

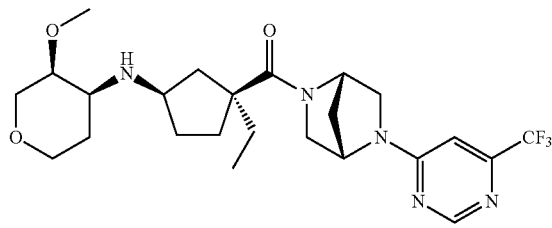

1,5-anhydro-2,3-dideoxy-3-{[(1R,3S)-3-ethyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol Prepared as described in example 1 using 4-chloro-6-(trifluoromethyl)pyrimidine in place of 2-chloro-4-(trifluoromethyl)pyridine and modifying step 8 as follows. The HCl salt of amine (227 mg, 0.63 mmol) was placed in a flask with 1,4-dioxane (3 ml). To the stirred solution was added Xantphos (26 mg, 0.045 mmol), Pd$_2$(dba)$_3$ (39 mg, 0.042 mmol), Cs$_2$CO$_3$ (258 mg, 0.79 mmol), and 4-chloro-6-(trifluoromethyl)pyrimidine (261 mg, 1.43 mmol) dissolved in 1,4-dioxane (1 ml). DMSO (0.3 ml) was added for solubility and the reaction was heated to 100° C. for 15 hours. The reaction was allowed to cool to room temperature and filtered through celite. The filtrate was concentrated under reduced pressure and purified with the Biotage (0-100% methanol/ethyl acetate 15 column volumes) to give the product as a brown foam (93 mg, 37%). LC/MS (M+H)=498.2692 exp, 498.2853 obs; $^1$H NMR (400 MHz, CDCl$_3$) δ ppm 8.63 (1H), 6.76-6.42 (1H), 5.31-4.54 (2H), 4.12-4.03 (1H), 3.96-3.85 (1H), 3.72-3.15 (11H), 2.80-2.66 (1H), 2.57-2.35 (1H), 2.09-1.33 (12H), 0.88-0.64 (3H)

Example 4

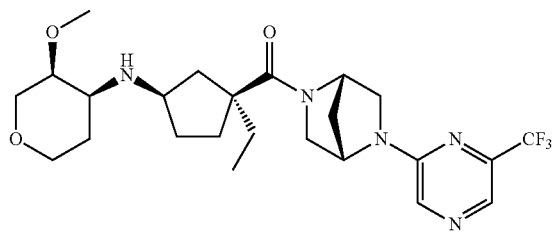

1,5-anhydro-2,3-dideoxy-3-{[(1R,3S)-3-ethyl-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol Prepared as described in example 3 using 2-iodo-6-(trifluoromethyl)pyrazine in place of 4-chloro-6-(trifluoromethyl)pyrimidine in step 8. LC/MS (M+H)=498.2692 exp, 498.2867 obs; $^1$H NMR (400 MHz, CDCl$_3$) δ ppm 8.16 (1H), 8.05-7.97 (1H), 5.18-4.78 (2H), 4.12-4.02 (1H), 3.99-3.88 (1H), 3.74-3.14 (11H), 2.82-2.66 (1H), 2.61-2.36 (1H), 2.07-1.36 (12H), 0.86-0.68 (3H)

Example 5

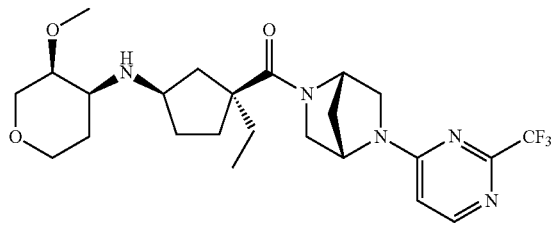

1,5-anhydro-2,3-dideoxy-3-{[(1R,3S)-3-ethyl-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol Prepared as described in example 3 using 4-chloro-2-(trifluoromethyl)pyrimidine in place of 4-chloro-6-(trifluoromethyl)pyrimidine in step 8. LC/MS (M+H)=498.2692 exp, 498.2839 obs; $^1$H NMR (400 MHz, CDCl$_3$) δ ppm 8.24-8.22 (1H), 6.54-6.19 (1H), 5.31-4.50 (2H), 4.09-4.00 (1H), 3.90-3.85 (1H), 3.72-3.17 (11H), 2.78-2.62 (1H), 2.55-2.35 (1H), 2.04-1.32 (12H), 0.85-0.63 (3H)

Example 6

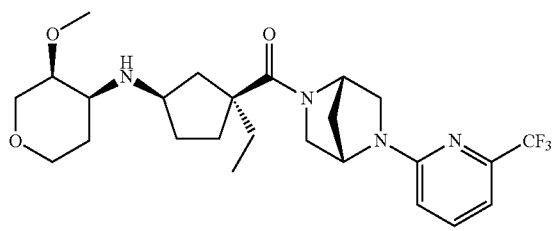

1,5-anhydro-2,3-dideoxy-3-{[(1R,3S)-3-ethyl-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 1 using 2-chloro-6-(trifluoromethyl)pyridine in place of 4-chloro-6-(trifluoromethyl)pyrimidine in step 8. LC/MS (M+H)=497.2739 exp, 497.2641 obs; $^1$H NMR (400 MHz, CDCl$_3$) δ ppm 7.56-7.52 (1H), 6.92-6.90 (1H), 6.52-6.41 (1H), 5.11-4.73 (2H), 4.08-4.03 (1H), 3.95-3.89 (1H), 3.73-3.13 (11H), 2.82-2.64 (1H), 2.58-2.35 (1H), 2.05-1.35 (12H), 0.85-0.66 (3H)

Example 7

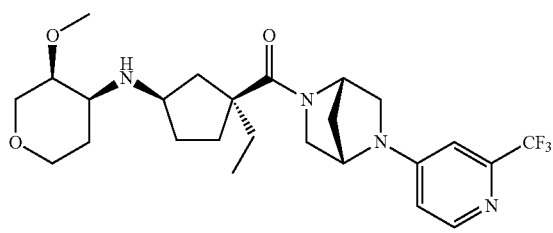

1,5-anhydro-2,3-dideoxy-3-{[(1R,3S)-3-ethyl-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol Prepared as described in example 3 using 4-iodo-2-(trifluoromethyl)pyridine in place of 4-chloro-6-(trifluoromethyl)pyrimidine in step 8. LC/MS (M+H)=497.2739 exp, 497.2878 obs; $^1$H NMR (400 MHz, CDCl$_3$) δ ppm 8.30-8.28 (1H), 6.76-6.69 (1H), 6.52-6.44 (1H), 5.16-4.79 (1H), 4.54 (1H), 4.07-4.04 (1H), 3.93-3.90 (1H), 3.68-3.14 (11H), 2.81-2.64 (1H), 2.59-2.31 (1H), 2.08-1.35 (12H), 0.87-0.65 (3H)

Example 8

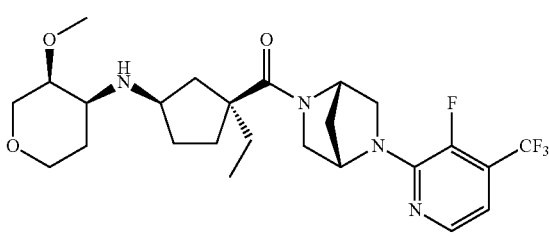

1,5-anhydro-2,3-dideoxy-3-{[(1R,3S)-3-ethyl-3-({(1S,4S)-5-[3-fluoro-4-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 3 using 2-chloro-3-fluoro-4-(trifluoromethyl)pyridine in place of 4-chloro-6-(trifluoromethyl)pyrimidine in step 8. LC/MS (M+H)=515.2645 exp, 515.2772 obs; $^1$H NMR (400 MHz, CDCl$_3$) δ ppm 8.00-7.99 (1H), 6.75-6.73 (1H), 5.09-4.69 (2H), 4.09-4.04 (1H), 3.96-3.90 (1H), 3.86-3.78 (1H), 3.69-3.53 (3H), 3.42-3.17 (7H), 2.81-2.68 (1H), 2.57-2.38 (1H), 2.04-1.36 (12H), 0.88-0.69 (3H)

Example 9

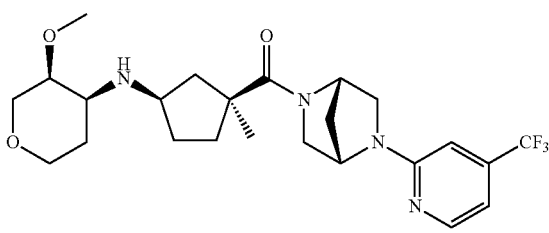

1,5-anhydro-2,3-dideoxy-3-{[(1R,3S)-3-methyl-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 1 using methyl iodide in place of ethyl iodide in step 1. LC/MS (M+H)=483.2583 exp, 483.2543 obs; $^1$H NMR (400 MHz, CDCl$_3$) δ ppm 8.25-8.24 (1H), 6.75-6.74 (1H), 6.51-6.45 (1H), 5.09-4.76 (2H), 4.09-4.03 (1H), 3.96-3.90 (1H), 3.70-3.23 (11H), 2.81-2.65 (1H), 2.53-2.27 (1H), 2.07-1.02 (13H); HRMS m/z 483.2543 (calcd for M+H, 483.2583).

Example 10

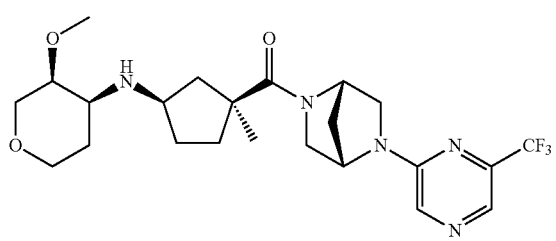

1,5-anhydro-2,3-dideoxy-3-{[(1R,3S)-3-methyl-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol Prepared as described in example 3 using methyl iodide in place of ethyl iodide in step 1 and 2-iodo-6-(trifluoromethyl)pyrazine in place of 4-chloro-6-(trifluoromethyl)pyrimidine in step 8. LC/MS (M+H)=483.2583 exp, 483.2543 obs; $^1$H NMR (400 MHz, CDCl$_3$) δ ppm 8.25-8.24 (1H), 6.75-6.74 (1H), 6.51-6.45 (1H), 5.09-4.76 (2H), 4.09-4.03 (1H), 3.96-3.90 (1H), 3.70-3.23 (11H), 2.81-2.65 (1H), 2.53-2.27 (1H), 2.07-1.02 (13H)

Example 11

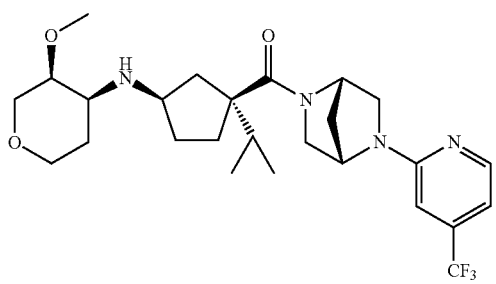

1,5-anhydro-2,3-dideoxy-3-{[(1R,3S)-3-isopropyl-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 1 starting with (1S,4S)-4-(2,5-dimethyl-1H-pyrrol-1-yl)-1-isopropylcyclopent-2-ene-1-carboxylic acid and skipping steps 1 and 2. LC/MS (M+H)=511.2896 exp, 511.3218 obs; $^1$H NMR (400 MHz, CDCl$_3$) δ ppm 8.23-8.22 (1H), 6.73-6.72 (1H), 6.49-6.44 (1H), 5.11-4.73 (2H), 4.06-4.03 (1H), 3.92-3.89 (1H), 3.67-3.52 (2H), 3.44-3.22 (8H), 3.12-3.03 (1H), 2.80-2.61 (1H), 2.51-2.40 (1H), 2.09-1.72 (6H), 1.68-1.42 (4H), 1.35-1.25 (1H), 0.92-0.75 (6H)

Example 12

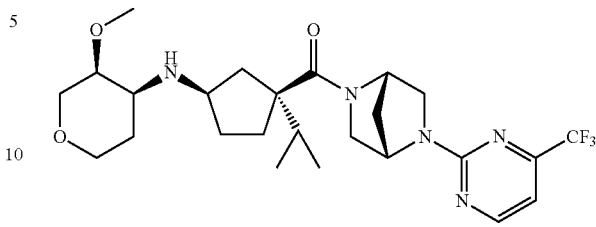

1,5-anhydro-2,3-dideoxy-3-{[(1R,3S)-3-isopropyl-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol Prepared as described in example 2 starting with (1S,4S)-4-(2,5-dimethyl-1H-pyrrol-1-yl)-1-isopropylcyclopent-2-ene-1-carboxylic acid and skipping steps 1 and 2. LC/MS (M+H)=512.2849 exp, 512.2827 obs; $^1$H NMR (400 MHz, CDCl$_3$) δ ppm 8.45-8.44 (1H), 6.77-6.76 (1H), 5.09-4.71 (2H), 4.07-4.01 (1H), 3.92-3.87 (1H), 3.67-3.51 (3H), 3.42-3.23 (7H), 3.15-3.08 (1H), 2.83-2.76 (1H), 2.58-2.33 (2H), 2.11-1.56 (8H), 1.51-1.42 (1H), 1.38-1.30 (1H), 0.91-0.74 (6H)

Example 13

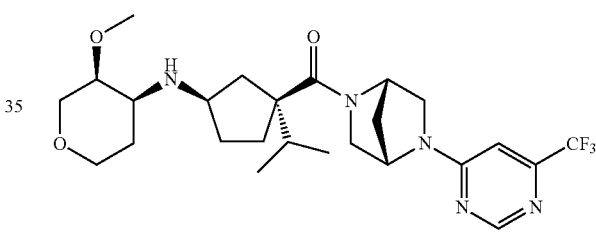

1,5-anhydro-2,3-dideoxy-3-{[(1R,3S)-3-isopropyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2. LC/MS (M+H)=512.2849 exp, 512.3227 obs; $^1$H NMR (400 MHz, CDCl$_3$) δ ppm 8.61 (1H), 6.73-6.44 (1H), 5.25-4.52 (2H), 4.05-4.01 (1H), 3.91-3.86 (1H), 3.68-3.46 (2H), 3.38-3.17 (8H), 3.10-3.03 (1H), 2.76-2.63 (1H), 2.48-2.37 (1H), 2.07-1.39 (10H), 1.34-1.23 (1H), 0.90-0.74 (6H)

Example 14

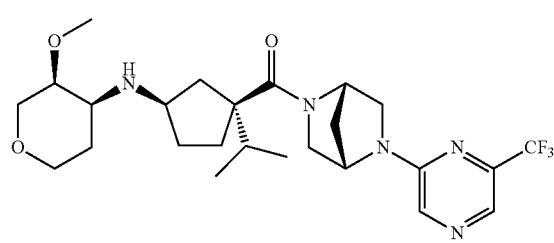

1,5-anhydro-2,3-dideoxy-3-{[(1R,3S)-3-isopropyl-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 2-iodo-6-(trifluoromethyl)pyrazine in place of 4-chloro-6-(trifluoromethyl)pyrimidine in step 8. LC/MS (M+H)= 512.2849 exp, 512.3221 obs; $^1$H NMR (400 MHz, CDCl$_3$) δ ppm 8.12 (1H), 8.01-7.97 (1H), 5.14-4.75 (2H), 4.05-4.01 (1H), 3.90-3.87 (1H), 3.67-3.56 (211), 3.44-3.20 (8H), 3.11-3.02 (1H), 2.78-2.60 (1H), 2.48-2.39 (1H), 2.10-1.86 (4H), 1.82-1.71 (2H), 1.68-1.53 (2H), 1.50-1.38 (2H), 1.33-1.24 (1H), 0.91-0.74 (6H)

Example 15

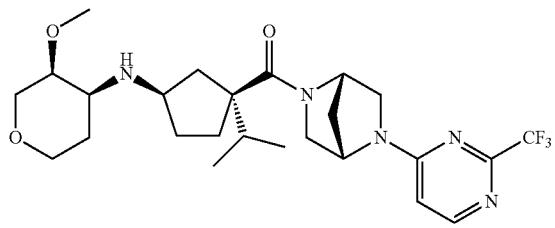

1,5-anhydro-2,3-dideoxy-3-{[(1R,3S)-3-isopropyl-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 4-chloro-2-(trifluoromethyl)pyrimidine in place of 4-chloro-6-(trifluoromethyl)pyrimidine in step 8. LC/MS (M+H)= 512.2849 exp, 512.2891 obs; $^1$H NMR (400 MHz, CDCl$_3$) δ ppm 8.25-8.24 (1H), 6.52-6.23 (1H), 5.30-4.47 (2H), 4.05-4.02 (1H), 3.91-3.88 (1H), 3.70-3.54 (2H), 3.52-3.18 (8H), 3.12-3.03 (1H), 2.78-2.61 (1H), 2.49-2.39 (1H), 2.08-1.85 (5H), 1.82-1.72 (1H), 1.68-1.41 (4H), 1.35-1.24 (1H), 0.93-0.75 (6H)

Example 16

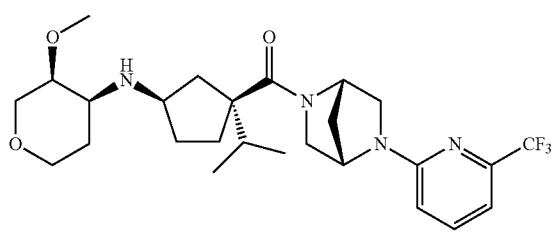

1,5-anhydro-2,3-dideoxy-3-{[(1R,3S)-3-isopropyl-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 1 starting with (1S,4S)-4-(2,5-dimethyl-1H-pyrrol-1-yl)-1-isopropylcyclopent-2-ene-1-carboxylic acid and skipping steps 1 and 2 and using 2-chloro-6-(trifluoromethyl)pyridine in place of 2-chloro-4-(trifluoromethyl)pyridine in step 8. LC/MS (M+H)= 511.2896 exp, 511.2856 obs; $^1$H NMR (400 MHz, CDCl$_3$) δ ppm 7.54-7.50 (1H), 6.90-6.88 (1H), 6.50-6.41 (1H), 5.08-4.70 (2H), 4.08-3.99 (1H), 3.94-3.87 (1H), 3.73-3.46 (2H), 3.46-3.13 (8H), 3.13-2.97 (1H), 2.81-2.58 (1H), 2.52-2.38 (1H), 2.10-1.70 (5H), 1.70-1.40 (5H), 1.36-1.25 (1H), 0.94-0.73 (6H) 0.75 (6H)

Example 17

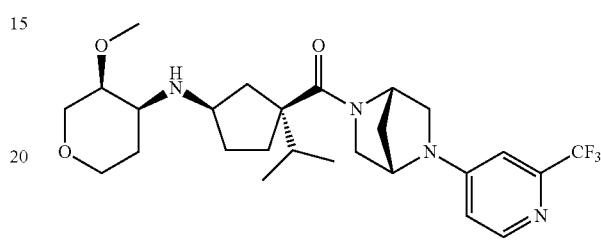

1,5-anhydro-2,3-dideoxy-3-{[(1R,3S)-3-isopropyl-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 4-iodo-2-(trifluoromethyl)pyridine in place of 2-chloro-4-(trifluoromethyl)pyridine in step 8. LC/MS (M+H)= 511.2896 exp, 511.2958 obs; $^1$H NMR (400 MHz, CDCl$_3$) δ ppm 8.27-8.26 (1H), 6.72-6.69 (1H), 6.49-6.44 (1H), 5.09-4.75 (1H), 4.52 (1H), 4.05-4.02 (1H), 3.91-3.88 (1H), 3.65-3.50 (3H), 3.41-3.03 (8H), 2.78-2.55 (1H), 2.49-2.35 (1H), 2.08-1.87 (4H), 1.84-1.72 (2H), 1.68-1.53 (2H), 1.51-1.38 (2H), 1.34-1.26 (1H), 0.92-0.75 (6H)

Example 18

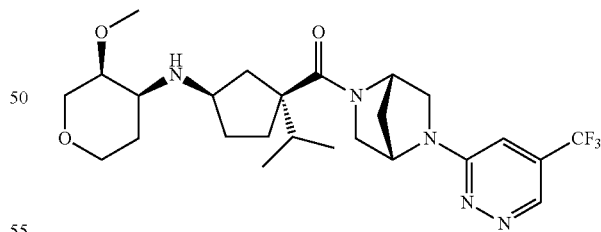

1,5-anhydro-2,3-dideoxy-3-{[(1R,3S)-3-isopropyl-3-({(1S,4S)-5-[5-(trifluoromethyl)pyridazin-3-yl]-2,5-diazabicyclo[2.2.1]hept-2-yl}carbonyl)cyclopentyl]amino}-4-O-methyl-D-erythro-pentitol Prepared as described in example 2 starting with (1S,4S)-4-(2,5-dimethyl-1H-pyrrol-1-yl)-1-isopropylcyclopent-2-ene-1-carboxylic acid and skipping steps 1 and 2 and using 3-chloro-5-(trifluoromethyl)pyridazine in place of 2-chloro-4-(trifluoromethyl)pyrimidine in step 8. LC/MS (M+

H)=512.2849 exp, 512.2864 obs; ¹H NMR (400 MHz, CDCl₃) δ ppm 8.73 (1H), 6.75-6.68 (1H), 5.32-4.79 (2H), 4.07-4.04 (1H), 3.93-3.89 (1H), 3.80-3.55 (2H), 3.52-3.16 (8H), 3.13-3.03 (1H), 2.82-2.63 (1H), 2.51-2.38 (1H), 2.09-1.42 (10H), 1.36-1.24 (1H), 0.93-0.75 (6H)

Example 19

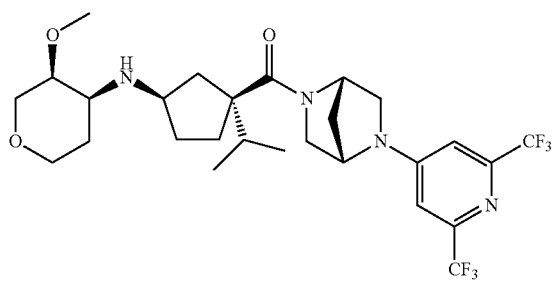

1,5-anhydro-3-{[(1R,3S)-3-isopropyl-3-({(1S,4S)-5-[2,6-bis(trifluoromethyl)pyridin-4-yl]-2,5-diazabicyclo[2.2.1]hept-2-yl}carbonyl)-3-isopropylcyclopentyl]amino}-2,3-dideoxy-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 4-chloro-2,6-bis(trifluoromethyl)pyridine in place of 4-chloro-6-(trifluoromethyl)pyrimidine in step 8. LC/MS (M+H)=579.2770 exp, 579.2667 obs; ¹H NMR (400 MHz, CDCl₃) δ ppm 6.94-6.67 (2H), 5.17-4.78 (1H), 4.60 (1H), 4.06-4.04 (1H), 3.92-3.89 (1H), 3.68-3.57 (2H), 3.42-3.16 (8H), 3.13-3.05 (1H), 2.79-2.62 (1H), 2.48-2.37 (1H), 2.08-1.86 (3H), 1.83-1.54 (6H), 1.52-1.42 (1H), 1.37-1.24 (1H), 0.92-0.76 (6H)

Example 20

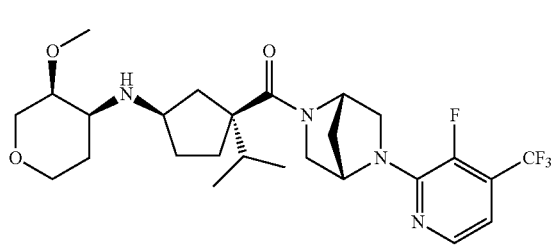

1,5-anhydro-2,3-dideoxy-3-{[(1R,3S)-3-({(1S,4S)-5-[3-fluoro-4-(trifluoromethyl)pyridin-2-yl]-2,5-diazabicyclo[2.2.1]hept-2-yl}carbonyl)-3-isopropylcyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 2-chloro-3-fluoro-4-(trifluoromethyl)pyridine in place of 4-chloro-6-(trifluoromethyl)pyrimidine in step 8. LC/MS (M+H)=529.2802 exp, 529.3431 obs; ¹H NMR (400 MHz, CDCl₃) δ ppm 7.98-7.97 (1H), 6.73-6.71 (1H), 5.07-4.67 (2H), 4.08-4.02 (1H), 3.94-3.88 (1H), 3.84-3.78 (1H), 3.64-3.47 (3H), 3.40-3.21 (6H), 3.13-3.04 (1H), 2.80-2.69 (1H), 2.49-2.39 (1H), 2.10-1.56 (9H), 1.54-1.42 (1H), 1.37-1.28 (1H), 0.92-0.75 (6H)

Example 21

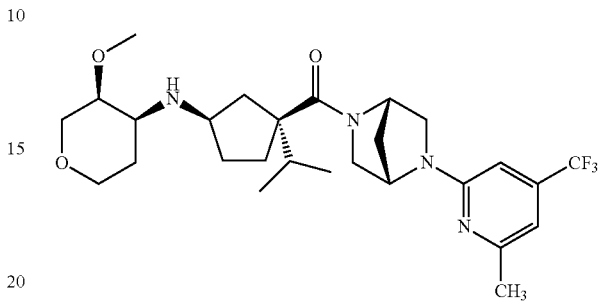

1,5-anhydro-2,3-dideoxy-3-{[(1R,3S)-3-isopropyl-3-({(1S,4S)-5-[6-methyl-4-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 2-chloro-6-methyl-4-(trifluoromethyl)pyridine in place of 4-chloro-6-(trifluoromethyl)pyrimidine in step 8. LC/MS (M+H)=525.3052 exp, 525.3242 obs; ¹H NMR (400 MHz, CDCl₃) δ ppm 6.61 (1H), 6.29-6.24 (1H), 5.14-4.71 (2H), 4.17-4.04 (2H), 3.98-3.90 (1H), 3.70-3.49 (3H), 3.48-3.13 (7H), 2.91-2.72 (1H), 2.50-2.32 (4H), 2.11-1.39 (11H), 0.94-0.71 (6H)

Example 22

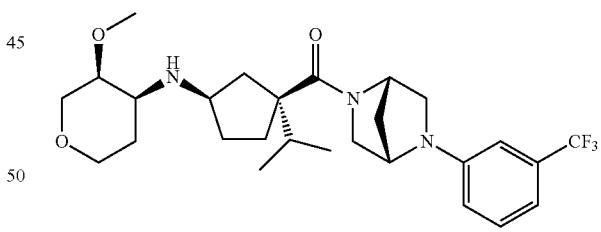

1,5-anhydro-2,3-dideoxy-3-{[(1R,3S)-3-isopropyl-3-({(1S,4S)-5-[3-(trifluoromethyl)phenyl]-2,5-diazabicyclo[2.2.1]hept-2-yl}carbonyl)cyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 3-iodo-benzotrifluoride in place of 4-chloro-6-(trifluoromethyl)pyrimidine in step 8. LC/MS (M+H)=510.2943 exp, 510.2976 obs; ¹H NMR (400 MHz, CDCl₃) δ ppm 7.30-7.25 (1H), 6.92-6.90 (1H), 6.72-6.65 (2H), 5.06-4.68 (1H), 4.44 (1H), 4.07-3.99 (1H), 3.94-3.86 (1H), 3.71-3.51 (2H), 3.48-

3.19 (7H), 3.14-3.01 (1H), 2.81-2.69 (1H), 2.61-2.35 (1H), 2.09-1.54 (9H), 1.51-1.40 (1H), 1.35-1.27 (1H), 0.94-0.72 (6H)

Example 23

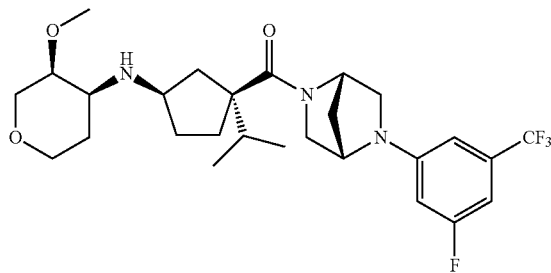

1,5-anhydro-2,3-dideoxy-3-{[(1R,3S)-3-({(1S,4S)-5-[3-fluoro-5-(trifluoromethyl)phenyl]-2,5-diazabicyclo[2.2.1]hept-2-yl}carbonyl)-3-isopropylcyclopentyl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2 and using 3-bromo-5-fluorobenzotrifluoride in place of 4-chloro-6-(trifluoromethyl)pyrimidine in step 8. LC/MS (M+H)=528.2849 exp, 528.2996 obs; $^1$H NMR (400 MHz, CDCl$_3$) δ ppm 6.61-6.58 (1H), 6.48 (1H), 6.35-6.33 (1H), 5.06-4.69 (1H), 4.39 (1H), 4.06-4.00 (1H), 3.94-3.86 (1H), 3.65-3.50 (2H), 3.46-3.15 (7H), 3.12-3.00 (1H), 2.80-2.70 (1H), 2.49-2.32 (1H), 2.06-1.73 (6H), 1.69-1.40 (4H), 1.36-1.27 (1H), 0.94-0.72 (6H)

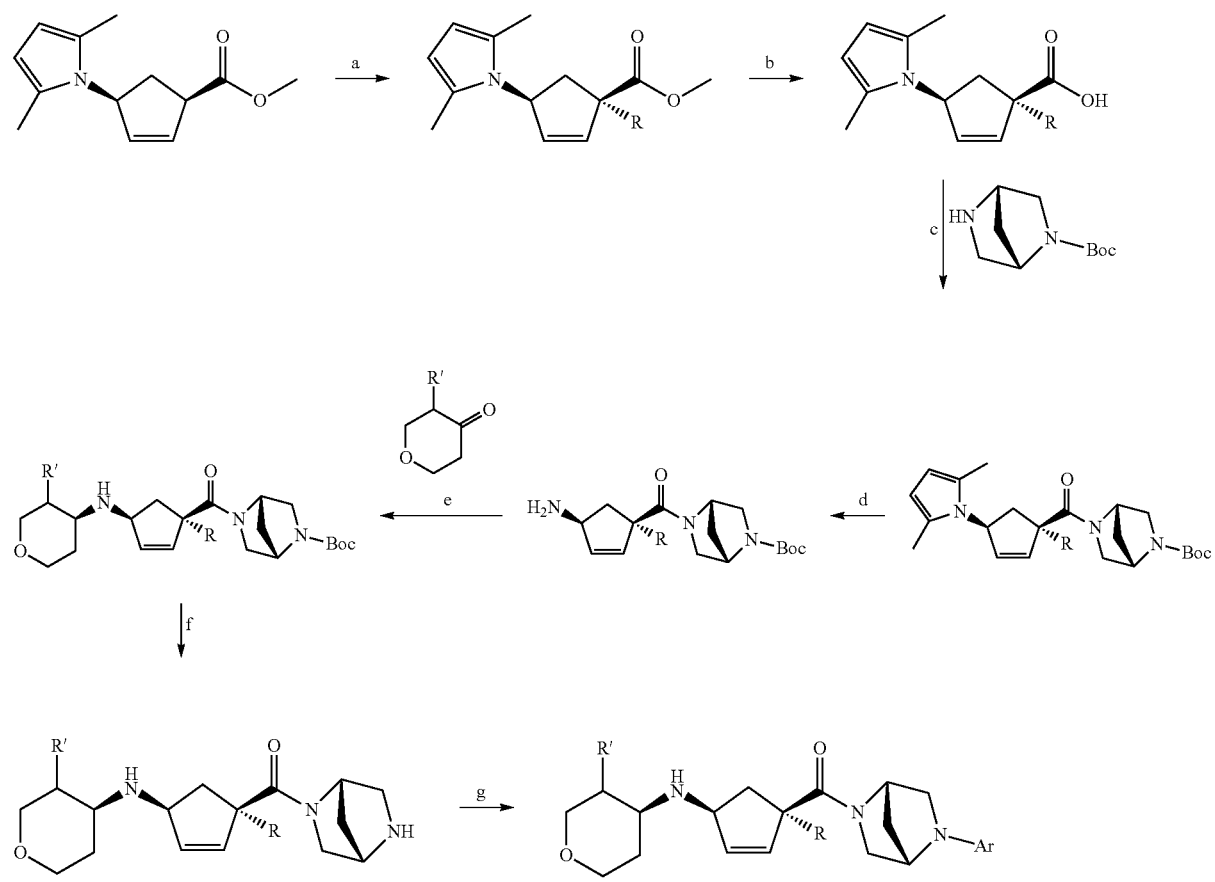

Scheme 2. Preparation of examples 24-44 a) LDA or NaHMDS, R—X, THF;
b) 2.5N NaOH, MeOH;
c) 2.2.1-Boc, DMF, DIPEA, Bop;
d) H$_2$NOH*HCl, MeOH, NH$_2$OH(aq);
e) pyranone, DCM, Na(OAc)$_3$BH;
f) 4N HCl/1,4-dioxane;
g) cond a or cond b or cond c cond a = Ar—X, DMSO, Et$_3$N, 120° C.
cond b = Ar—X, Cs$_2$CO$_3$, XantPhos, Pd$_2$(dba)$_3$, dioxane, DMSO
cond c = Ar—X, 1,4-dioxane, Et$_3$N, 100° C.

Example 24

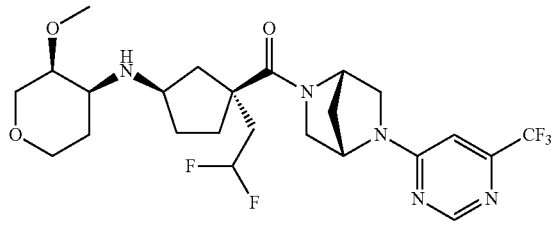

1,5-anhydro-2,3-dideoxy-3-{[(1R,3S)-3-(2,2-difluoroethyl)-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol

Step 1: Preparation of 2,2-difluoroethyl trifluoromethanesulfonate

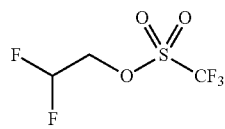

Triflic anhydride (27.9 g, 99.1 mmol) was placed in a flask and cooled with an ice bath. 2,2-Difluoroethanol (8.1 g, 99.1 mmol) was added and the reaction was heated to 84° C. for 1 hour. The reaction was cooled in an ice bath and poured into 100 ml cold 5% NaHCO$_3$ solution. The mixture was extracted with diethyl ether, dried over MgSO$_4$, and concentrated under reduced pressure to remove the ether. The residue was vaccuum distilled to give 2,2-difluoroethyl trifluoromethanesulfonate as a clear liquid (13.6 g, 64%, bp~55° C.). $^1$H NMR (400 MHz, CDCl$_3$) δ ppm 6.17-5.88 (1H), 4.61-4.13 (2H)

Step 2: Preparation of methyl (1S,4S)-1-(2,2-difluoroethyl)-4-(2,5-dimethyl-1H-pyrrol-1-yl)cyclopent-2-ene-1-carboxylate

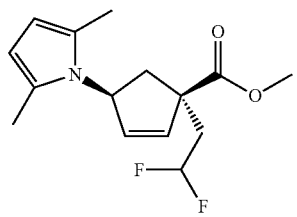

A −40° C. solution of 2M (in Ethylbenzene/THF/Heptane) LDA (36 ml, 72 mmol) in THF (80 ml) was placed in flask with THF (80 ml) was treated with a solution of methyl (1R,4S)-4-(2,5-dimethyl-1H-pyrrol-1-yl)cyclopent-2-ene-1-carboxylate (7.9 g, 36.3 mmol) in THF (17 ml) while keeping the temperature less than −32° C. The reaction was stirred for 30 min and then 2,2-difluoroethyl trifluoromethanesulfonate was added slowly, keeping the temperature <−28° C. The reaction was stirred with cold bath in place and allow to slowly warm. After 4 hours the reaction was poured into NH$_4$Cl solution and extracted twice with ethyl acetate. The combined organics were washed with brine, dried over MgSO$_4$ and concentrated to give a brown oil. The oil was passed through a column of silica gel with 10% ethyl acetate/hexanes to give methyl (1S,4S)-1-(2,2-difluoroethyl)-4-(2,5-dimethyl-1H-pyrrol-1-yl)cyclopent-2-ene-1-carboxylate as a brown oil. (7.5 g, 73%). $^1$H NMR (400 MHz, CDCl$_3$) δ ppm 6.07-6.04 (1H), 6.02-6.00 (0.25H) 5.98-5.96 (1H), 5.88-5.86 (0.5H), 5.75-5.72 (2.25H), 5.36-5.30 (1H), 3.74 (3H), 2.53-2.41 (2H), 2.39-2.22 (2H), 2.19 (6H)

Step 3: Preparation of (1S,4S)-1-(2,2-difluoroethyl)-4-(2,5-dimethyl-1H-pyrrol-1-yl)cyclopent-2-ene-1-carboxylic acid

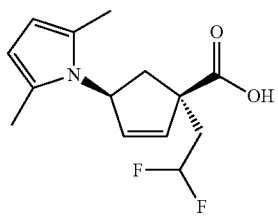

A solution of methyl (1S,4S)-1-(2,2-difluoroethyl)-4-(2,5-dimethyl-1H-pyrrol-1-yl)cyclopent-2-ene-1-carboxylate (7.54 g, 26.6 mmol) in methanol (60 ml) was treated with 2.5N NaOH (15 ml, 37.5 mmol) and stirred at room temperature for 22 hours. The methanol was removed under reduced pressure and the residue partitioned between diethyl ether and water. The layers were separated and the aqueous was acidified with 4N HCl, extracted with ethyl acetate, washed with brine, dried over MgSO$_4$, and concentrated under reduced pressure to give (1S,4S)-1-(2,2-difluoroethyl)-4-(2,5-dimethyl-1H-pyrrol-1-yl)cyclopent-2-ene-1-carboxylic acid as a brown oil (6.59 g, 92%). $^1$H NMR (400 MHz, CDCl$_3$) δ ppm 6.12-6.09 (1H), 6.07-6.05 (0.25H), 5.99-5.96 (1H), 5.93-5.91 (0.5H), 5.79-5.76 (0.25H), 5.74 (2H), 5.38-5.32 (1H), 2.54-2.46 (2H), 2.43-2.25 (2H), 2.20 (6H).

Step 4: Preparation of tert-butyl (1S,4S)-5-{[(1S,4S)-1-(2,2-difluoroethyl)-4-(2,5-dimethyl-1H-pyrrol-1-yl)cyclopent-2-en-1-yl]carbonyl}-2,5-diazabicyclo[2.2.1]heptane-2-carboxylate

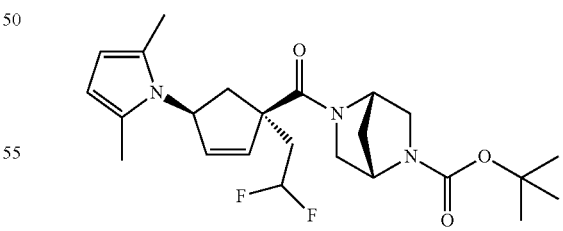

BOP=benzotriazol-1-yloxytris(dimethylamino)phosphoniumhexafluorophosphate

A solution of (1S,4S)-1-(2,2-difluoroethyl)-4-(2,5-dimethyl-1H-pyrrol-1-yl)cyclopent-2-ene-1-carboxylic acid (6.12 g, 22.6 mmol) in DMF (45 ml) was treated with N,N-diisopropylethylamine (11.7 ml, 67.2 mmol) and BOP (11.93 g, 27.0 mmol) and stirred under nitrogen at room temperature for 40 minutes. The (1S,4S)-2-BOC-2,5-diazabicyclo[2.2.1]

heptane (4.46 g, 22.5 mmol) was added and the reaction was stirred for 18 hours. The reaction was diluted with ethyl acetate (100 ml) and washed with 60% saturated NaHCO₃ (125 ml). The aqueous layer was extracted with ethyl acetate. The organic layers were combined, washed with brine, dried over MgSO₄ and concentrated under reduced pressure to give a brown oil (16.8 g). The oil was passed through a column of silica gel with 50% ethyl acetate/hexanes to give tert-butyl (1S,4S)-5-{[(1S,4S)-1-(2,2-difluoroethyl)-4-(2,5-dimethyl-1H-pyrrol-1-yl)cyclopent-2-en-1-yl]carbonyl}-2,5-diazabicyclo[2.2.1]heptane-2-carboxylate as a brown foam (7.86 g, 78%). ¹H NMR (400 MHz, CDCl₃) δ ppm 6.25-6.19 (1H), 6.04-5.96 (1.25H), 5.85-5.81 (0.5H), 5.74-5.68 (2.25H), 5.37-5.25 (1H), 4.98-4.43 (2H), 3.73-3.29 (4H), 2.77-2.29 (2H), 2.26-2.09 (8H), 1.93-1.67 (2H), 1.46-1.34 (9H).

Step 5: Preparation of tert-butyl (1S,4S)-5-{[(1S,4S)-4-amino-1-(2,2-difluoroethyl)cyclopent-2-en-1-yl]carbonyl}-2,5-diazabicyclo[2.2.1]heptane-2-carboxylate

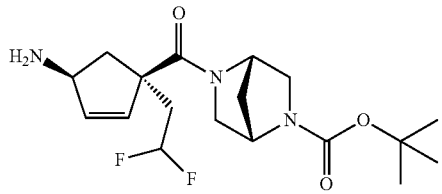

A solution of tert-butyl (1S,4S)-5-{[(1S,4S)-1-(2,2-difluoroethyl)-4-(2,5-dimethyl-1H-pyrrol-1-yl)cyclopent-2-en-1-yl]carbonyl}-2,5-diazabicyclo[2.2.1]heptane-2-carboxylate (7.86 g, 17.5 mmol) in methanol (100 ml) and water (30 ml) was treated with hydroxylamine hydrochloride (6.35 g, 91.0 mmol) and 50 weight % solution of hydroxylamine (5.0 ml, 81.6 mmol). The reaction was stirred under nitrogen and heated to 66° C. for 39 hours. The reaction was cooled to room temperature, diluted with water, and made basic (pH~11) by the addition of 2.5N NaOH. The reaction mixture was extracted with ethyl acetate (3×150 ml), washed with brine, dried over MgSO₄ and concentrated under reduced pressure to give a crude mixture of tert-butyl (1S,4S)-5-{[(1S,4S)-4-amino-1-(2,2-difluoroethyl)cyclopent-2-en-1-yl]carbonyl}-2,5-diazabicyclo[2.2.1]heptane-2-carboxylate as a brown oil (9.12 g, theoretical yield 6.50 g) which was used without further purification in the next step.

Step 6: Preparation of tert-butyl (1S,4S)-5-{[(1S,3R)-3-amino-1-(2,2-difluoroethyl)cyclopentyl]carbonyl}-2,5-diazabicyclo[2.2.1]heptane-2-carboxylate

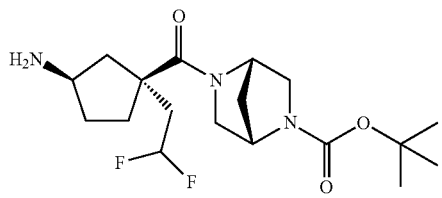

A mixture of tert-butyl (1S,4S)-5-{[(1S,4S)-4-amino-1-(2,2-difluoroethyl)cyclopent-2-en-1-yl]carbonyl}-2,5-diazabicyclo[2.2.1]heptane-2-carboxylate (6.50 g, 17.5 mmol) and 5% palladium on carbon in methanol (100 ml) was stirred at room temperature under 46 psi of hydrogen for 21 hours. The reaction was filtered through celite and the filter cake washed with methanol. The filtrate and washings were concentrated under reduced pressure to give tert-butyl (1S,4S)-5-{[(1S,3R)-3-amino-1-(2,2-difluoroethyl)cyclopentyl]carbonyl}-2,5-diazabicyclo[2.2.1]heptane-2-carboxylate as a brown oil (6.67 g, theoretical yield 6.54 g) which was used without further purification in the next step.

Step 7: Preparation of 1,5-anhydro-3-{[(1R,3S)-3-{[(1S,4S)-5-(tert-butoxycarbonyl)-2,5-diazabicyclo[2.2.1]hept-2-yl]carbonyl}-3-(2,2-difluoroethyl)cyclopentyl]amino}-2,3-dideoxy-4-O-methyl-D-erythro-pentitol

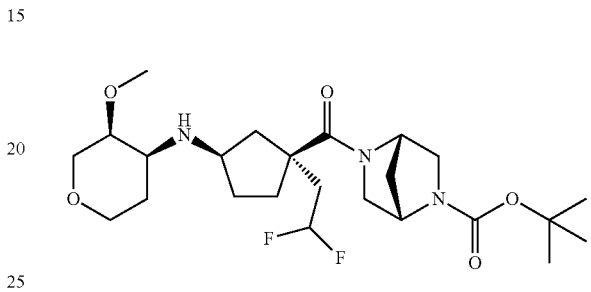

A 0° C. solution of tert-butyl (1S,4S)-5-{[(1S,3R)-3-amino-1-(2,2-difluoroethyl)cyclopentyl]carbonyl}-2,5-diazabicyclo[2.2.1]heptane-2-carboxylate (3.45 g, 9.2 mmol) in dichloromethane (50 ml) was treated with sodium triacetoxyborohydride (5.34 g, 25.2 mmol) and (3R)-3-methoxytetrahydro-4H-pyran-4-one (2.31 g, 17.8 mmol). The reaction was stirred under nitrogen at 0° C. for 30 minutes then allowed to warm to room temperature and stirred for 47 hours. The reaction was treated with 2.5N NaOH (35 mL) and stirred for 10 minutes. The reaction was diluted with water and the layers separated. The aqueous layer was extracted twice with ethyl acetate. The dichloromethane layer was concentrated under reduced pressure and partitioned between ethyl acetate and water. The organic layers were combined, washed with brine, dried over MgSO₄, concentrated under reduced pressure and purified with the Biotage (0-100% methanol/ethyl acetate, 15 column volumes) to give 1,5-anhydro-3-{[(1R,3S)-3-{[(1S,4S)-5-(tert-butoxycarbonyl)-2,5-diazabicyclo[2.2.1]hept-2-yl]carbonyl}-3-(2,2-difluoroethyl)cyclopentyl]amino}-2,3-dideoxy-4-O-methyl-D-erythro-pentitol (2.13 g, 47%) which was used without further purification in the next step.

Step 8: Preparation of 1,5-anhydro-2,3-dideoxy-3-{[(1R,3S)-3-{[(1S,4S)-2,5-diazabicyclo[2.2.1]hept-2-yl]carbonyl}-3-(2,2-difluoroethyl)cyclopentyl]amino}-4-O-methyl-D-erythro-pentitol (HCl salt)

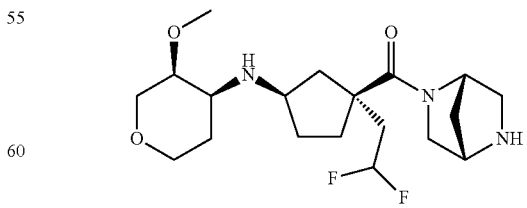

To a solution of 1,5-anhydro-3-{[(1R,3S)-3-{[(1S,4S)-5-(tert-butoxycarbonyl)-2,5-diazabicyclo[2.2.1]hept-2-yl]carbonyl}-3-(2,2-difluoroethyl)cyclopentyl]amino}-2,3-dideoxy-4-O-methyl-D-erythro-pentitol (2.13 g, 4.4 mmol)

in 1,4-dioxane (20 ml) was added 4N HCl/1,4-dioxane (20 ml). The reaction was stirred at room temperature for 16 hours. The liquid was decanted leaving a gummy solid which was dissolved in methanol and concentrated under reduced pressure. The residue was dissolved in methanol/methylene chloride and concentrated to give the HCl salt of 1,5-anhydro-2,3-dideoxy-3-{[(1R,3S)-3-{[(1S,4S)-2,5-diazabicyclo[2.2.1]hept-2-yl]carbonyl}-3-(2,2-difluoroethyl)cyclopentyl]amino}-4-O-methyl-D-erythro-pentitol as a brown foam (2.23 g, theoretical yield 1.85 g) which was used in the next step without further purification.

Step 9: Preparation of 1,5-anhydro-2,3-dideoxy-3-{[(1R,3S)-3-(2,2-difluoroethyl)-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol

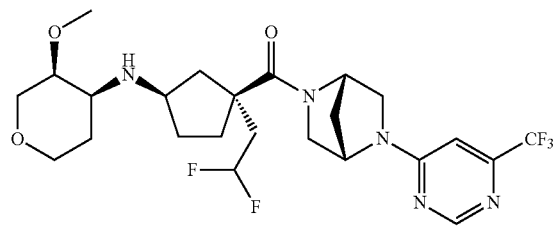

The HCl salt of 1,5-anhydro-2,3-dideoxy-3-{[(1R,3S)-3-{[(1S,4S)-2,5-diazabicyclo[2.2.1]hept-2-yl]carbonyl}-3-(2,2-difluoroethyl)cyclopentyl]amino}-4-O-methyl-D-erythro-pentitol (177 mg, 0.42 mmol) was placed in a flask with 1,4-dioxane (3 ml). To the stirred solution was added Xantphos (36 mg, 0.062 mmol), Pd$_2$(dba)$_3$ (22 mg, 0.024 mmol), Cs$_2$CO$_3$ (350 mg, 1.07 mmol), and 4-chloro-6-(trifluoromethyl)pyrimidine (195 mg, 1.07 mmol) dissolved in 1,4-dioxane (1 ml). DMSO (0.5 ml) was added for solubility and the reaction was heated to 100° C. for 21.5 hours. The reaction was allowed to cool to room temperature and filtered through celite. The filtrate was concentrated under reduced pressure and purified with the Biotage (0-100% methanol/ethyl acetate 15 column volumes) to give 1,5-anhydro-2,3-dideoxy-3-{[(1R,3S)-3-(2,2-difluoroethyl)-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol as a white foam (43 mg, 20%). LC/MS (M+H)= 534.2504 exp, 534.2597 obs; $^1$H NMR (400 MHz, CDCl$_3$) δ ppm 8.62 (1H), 6.74-6.46 (1H), 5.93-5.62 (1H), 5.29-4.50 (2H), 4.08-4.03 (1H), 3.93-3.88 (1H), 3.77-3.55 (2H), 3.52-3.32 (6H), 3.30-3.21 (3H), 2.76-2.65 (1H), 2.51-2.33 (1H), 2.21-1.84 (7H), 1.70-1.40 (5H)

Example 25

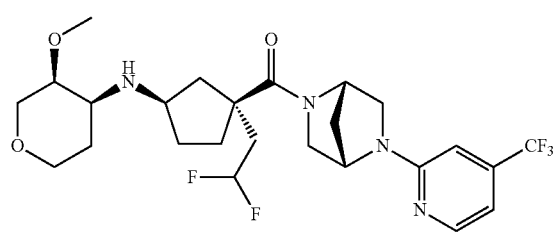

1,5-anhydro-2,3-dideoxy-3-{[(1R,3S)-3-(2,2-difluoroethyl)-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 24 using 2-chloro-4-(trifluoromethyl)pyridine in place of 4-chloro-6-(trifluoromethyl)pyrimidine in step 9. LC/MS (M+H)=533.2551 exp, 533.2651 obs; $^1$H NMR (400 MHz, CDCl$_3$) δ ppm 8.24-8.20 (1H), 6.74-6.73 (1H), 6.49-6.44 (1H), 5.95-5.57 (1H), 5.07-4.73 (2H), 4.06-4.01 (1H), 3.93-3.87 (1H), 3.70-3.49 (2H), 3.45-3.30 (6H), 3.28-3.20 (3H), 2.77-2.64 (1H), 2.53-2.36 (1H), 2.23-1.81 (7H), 1.73-1.41 (5H)

Example 26

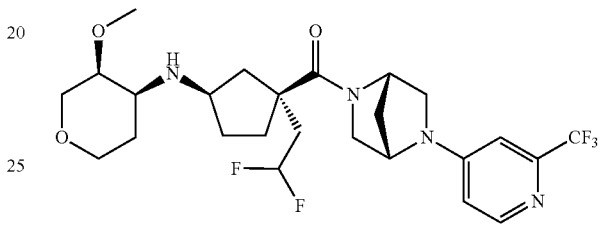

1,5-anhydro-2,3-dideoxy-3-{[(1R,3S)-3-(2,2-difluoroethyl)-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol Prepared as described in example 24 using 4-iodo-2-(trifluoromethyl)pyridine in place of 4-chloro-6-(trifluoromethyl)pyrimidine in step 9. LC/MS (M+H)=533.2551 exp, 533.2598 obs; $^1$H NMR (400 MHz, CDCl$_3$) δ ppm 8.29-8.27 (1H), 6.74-6.70 (1H), 6.50-6.43 (1H), 5.93-5.59 (1H), 5.09-4.74 (1H), 4.54 (1H), 4.07-4.02 (1H), 3.93-3.88 (1H), 3.68-3.48 (2H), 3.39-3.20 (7H), 2.74-2.62 (1H), 2.51-2.37 (1H), 2.19-1.77 (7H), 1.70-1.40 (5H)

Example 27

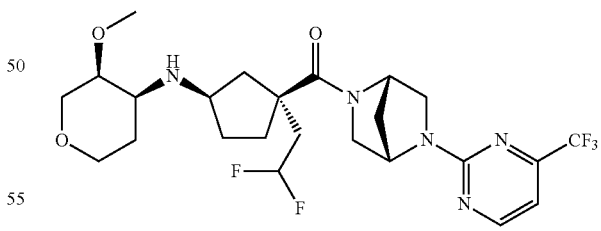

1,5-anhydro-2,3-dideoxy-3-{[(1R,3S)-3-(2,2-difluoroethyl)-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol Prepared as described in example 24 using 2-chloro-4-(trifluoromethyl)pyrimidine in place of 4-chloro-6-(trifluoromethyl)pyrimidine and modifying step 9 as follows. The HCl salt of 1,5-anhydro-2,3-dideoxy-3-{[(1R,3S)-3-{[(1S, 4S)-2,5-diazabicyclo[2.2.1]hept-2-yl]carbonyl}-3-(2,2-difluoroethyl)cyclopentyl]amino}-4-O-methyl-D-erythro-pentitol (175 mg, 0.41 mmol) was placed in flask with 1,4-dioxane (3 ml). Triethylamine (0.2 ml, 1.43 mmol) was added as well as 2-chloro-4-(trifluoromethyl)pyrimidine (237 mg, 1.30 mmol). DMSO (0.3 ml) was added for solubility and the reaction was heated to 100° C. for 14.5 hours. The reaction was cooled to room temperature and partitioned between ethyl acetate and water. The aqueous layer was extracted with ethyl acetate and the combined organics were washed with brine, dried over MgSO$_4$, concentrated under reduced pressure and purified with the Biotage (0-100% methanol/ethyl acetate 15 column volumes) to give 1,5-anhydro-2,3-dideoxy-3-{[(1R,3S)-3-(2,2-difluoroethyl)-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol as a brown foam (126 mg, 58%). LC/MS (M+H)=534.2504 exp, 534.2452 obs; $^1$H NMR (400 MHz, CDCl$_3$) δ ppm 8.48-8.45 (1H), 6.79-6.78 (1H), 5.96-5.58 (1H), 5.10-4.71 (2H), 4.07-4.01 (1H), 3.93-3.87 (1H), 3.69-3.55 (4H), 3.39-3.32 (4H), 3.30-3.21 (3H), 2.77-2.66 (1H), 2.52-2.40 (1H), 2.23-1.82 (7H), 1.70-1.39 (5H)

Example 28

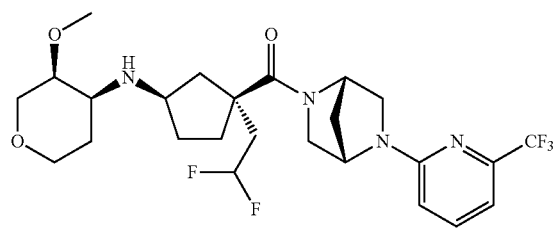

1,5-anhydro-2,3-dideoxy-3-{[(1R,3S)-3-(2,2-difluoroethyl)-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol Prepared as described in example 24 using 2-chloro-6-(trifluoromethyl)pyridine in place of 4-chloro-6-(trifluoromethyl)pyrimidine and modifying step 9 as follows. To a solution of HCl salt of 1,5-anhydro-2,3-dideoxy-3-{[(1R,3S)-3-{[(1S,4S)-2,5-diazabicyclo[2.2.1]hept-2-yl]carbonyl}-3-(2,2-difluoroethyl)cyclopentyl]amino}-4-O-methyl-D-erythro-pentitol (183 mg, 0.43 mmol) in DMSO (2 ml) was added triethylamine (0.2 ml, 1.43 mmol) and 2-chloro-6-(trifluoromethyl)pyridine (179 mg, 1.05 mmol). The reaction was heated to 120° C. for 14.5 hours. The reaction was cooled to room temperature, and added to stirring ice water. The mixture was extracted with ethyl acetate (3×). The combined organics were washed with brine, dried over MgSO$_4$ concentrated under reduced pressure and purified with the Biotage (0-100% methanol/ethyl acetate, 15 column volumes) to give 1,5-anhydro-2,3-dideoxy-3-{[(1R,3S)-3-(2,2-difluoroethyl)-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol as a brown foam (58 mg 28%). LC/MS (M+H)=533.2551 exp, 533.2546 obs; $^1$H NMR (400 MHz, CDCl$_3$) δ ppm 7.54-7.51 (1H), 6.91-6.89 (1H), 6.51-6.38 (1H), 5.94-5.54 (1H), 5.11-4.70 (2H), 4.06-4.01 (1H), 3.93-3.87 (1H), 3.70-3.53 (2H), 3.51-3.31 (6H), 3.27-3.20 (3H), 2.78-2.61 (1H), 2.53-2.36 (1H), 2.20-1.80 (7H), 1.68-1.38 (5H)

Example 29

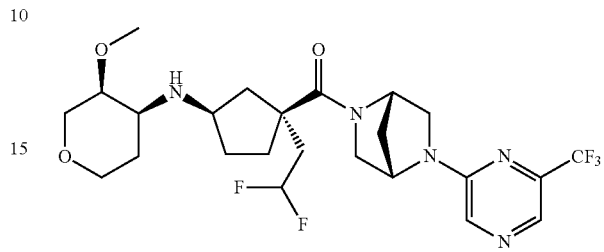

1,5-anhydro-2,3-dideoxy-3-{[(1R,3S)-3-(2,2-difluoroethyl)-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol Prepared as described in example 24 using 2-iodo-6-(trifluoromethyl)pyrazine in place of 4-chloro-6-(trifluoromethyl)pyrimidine in step 9. LC/MS (M+H)=534.2504 exp, 534.2548 obs; $^1$H NMR (400 MHz, CDCl$_3$) δ ppm 8.13 (1H), 8.01-7.93 (1H), 5.92-5.57 (1H), 5.09-4.75 (2H), 4.06-4.01 (1H), 3.92-3.87 (1H), 3.68-3.48 (4H), 3.38-3.30 (4H), 3.28-3.20 (3H), 2.74-2.63 (1H), 2.51-2.32 (1H), 2.21-1.83 (7H), 1.75-1.42 (5H)

Example 30

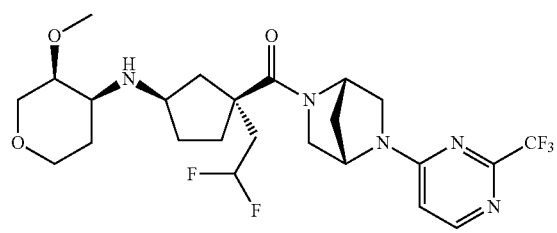

1,5-anhydro-2,3-dideoxy-3-{[(1R,3S)-3-(2,2-difluoroethyl)-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol Prepared as described in example 24 using 4-chloro-2-(trifluoromethyl)pyrimidine in place of 4-chloro-6-(trifluoromethyl)pyrimidine in step 9. LC/MS (M+H)=534.2504 exp, 534.2521 obs; $^1$H NMR (400 MHz, CDCl$_3$) δ ppm 8.28-8.26 (1H), 6.52-6.24 (1H), 5.93-5.62 (1H), 5.33-4.38 (2H), 4.08-4.03 (1H), 3.94-3.89 (1H), 3.71-3.57 (2H), 3.49-3.33 (6H), 3.29-3.21 (3H), 2.75-2.66 (1H), 2.50-2.36 (1H), 2.22-1.86 (7H), 1.69-1.41 (5H)

Example 31

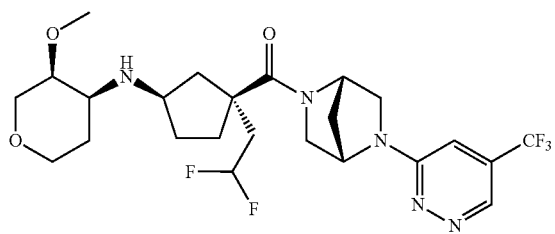

1,5-anhydro-2,3-dideoxy-3-{[(1R,3S)-3-(2,2-difluoroethyl)-3-({(1S,4S)-5-[5-(trifluoromethyl)pyridazin-3-yl]-2,5-diazabicyclo[2.2.1]hept-2-yl}carbonyl)cyclopentyl]amino}-4-O-methyl-D-erythro-pentitol Prepared as described in example 27 using 3-chloro-5-(trifluoromethyl)pyridazine in place of 2-chloro-4-(trifluoromethyl)pyrimidine in step 9. LC/MS (M+H)=534.2504 exp, 534.2531 obs; $^1$H NMR (400 MHz, CDCl$_3$) δ ppm 8.76 (1H), 6.74-6.68 (1H), 5.96-5.90 (1H), 5.37-4.84 (2H), 4.10-4.04 (1H), 3.96-3.90 (1H), 3.81-3.54 (3H), 3.47-3.34 (4H), 3.32-3.22 (4H), 2.77-2.67 (1H), 2.51-2.37 (1H), 2.22-1.86 (7H), 1.72-1.46 (5H)

Example 32

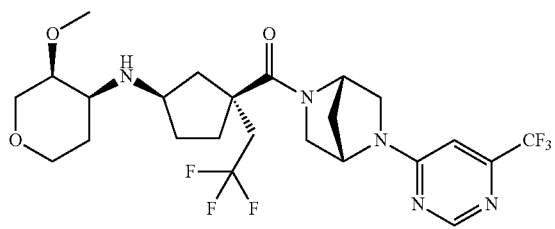

1,5-anhydro-2,3-dideoxy-4-O-methyl-3-{[(1R,3S)-3-(2,2,2-trifluoroethyl)-3-({(1S,4S)-5-[6-(trifluoromethyl)pyrimidin-4-yl]-2,5-diazabicyclo[2.2.1]hept-2-yl}carbonyl)cyclopentyl]amino}-D-erythro-pentitol Prepared as described in example 24 using 3,3,3-trifluoroethanol in place of 2,2-difluoroethanol in step 1. LC/MS (M+H)=552.2409 exp, 552.2432 obs; $^1$H NMR (400 MHz, CDCl$_3$) δ ppm 8.61 (1H), 6.70-6.45 (1H), 5.26-5.21 (1H), 5.08-4.96 (1H), 4.08-4.03 (1H), 3.92-3.87 (1H), 3.68-3.61 (2H), 3.53-3.44 (1H), 3.42-3.20 (8H), 2.72-2.65 (1H), 2.56-2.27 (3H), 2.08-1.88 (5H), 1.80-1.47 (5H)

Example 33

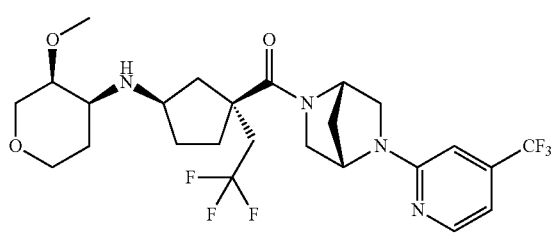

1,5-anhydro-2,3-dideoxy-4-O-methyl-3-{[(1R,3S)-3-(2,2,2-trifluoroethyl)-3-({(1S,4S)-5-[4-(trifluoromethyl)pyridin-2-yl]-2,5-diazabicyclo[2.2.1]hept-2-yl}carbonyl)cyclopentyl]amino}-D-erythro-pentitol Prepared as described in example 24 using 3,3,3-trifluoroethanol in place of 2,2-difluoroethanol in step 1 and using 2-chloro-4-(trifluoromethyl)pyridine in place of 2-chloro-6-(trifluoromethyl)pyridine in step 9. LC/MS (M+H)=551.2457 exp, 551.2703 obs; $^1$H NMR (400 MHz, CDCl$_3$) δ ppm 8.22-8.21 (1H), 6.74-6.73 (1H), 6.47-6.43 (1H), 5.06-4.71 (2H), 4.06-4.01 (1H), 3.92-3.87 (1H), 3.65-3.50 (3H), 3.40-3.20 (8H), 2.72-2.63 (1H), 2.53-2.27 (3H), 2.08-1.82 (5H), 1.78-1.45 (5H)

Example 34

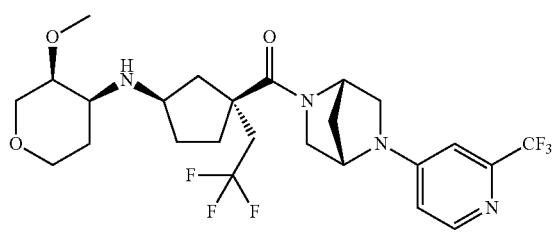

1,5-anhydro-2,3-dideoxy-4-O-methyl-3-{[(1R,3S)-3-(2,2,2-trifluoroethyl)-3-({(1S,4S)-5-[2-(trifluoromethyl)pyridin-4-yl]-2,5-diazabicyclo[2.2.1]hept-2-yl}carbonyl)cyclopentyl]amino}-D-erythro-pentitol Prepared as described in example 24 using 3,3,3-trifluoroethanol in place of 2,2-difluoroethanol in step 1 and using 4-iodo-2-(trifluoromethyl)pyridine in place of 2-chloro-4-(trifluoromethyl)pyrimidine in step 9. LC/MS (M+H)=551.2457 exp, 551.2610 obs; $^1$H NMR (400 MHz, CDCl$_3$) δ ppm 8.26-8.25 (1H), 6.71-6.68 (1H), 6.46-6.42 (1H), 5.09-4.83 (1H), 4.55-4.52 (1H), 4.05-4.01 (1H), 3.90-3.85 (1H), 3.66-3.48 (3H), 3.36-3.18 (8H), 2.70-2.62 (1H), 2.51-2.27 (3H), 2.06-1.87 (5H), 1.80-1.45 (5H)

Example 35

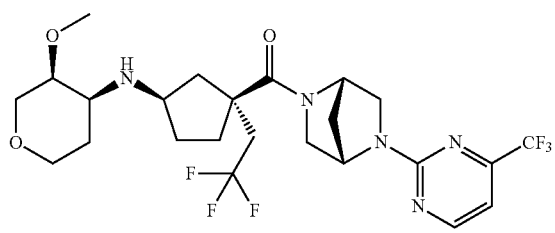

1,5-anhydro-2,3-dideoxy-4-O-methyl-3-{[(1R,3S)-3-(2,2,2-trifluoroethyl)-3-({(1S,4S)-5-[4-(trifluoromethyl)pyrimidin-2-yl]-2,5-diazabicyclo[2.2.1]hept-2-yl}carbonyl)cyclopentyl]amino}-D-erythro-pentitol Prepared as described in example 27 using 3,3,3-trifluoroethanol in place of 2,2-difluoroethanol in step 1. LC/MS (M+H)=552.2409 exp, 551.2426 obs; $^1$H NMR (400 MHz, CDCl$_3$) δ ppm 8.50-8.46 (1H), 6.81-6.80 (1H), 5.11-4.74 (2H), 4.13-4.06 (1H), 3.97-3.92 (1H), 3.67-3.59 (4H), 3.41-3.25 (7H), 2.90-2.75 (1H), 2.54-2.33 (3H), 2.07-1.88 (5H), 1.79-1.58 (5H)

Example 36

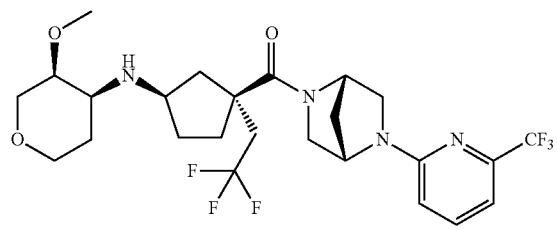

1,5-anhydro-2,3-dideoxy-4-O-methyl-3-{[(1R,3S)-3-(2,2,2-trifluoroethyl)-3-({(1S,4S)-5-[6-(trifluoromethyl)pyridin-2-yl]-2,5-diazabicyclo[2.2.1]hept-2-yl}carbonyl)cyclopentyl]amino}-D-erythro-pentitol Prepared as described in example 27 using 3,3,3-trifluoroethanol in place of 2,2-difluoroethanol in step 1 and using 2-chloro-6-(trifluoromethyl)pyridine in place of 2-chloro-4-(trifluoromethyl)pyrimidine in step 9. LC/MS (M+H)= 551.2457 exp, 551.2581 obs; $^1$H NMR (400 MHz, CDCl$_3$) δ ppm 7.55-7.51 (1H), 6.92-6.90 (1H), 6.47-6.40 (1H), 5.12-4.70 (2H), 4.07-4.03 (1H), 3.93-3.88 (1H), 3.72-3.47 (3H), 3.40-3.31 (5H), 3.28-3.20 (3H), 2.73-2.64 (1H), 2.53-2.25 (3H), 2.10-1.80 (5H), 1.77-1.44 (5H)

Example 37

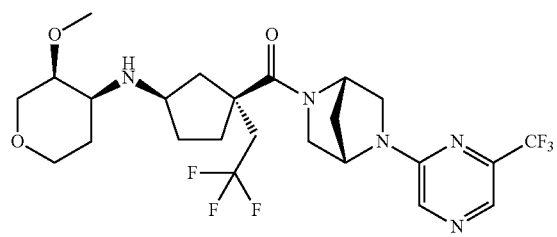

1,5-anhydro-2,3-dideoxy-4-O-methyl-3-{[(1R,3S)-3-(2,2,2-trifluoroethyl)-3-({(1S,4S)-5-[6-(trifluoromethyl)pyrazin-2-yl]-2,5-diazabicyclo[2.2.1]hept-2-yl}carbonyl)cyclopentyl]amino}-D-erythro-pentitol Prepared as described in example 24 using 3,3,3-trifluoroethanol in place of 2,2-difluoroethanol in step 1 and using 1-iodo-6-(trifluoromethyl)pyrazine in place of 4-chloro-6-(trifluoromethyl)pyrimidine in step 9. LC/MS (M+H)= 552.2409 exp, 552.2443 obs; $^1$H NMR (400 MHz, CDCl$_3$) δ ppm 8.16 (1H), 8.01-7.96 (1H), 5.09-4.96 (2H), 4.09-4.04 (1H), 3.94-3.89 (1H), 3.68-3.57 (3H), 3.53-3.49 (1H), 3.39-3.23 (7H), 2.74-2.67 (1H), 2.54-2.29 (3H), 2.09-1.90 (5H), 1.81-1.49 (5H)

Example 38

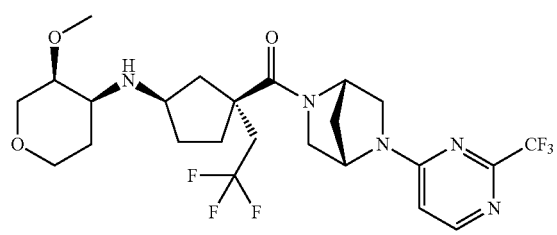

1,5-anhydro-2,3-dideoxy-4-O-methyl-3-{[(1R,3S)-3-(2,2,2-trifluoroethyl)-3-({(1S,4S)-5-[2-(trifluoromethyl)pyrimidin-4-yl]-2,5-diazabicyclo[2.2.1]hept-2-yl}carbonyl)cyclopentyl]amino}-D-erythro-pentitol Prepared as described in example 24 using 3,3,3-trifluoroethanol in place of 2,2-difluoroethanol in step 1 and using 4-chloro-2-(trifluoromethyl)pyrimidine in place of 4-chloro-6-(trifluoromethyl)pyrimidine in step 9. LC/MS (M+H)= 552.2409 exp, 552.3073 obs; $^1$H NMR (400 MHz, CDCl$_3$) δ ppm 8.23-8.21 (1H), 6.49-6.22 (1H), 5.25-4.93 (2H), 4.04-3.99 (1H), 3.89-3.83 (1H), 3.65-3.57 (2H), 3.46-3.17 (9H), 2.68-2.62 (1H), 2.52-2.26 (3H), 2.05-1.85 (5H), 1.76-1.43 (5H)

Example 39

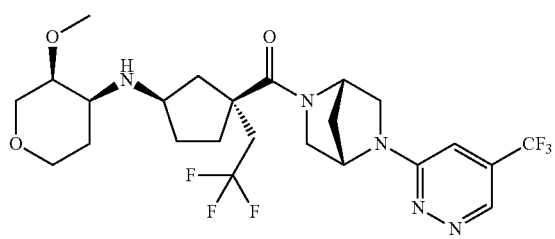

1,5-anhydro-2,3-dideoxy-4-O-methyl-3-{[(1R,3S)-3-(2,2,2-trifluoroethyl)-3-({(1S,4S)-5-[5-(trifluoromethyl)pyridazin-3-yl]-2,5-diazabicyclo[2.2.1]hept-2-yl}carbonyl)cyclopentyl]amino}-D-erythro-pentitol Prepared as described in example 27 using 3,3,3-trifluoroethanol in place of 2,2-difluoroethanol in step 1 and using 3-chloro-5-(trifluoromethyl)pyridazine in place of 2-chloro-4-(trifluoromethyl)pyrimidine in step 9. LC/MS (M+H)= 552.2409 exp, 552.2344 obs; $^1$H NMR (400 MHz, CDCl$_3$) δ ppm 8.72 (1H), 6.72-6.64 (1H), 5.32-4.82 (2H), 4.06-4.01 (1H), 3.91-3.86 (1H), 3.78-3.53 (3H), 3.42-3.18 (8H), 2.69-2.64 (1H), 2.52-2.24 (3H), 2.07-1.84 (5H), 1.76-1.44 (5H)

Example 40

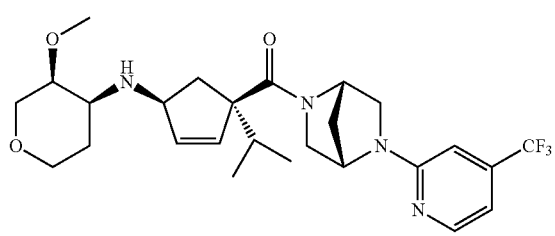

1,5-anhydro-2,3-dideoxy-3-{[(1S,4S)-4-isopropyl1-4-({(1S,4S)-5-[4-(trifluoromethyl)pyridin-2-yl]-2,5-diazabicyclo[2.2.1]hept-2-yl}carbonyl)cyclopent-2-en-1-yl]amino}-4-O-methyl-D-erythro-pentitol Prepared as described in example 1 starting with (1S,4S)-4-(2,5-dimethyl-1H-pyrrol-1-yl)-1-isopropylcyclopent-2-ene-1-carboxylic acid and skipping steps 1, 2 and 5. LC/MS (M+H)=509.2739 exp, 509.2724 obs; $^1$H NMR (400 MHz, CDCl$_3$) δ ppm 8.19 (1H), 6.72-6.68 (1H), 6.46-6.38 (1H), 5.90-5.75 (2H), 5.09-4.82 (2H), 4.02-3.12 (13H), 2.86-2.67 (1H), 2.46-2.16 (1H), 2.08-1.47 (7H), 0.84-0.64 (6H)

Example 41

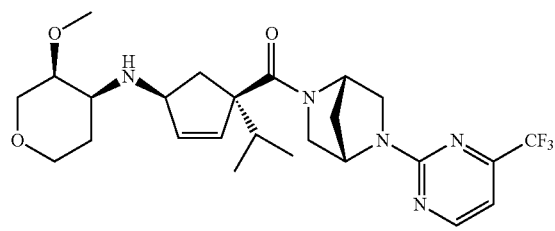

1,5-anhydro-2,3-dideoxy-3-{[(1S,4S)-4-isopropyll-4-({(1S,4S)-5-[4-(trifluoromethyl)pyrimidin-2-yl]-2,5-diazabicyclo[2.2.1]hept-2-yl}carbonyl)cyclopent-2-en-1-yl]amino}-4-O-methyl-D-erythro-pentitol Prepared as described in example 2 starting with (1S,4S)-4-(2,5-dimethyl-1H-pyrrol-1-yl)-1-isopropylcyclopent-2-ene-1-carboxylic acid and skipping steps 1, 2 and 5. LC/MS (M+H)=510.2692 exp, 510.2926 obs; ¹H NMR (400 MHz, CDCl₃) δ ppm 8.43-8.42 (1H), 6.75-6.74 (1H), 5.90-5.77 (2H), 5.09-4.80 (2H), 4.01-3.16 (13H), 2.86-2.69 (1H), 2.45-2.17 (1H), 2.08-1.30 (7H), 0.82-0.66 (6H)

Example 42

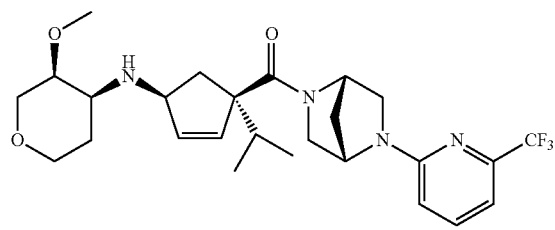

1,5-anhydro-2,3-dideoxy-3-{[(1S,4S)-4-isopropyll-4-({(1S,4S)-5-[6-(trifluoromethyl)pyridin-2-yl]-2,5-diazabicyclo[2.2.1]hept-2-yl}carbonyl)cyclopent-2-en-1-yl]amino}-4-O-methyl-D-erythro-pentitol Prepared as described in example 1 starting with (1S,4S)-4-(2,5-dimethyl-1H-pyrrol-1-yl)-1-isopropylcyclopent-2-ene-1-carboxylic acid and skipping steps 1, 2 and 5. LC/MS (M+H)=509.2739 exp, 509.2680 obs; ¹H NMR (400 MHz, CDCl₃) δ ppm 7.55-7.52 (1H), 6.94-6.89 (1H), 6.52-6.40 (1H), 5.96-5.78 (2H), 5.12-4.84 (2H), 4.07-3.16 (13H), 2.90-2.69 (1H), 2.49-2.21 (1H), 2.12-1.42 (7H), 0.87-0.68 (3H)

Example 43

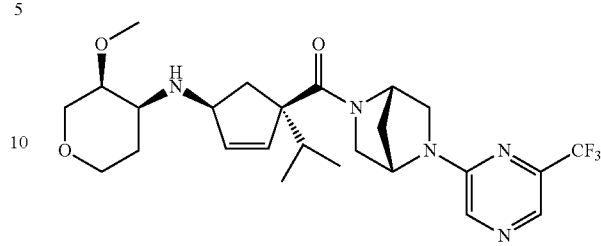

1,5-anhydro-2,3-dideoxy-3-{[(1S,4S)-4-isopropyll-4-({(1S,4S)-5-[6-(trifluoromethyl)pyrazin-2-yl]-2,5-diazabicyclo[2.2.1]hept-2-yl}carbonyl)cyclopent-2-en-1-yl]amino}-4-O-methyl-D-erythro-pentitol Prepared as described in example 3 starting with (1S,4S)-4-(2,5-dimethyl-1H-pyrrol-1-yl)-1-isopropylcyclopent-2-ene-1-carboxylic acid and skipping steps 1 and 2, skipping step 5, using (3R)-3-methoxytetrahydro-4H-pyran-4-one in step 6, and 2-chloro-6-(trifluoromethyl)pyrazine in place of 4-chloro-6-(trifluoromethyl)pyrimidine in step 8. LC/MS (M+H)=510.2692 exp, 510.2699 obs; ¹H NMR (400 MHz, CDCl₃) δ ppm 8.15 (1H), 8.04-7.95 (1H), 5.93-5.82 (2H), 5.17-4.91 (2H), 4.16-3.18 (13H), 2.91-2.69 (1H), 2.48-2.21 (1H), 2.10-1.52 (7H), 0.85-0.67 (6H)

Example 44

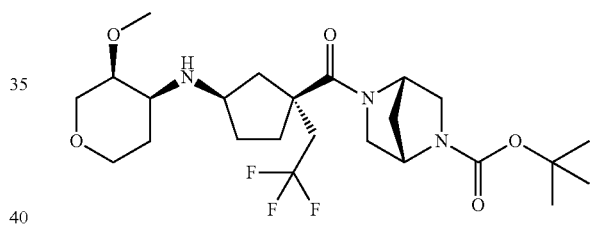

1,5-anhydro-3-{[(1R,3S)-3-{[(1S,4S)-5-(tert-butoxycarbonyl)-2,5-diazabicyclo[2.2.1]hept-2-yl]carbonyl}-3-(2,2,2-trifluoroethyl)cyclopentyl]amino}-2,3-dideoxy-4-O-methyl-D-erythro-pentitol Prepared as described in example 24 using 2,2,2-trifluoroethanol in place of 2,2-difluoroethanol in step 1 and skipping steps 8 and 9. LC/MS (M+H)=506.2842 exp, 506.3033 obs; ¹H NMR (400 MHz, CDCl₃) δ ppm 4.86-4.65 (1H), 4.52-4.38 (1H), 4.09-4.03 (1H), 3.93-3.87 (1H), 3.68-3.23 (11H), 2.73-2.68 (1H), 2.55-2.24 (3H), 2.10-2.03 (1H), 1.96-1.89 (1H), 1.85-1.59 (7H), 1.54-1.47 (1H), 1.44-1.39 (9H)

Scheme 3. Preparation of Examples 45-59

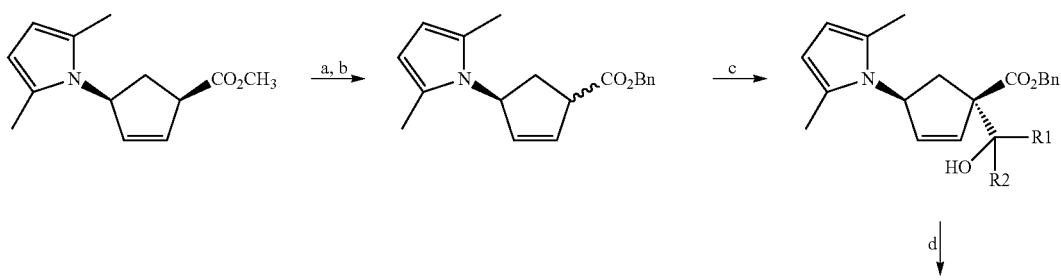

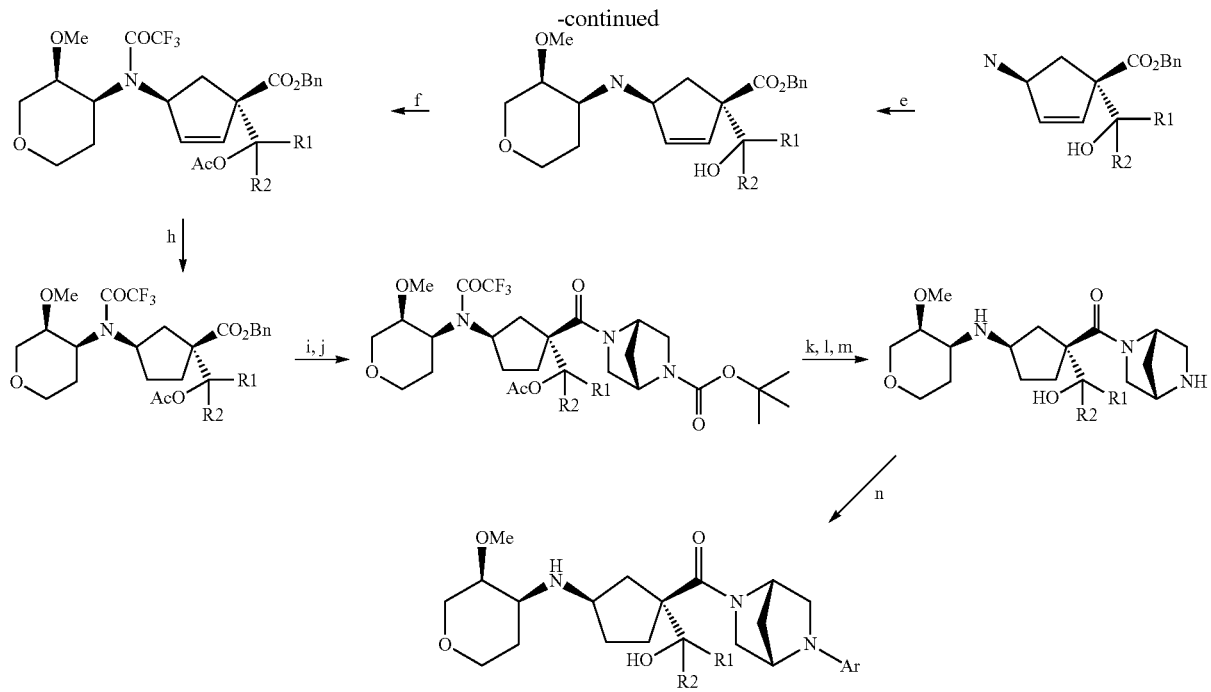

a) NaOH, MeOH, H$_2$O; b) BnOH, EDC, DMAP; c) LDA, R$_1$COR$_2$; d) NH$_2$OH*HCl, NH$_2$OH*H$_2$O, MeOH; e) MeO-pyranone, Na(OAc)$_3$BH; f) TFAA; g) AcCl, pyridine; h) H$_2$, Pt/C; i) (COCl)$_2$; j) arylpiperazine; k) K$_2$CO$_3$, MeOH; l) NaBH$_4$; m) HCl/dioxane; n) Ar—Cl, heat or Pd catalyst

Example 45

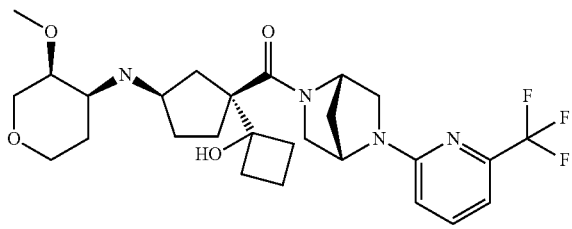

1,5-Anhydro-2,3-dideoxy-3-{[(1R,3S)-3-(1-hydroxycyclobutyl)-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol

Step 1. Benzyl (4S)-4-(2,5-dimethyl-1H-pyrrol-1-yl)cyclopent-2-ene-1-carboxylate

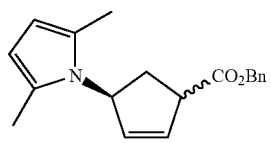

A solution of 11.04 g (50.4 mmol) of methyl (1R,4S)-4-(2,5-dimethyl-1H-pyrrol-1-yl)cyclopent-2-ene-1-carboxylate and 40 mL of 2.5 M sodium hydroxide in 100 mL of MeOH was stirred at ambient temperature for 45 minutes, then concentrated under reduced pressure to remove methanol. The residual aqueous solution was added to a stirred mixture of 20 g citric acid, 100 mL of water, and 100 mL of dichloromethane. The phases were separated and the aqueous extracted with two additional portions of dichloromethane. The organic phase was dried (Na$_2$SO$_4$) and concentrated under reduced pressure to provide the corresponding acid as a brown gum (10.98 g).

To a stirred solution of this acid, 10 mL (96 mmol) of benzyl alcohol, and 1.74 g (14 mmol) of DMAP in 50 mL of dichloromethane was added 13 g (69 mmol) of EDC, in five equal portions over 30 min. After 18 h, the solution was concentrated under reduced pressure, and the residual syrup partitioned between ether and water. The organic phase was washed with water and brine, with one back-extraction of the aqueous phases with ether. The combined organic phase was dried (MgSO$_4$), and concentrated under reduced pressure. Flash chromatography of the crude material on silica using 10% ethyl acetate in heptane afforded 13.75 g (93%) of the title compound as a colorless oil. 1H NMR (400 MHz, CHLOROFORM-d) showed a 60:40 mixture of epimers: δ ppm 2.09-2.32 (m, 1H) 2.20 (s, 6H) 2.67-2.85 (m, 1H) 3.62-3.70 (m, 0.6H) 3.85-3.92 (m, 0.4H) 5.16 (2s, 2H) 5.26-5.34 (m, 0.6H) 5.49-5.56 (m, 0.4H) 5.74 (br. s., 2H) 5.93-6.04 (m, 2H) 7.30-7.42 (m, 5H). TLC Rf 0.32 and 0.25 (10% ethyl acetate in hexane). LC-MS ES+ 296.2.

Step 2. Benzyl (1R,4S)-4-(2,5-dimethyl-1H-pyrrol-1-yl)-1-(1-hydroxycyclobutyl)cyclopent-2-ene-1-carboxylate

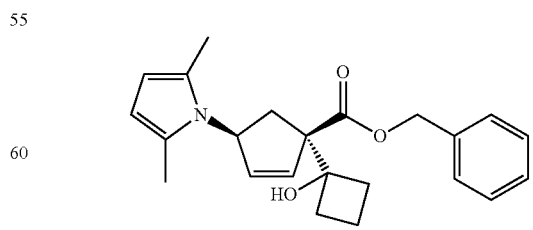

To a cold (−78 C), stirred solution of 6.17 g (20.9 mmol) of benzyl (4S)-4-(2,5-dimethyl-1H-pyrrol-1-yl)cyclopent-2-ene-1-carboxylate (Preparation SRT-0233) in 40 mL of dry THF, under Ar, was slowly added 23.3 mL of a commercial 1.8 M solution of LDA. The resulting solution was warmed to 0 C, stirred at that temperature for 10 min, and then recooled to −78 C for the addition of 2.3 mL (31 mmol) of cyclobutanone. This solution was stirred at −78 C for 1 h, then quenched at −78 C by the slow addition of a solution of 4.0 mL of 12N HCl in 10 mL of THF. Ethyl acetate and excess 1 M citric acid were added and the mixture was allowed to warm to RT. Extractive workup was followed by flash chromatography on silica using 25% ethyl acetate in heptane to provide 5.55 g (73%) of the title compound as a thick amber oil. ¹H NMR (400 MHz, CHLOROFORM-d) δ ppm 1.44-1.56 (m, 1H) 1.88-2.31 (m, 6H) 2.12 (s, 6H) 2.27 (dd, J=14.7, 7.5 Hz, 1H) 2.76 (dd, J=14.5, 9.0 Hz, 1H) 5.18 (s, 2H) 5.26-5.32 (m, 1H) 5.71 (s, 2H) 6.06 (dd, 1H) 6.10 (dd, 1H) 7.30-7.39 (m, 5H). TLC Rf 0.36 (30% ethyl acetate in hexane). LC-MS ES+ 366.2.

Step 3. Benzyl (1R,4S)-4-amino-1-(1-hydroxycyclobutyl)cyclopent-2-ene-1-carboxylate

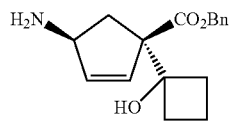

A mixture of 5.52 g (15.1 mmol) of benzyl (1R,4S)-4-(2,5-dimethyl-1H-pyrrol-1-yl)-1-(1-hydroxycyclobutyl)cyclopent-2-ene-1-carboxylate (Preparation SRT-0229), 8.20 g (120 mmol) of hydroxylamine hydrochloride, and 7.0 mL of 50% aqueous hydroxylamine (100 mmol) in 50 mL of methanol was heated at 68 C for 8 h, then cooled. Sufficient water was added to dissolve the crystals which deposited, and the solution was concentrated under reduced pressure to remove methanol. The resulting mixture was brought to pH ~10 with aq. NaOH and then extracted with several portions of dichloromethane. The organic phase was dried over $Na_2SO_4$ and then concentrated under reduced pressure to afford 4.15 g (96%) of the title amine as a nearly colorless oil, of sufficient purity for the subsequent reaction. ¹H NMR (400 MHz, CHLOROFORM-d) δ ppm 1.42-1.53 (m, 1H) 1.85 (dd, 1H) 1.88-2.08 (m, 4H) 2.19-2.27 (m, 1H) 2.46 (dd, J=14.5, 8.3 Hz, 1H) 3.97-4.02 (m, 1H) 4.70 (s, 1H) 5.16 (s, 2H) 5.84 (dd, J=5.6, 1.6 Hz, 1H) 5.98 (dd, J=5.6, 2.1 Hz, 1H) 7.31-7.38 (m, 5H). LC-MS ES+ 288.2.

Step 4. 1,5-Anhydro-3-{[(1S,4R)-4-[(benzyloxy)carbonyl]-4-(1-hydroxycyclobutyl)cyclopent-2-en-1-yl]amino}-2,3-dideoxy-4-O-methyl-D-erythro-pentitol

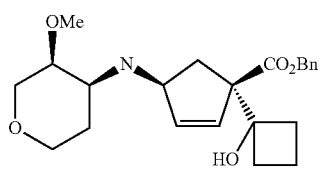

A solution of 3.83 g (13.3 mmol) of benzyl (1R,4S)-4-amino-1-(1-hydroxycyclobutyl)cyclopent-2-ene-1-carboxylate (Preparation SRT-0235) and 1.89 g (14.5 mmol) of (3R)-3-methoxytetrahydro-4H-pyran-4-one in 26 mL of dichloromethane was stirred with activated 3 A molecular sieves for 10 min, then cooled to 0 C. Sodium triacetoxyborohydride (3.35 g, 15.8 mmol) was added in several portions over 10 min, and the mixture was stirred for 1.5 h. The cloudy mixture was added to dichloromethane and aqueous $NaHCO_3$+NaOH (pH ~14), and the aqueous phase was extracted with several additional portions of dichloromethane. The organic phase was dried ($Na_2SO_4$) and concentrated under reduced pressure. Flash chromatography of the residue on silica using 3-5% methanolic ammonia (7M) in dichloromethane afforded 3.94 g (74%) of the title compound as a yellow oil. ¹H NMR (400 MHz, CHLOROFORM-d) δ ppm 1.41-1.52 (m, 1H) 1.55-1.64 (m, 1H) 1.64-1.79 (m, 2H) 1.86-2.09 (m, 5H) 2.19-2.29 (m, 1H) 2.41 (dd, J=14.2, 7.7 Hz, 1H) 2.84-2.91 (m, 1H) 3.17-3.44 (m, 4H) 3.34 (s, 3H) 3.88-3.96 (m, 2H) 4.00 (dd, J=12.3, 4.4 Hz, 1H) 5.10-5.20 (m, 2H) 5.88-5.93 (m, 1H) 6.00 (dd, J=5.6, 1.9 Hz, 1H) 7.28-7.39 (m, 5H). TLC Rf 0.41 (4% 7M methanolic ammonia in dichloromethane). LC-MS ES+ 402.1.

Step 5. 1,5-Anhydro-3-{[(1S,4R)-4-[(benzyloxy)carbonyl]-4-(1-hydroxycyclobutyl)cyclopent-2-en-1-yl](trifluoroacetyl)amino}-2,3-dideoxy-4-O-methyl-D-erythro-pentitol

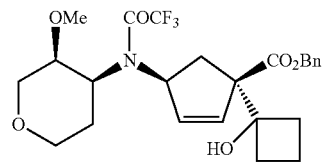

To a cold (0 C), stirred solution of 805 mg (2.00 mmol) of 1,5-anhydro-3-{[(1S,4R)-4-[(benzyloxy)carbonyl]-4-(1-hydroxycyclobutyl)cyclopent-2-en-1-yl]amino}-2,3-dideoxy-4-O-methyl-D-erythro-pentitol and 0.87 mL (5.0 mmol) of diisopropylethylamine in 6 mL of dichloromethane was added dropwise 0.61 mL (4.4 mmol) of trifluoroacetic anhydride. The solution was stirred for 2 h, then stirred with aqueous sodium citrate for 30 min. The organic phase was separated, dried ($Na_2SO_4$), and concentrated under reduced pressure to 1.36 g of brown oil. This was dissolved in 5 mL of methanol and treated with 2 mL of 7M methanolic ammonia. After 1 h, the solution was concentrated under reduced pressure, and the residue chromatographed on silica using 15-20% ethyl acetate in dichloromethane to provide 1.11 g (111%) of the title compound as an amber oil, still retaining some solvent. ¹H NMR (400 MHz, CHLOROFORM-d) δ ppm 1.37-1.49 (m, 1H) 1.50-1.57 (m, 1H) 1.78-2.00 (m, 3H) 2.01-2.10 (m, 1H) 2.26-2.38 (m, 3H) 2.40-2.53 (m, 1H) 3.10 (br. s., 0H) 3.31 (d, J=13.0 Hz, 1H) 3.39-3.45 (m, 1H) 3.43 (s, 3H) 3.50 (t, J=11.4 Hz, 1H) 3.89 (d, J=11.6 Hz, 1H) 4.06-4.14 (m, 1H) 4.19 (d, J=13.0 Hz, 1H) 5.00 (t, 1H) 5.14 (d, J=12.3 Hz, 1H) 5.30 (d, J=12.3 Hz, 1H) 5.78 (dd, J=5.8, 2.0 Hz, 1H) 6.12 (dd, J=5.8, 2.0 Hz, 1H) 6.57 (br. s., 1H) 7.28-7.42 (m, 5H). TLC Rf 0.34 (25% ethyl acetate in dichloromethane). LC-MS ES+ 498.2.

Step 6. 3-[{(1S,4R)-4-[1-(Acetyloxy)cyclobutyl]-4-[(benzyloxy)carbonyl]cyclopent-2-en-1-yl}(trifluoroacetyl)amino]-1,5-anhydro-2,3-dideoxy-4-O-methyl-D-erythro-pentitol

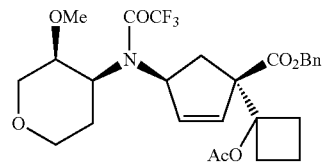

To a stirred solution of 3.58 g (7.2 mmol) of 1,5-anhydro-3-{[(1S,4R)-4-[(benzyloxy)carbonyl]-4-(1-hydroxycyclobutyl)cyclopent-2-en-1-yl](trifluoroacetyl)amino}-2,3-dideoxy-4-O-methyl-D-erythro-pentitol, 1.6 mL (9.2 mmol) of diisopropylethylamine, and 100 mg (0.82 mmol) of DMAP in 10 mL of dichloromethane was added dropwise 5.1 mL (72 mmol) of acetyl chloride. The solution was stirred at ambient temperature for 18 h, then cooled in ice and quenched with aqueous NaHCO₃. The aqueous phase was extracted with additional dichloromethane, and the combined organic phases dried (Na₂SO₄) and concentrated under reduced pressure. Flash chromatography of the residue on silica using 8-10% ethyl acetate in dichloromethane provided 2.63 g (68%) of the title compound as a viscous yellow oil. $^1$H NMR (400 MHz, CHLOROFORM-d) δ ppm 1.35-1.48 (m, 1H) 1.54-1.61 (m, 1H) 1.82-1.94 (m, 1H) 1.88 (s, 3) 2.17-2.26 (m, 1H) 2.34 (dd, J=14.7, 9.9 Hz, 1H) 2.43-2.64 (m, 5H) 3.32 (d, J=12.6 Hz, 1H) 3.37-3.43 (m, 1H) 3.43 (s, 3H) 3.46-3.55 (m, 1H) 3.84-3.94 (m, 1H) 4.09-4.15 (m, 1H) 4.19 (d, J=13.0 Hz, 1H) 4.98-5.05 (m, 1H) 5.08 (d, J=12.3 Hz, 1H) 5.23 (d, J=12.3 Hz, 1H) 5.75 (dd, J=5.8, 2.0 Hz, 1H) 6.16 (dd, J=5.8, 2.4 Hz, 1H) 7.28-7.43 (m, 5H). TLC Rf 0.39 (10% ethyl acetate-dichloromethane). LC-MS ES+ 540.2.

Step 7. 3-[{(1R,3S)-3-[1-(Acetyloxy)cyclobutyl]-3-carboxycyclopentyl}(trifluoroacetyl)amino]-1,5-anhydro-2,3-dideoxy-4-O-methyl-D-erythro-pentitol

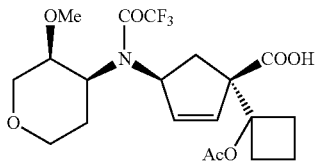

A mixture of 2.62 g (4.86 mmol) of 3-[{(1S,4R)-4-[1-(acetyloxy)cyclobutyl]-4-[(benzyloxy)carbonyl]cyclopent-2-en-1-yl}(trifluoroacetyl)amino]-1,5-anhydro-2,3-dideoxy-4-O-methyl-D-erythro-pentitol and 750 mg each of 5% Pt/C and 5% Pd/C in 10 mL of acetic acid was stirred rapidly under 50 psi hydrogen gas for 18 h, then filtered through diatomaceous earth to remove catalyst. The filtrate was concentrated under reduced pressure, with added toluene to azeotropically remove acetic acid, to provide 2.25 g (103%) of the title compound as a white foam. $^1$H NMR (400 MHz, CHLOROFORM-d) δ ppm 1.50-1.71 (m, 3H) 1.74-1.84 (m, 1H) 2.02 (s, 3H) 2.04-2.17 (m, 1H) 2.34-2.55 (m, 5H) 2.60 (dd, J=14.3, 8.5 Hz, 1H) 2.66-2.81 (m, 2H) 3.30 (d, J=13.0 Hz, 1H) 3.35-3.39 (m, 1H) 3.42 (s, 3H) 3.47-3.56 (m, 1H) 3.83-3.91 (m, 1H) 4.13 (dd, J=11.6, 4.4 Hz, 1H) 4.16-4.23 (m, 1H) 4.26-4.38 (m, 1H). LC-MS ES+ 452.1.

Step 8. 3-{[(1R,3S)-3-[1-(Acetyloxy)cyclobutyl]-3-{[(1S,4S)-5-(tert-butoxycarbonyl)-2,5-diazabicyclo[2.2.1]hept-2-yl]carbonyl}cyclopentyl](trifluoroacetyl)amino}-1,5-anhydro-2,3-dideoxy-4-O-methyl-D-erythro-pentitol

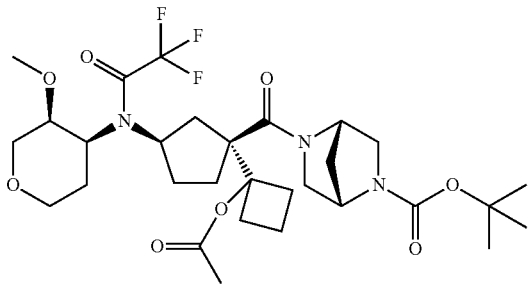

A stirred solution of 1.42 g (3.15 mmol) of 3-[{(1R,3S)-3-[1-(acetyloxy)cyclobutyl]-3-carboxycyclopentyl}(trifluoroacetyl)amino]-1,5-anhydro-2,3-dideoxy-4-O-methyl-D-erythro-pentitol in 6 mL of dichloromethane was treated under argon with 6.5 mL of a 2M dichloromethane solution of oxalyl chloride and 2 drops of dry DMF. After 2 h, the solution was taken to dryness under reduced pressure to give the acid chloride as a yellow foam. This material was dissolved in 8 mL of dichloromethane. To 6 mL of the stirred solution was added 562 mg (2.84 mmol) of (1S,4S)-(−)-2-Boc-2,5-diazabicyclo[2.2.1]heptane and 1.2 mL (6.9 mmol) of diisopropylethylamine. The reaction mixture was stirred at ambient temperature for 18 h, then partitioned between dichloromethane and 1M aqueous citric acid. The organic phase was dried (Na₂SO₄) and concentrated under reduced pressure. Flash chromatography of the residue on silica using 40-50% ethyl acetate in dichloromethane afforded 1.44 g (97%) of the title compound as a white foam. $^1$H NMR (400 MHz, CHLOROFORM-d) δ ppm 1.34-1.62 (m, 12H) 1.73-1.88 (m, 2H) 1.88-2.27 (m, 7H) 2.29-2.41 (m, 1H) 2.40-2.65 (m, 4H) 2.66-2.80 (m, 1H) 3.27-3.64 (m, 9H) 3.81-3.89 (m, 1H) 4.08-4.24 (m, 2H) 4.37-4.60 (m, 2H) 4.85-4.94 (m, 1H). TLC Rf 0.36 (1:1 ethyl acetate in dichloromethane). LC-MS ES+ 632.3.

Step 9. 1,5-Anhydro-3-{[(1R,3S)-3-{[(1S,4S)-5-(tert-butoxycarbonyl)-2,5-diazabicyclo[2.2.1]hept-2-yl]carbonyl}-3-(1-hydroxycyclobutyl)cyclopentyl](trifluoroacetyl)amino}-2,3-dideoxy-4-O-methyl-D-erythro-pentitol

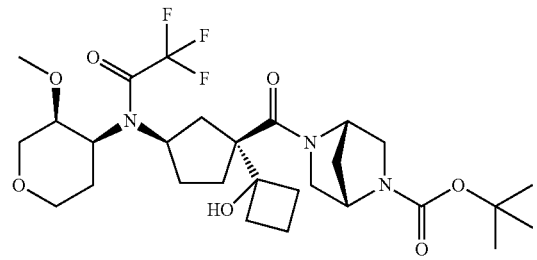

A mixture of 1.43 g (2.26 mmol) of 3-{[(1R,3S)-3-[1-(acetyloxy)cyclobutyl]-3-{[(1S,4S)-5-(tert-butoxycarbonyl)-2,5-diazabicyclo[2.2.1]hept-2-yl]carbonyl}cyclopentyl](trifluoroacetyl)amino}-1,5-anhydro-2,3-dideoxy-4-O-methyl-D-erythro-pentitol and 1.60 g (11.6 mmol) of powdered potassium carbonate in 8 mL of methanol was stirred at ambient temperature for 18 h, then partitioned between dichloromethane and brine, with sufficient water to dissolve solids. The organic phase was dried (Na₂SO₄) and concentrated under reduced pressure. Flash chromatography of the residue on silica using acetate to provide 1.33 g (100%) of the title compound as a white foam. $^1$H NMR (400 MHz, CHLOROFORM-d) δ ppm 1.34-1.62 (m, 10H) 1.66-2.93 (m, 15H) 3.20-3.63 (m, 8H) 3.66-4.03 (m, 3H) 4.06-4.24 (m, 3H) 4.25-4.65 (m, 2H) 4.68-5.29 (m, 1H). TLC Rf 0.33 (EtOAc). LC-MS ES+ 590.3.

Step 10. 1,5-Anhydro-3-{[(1R,3S)-3-{[(1S,4S)-5-(tert-butoxycarbonyl)-2,5-diazabicyclo[2.2.1]hept-2-yl]carbonyl}-3-(1-hydroxycyclobutyl)cyclopentyl]amino}-2,3-dideoxy-4-O-methyl-D-erythro-pentitol

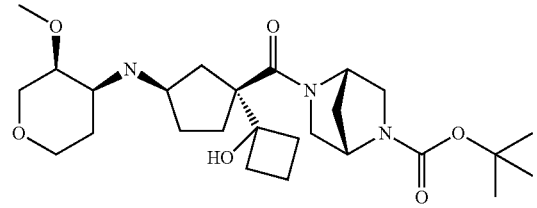

A mixture of 1.31 g (2.23 mmol) of 1,5-anhydro-3-{[(1R,3S)-3-{[(1S,4S)-5-(tert-butoxycarbonyl)-2,5-diazabicyclo[2.2.1]hept-2-yl]carbonyl}-3-(1-hydroxycyclobutyl)cyclopentyl](trifluoroacetyl)amino}-2,3-dideoxy-4-O-methyl-D-erythro-pentitol and 860 mg (23 mmol) of sodium borohydride in 6.3 mL of ethanol was stirred at ambient temperature for 18 h, then partitioned between water and dichloromethane. The aqueous phase was extracted with additional dichloromethane, and the combined organic phase dried (Na$_2$SO$_4$) and concentrated under reduced pressure. Flash chromatography on silica using 6-15% methanol in dichloromethane afforded 1.08 g (98%) of the title compound as a white foam. $^1$H NMR (400 MHz, CHLOROFORM-d) δ ppm 1.42-1.47 (m, 9H) 1.56-2.35 (m, 14H) 2.72 (br. s., 1H) 3.11-3.68 (m, 10H) 3.90-3.98 (m, 1H) 4.08 (dd, J=12.6, 2.7 Hz, 1H) 4.38-4.58 (m, 1H) 4.84-5.16 (m, 1H). LC-MS ES+ 494.3. HRMS calculated for C$_{26}$H$_{43}$N$_3$O$_6$: 494.3230; found: 494.3260.

Step 11. 1,5-Anhydro-2,3-dideoxy-3-{[(1R,3S)-3-[(1S,4S)-2,5-diazabicyclo[2.2.1]hept-2-ylcarbonyl]-3-(1-hydroxycyclobutyl)cyclopentyl]amino}-4-O-methyl-D-erythro-pentitol dihydrochloride

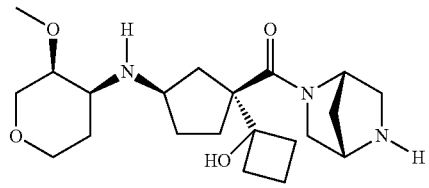

To 902 mg (1.827 mmol) of 1,5-anhydro-3-{[(1R,3S)-3-{[(1S,4S)-5-(tert-butoxycarbonyl)-2,5-diazabicyclo[2.2.1]hept-2-yl]carbonyl}-3-(1-hydroxycyclobutyl)cyclopentyl]amino}-2,3-dideoxy-4-O-methyl-D-erythro-pentitol was added 10 mL of 4M HCl in dioxane, and a few drops of methanol sufficient to give a clear solution. The solution was stirred at ambient temperature for 45 minutes, then concentrated under reduced pressure to give 973 mg of the intermediate salt as a foam. $^1$H NMR (400 MHz, MeOD) δ ppm 1.57-1.70 (m, 1 H) 1.73-1.93 (m, 4H) 1.93-2.10 (m, 4H) 2.14-2.28 (m, 2H) 2.29-2.44 (m, 3H) 2.46-2.59 (m, 2H) 3.35-3.77 (m, 12H) 3.98 (dd, J=11.6, 4.4 Hz, 1H) 4.26 (d, J=13.3 Hz, 1H) 4.45 (s, 1H) 5.21 (br. s., 1H). LC-MS ES+ 394.2.

Example 45

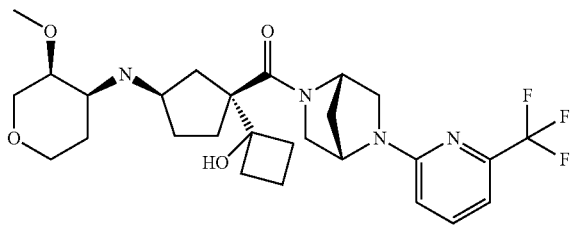

1,5-Anhydro-2,3-dideoxy-3-{[(1R,3S)-3-(1-hydroxycyclobutyl)-3-({(1S,4S)-5-[6-(trifluoromethyl)pyridin-2-yl]-2,5-diazabicyclo[2.2.1]hept-2-yl}carbonyl)cyclopentyl]amino}-4-O-methyl-D-erythro-pentitol A solution of 93 mg (0.20 mmol) of 1,5-anhydro-2,3-dideoxy-3-{[(1R,3S)-3-[(1S,4S)-2,5-diazabicyclo[2.2.1]hept-2-ylcarbonyl]-3-(1-hydroxycyclobutyl)cyclopentyl]amino}-4-O-methyl-D-erythro-pentitol dihydrochloride, 91 mg (0.49 mmol) of 2-chloro-6-trifluoromethylpyridine, and 0.14 mL (0.80 mmol) of diisopropylethylamine in 0.5 mL of DMSO was heated at 80 C for 18 h, then cooled and partitioned between ethyl acetate and water. The organic phase was dried (Na$_2$SO$_4$) and concentrated under reduced pressure. The crude material was purified by preparative RP-HPLC using as the mobile phase acetonitrile-water containing 0.05% TFA. $^1$H NMR (400 MHz, CHLOROFORM-d) δ ppm 1.46-2.52 (m, 16H) 3.26-3.54 (m, 8H) 3.53-3.92 (m, 4H) 4.02 (dd, J=11.8, 4.3 Hz, 1H) 4.22 (d, J=13.0 Hz, 1H) 5.01 (d, J=14.3 Hz, 2H) 6.47 (d, J=8.5 Hz, 1H) 6.93 (d, J=7.5 Hz, 1H) 7.56 (t, J=8.0 Hz, 1H). HRMS calculated for C$_{27}$H$_{37}$N$_4$O$_4$F$_3$: 539.2845; found: 539.2894.

Example 46

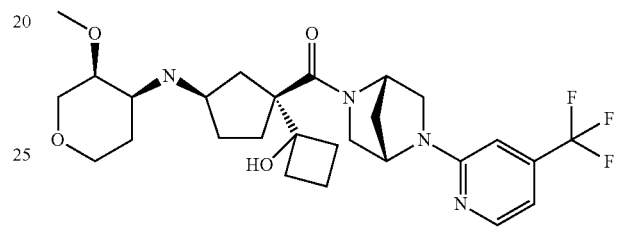

1,5-Anhydro-2,3-dideoxy-3-{[(1R,3S)-3-(1-hydroxycyclobutyl)-3-({(1S,4S)-5-[4-(trifluoromethyl)pyridin-2-yl]-2,5-diazabicyclo[2.2.1]hept-2-yl}carbonyl)cyclopentyl]amino}-4-O-methyl-D-erythro-pentitol The title compound was prepared in a fashion analogous to that described in Preparation Ex. 45. $^1$H NMR (400 MHz, CHLOROFORM-d) δ ppm 1.57-2.31 (m, 14H) 2.33-2.47 (m, 2H) 2.49-2.62 (m, 1H) 3.28-3.54 (m, 7H) 3.57-3.91 (m, 4H) 4.02 (dd, J=11.8, 4.3 Hz, 1H) 4.22 (d, J=13.3 Hz, 1H) 5.07 (br. s., 1H) 5.25 (s, 1H) 6.88-6.96 (m, 2H) 8.14 (d, J=6.5 Hz, 1H). HRMS calculated for C27H37N4O4F3; 539.2845; found: 539.2894.

Example 47

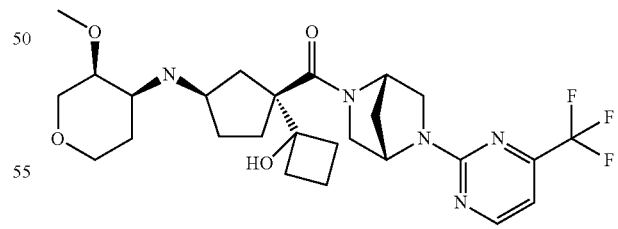

1,5-Anhydro-2,3-dideoxy-3-{[(1R,3S)-3-(1-hydroxycyclobutyl)-3-({(1S,4S)-5-[4-(trifluoromethyl)pyrimidin-2-yl]-2,5-diazabicyclo[2.2.1]hept-2-yl}carbonyl)cyclopentyl]amino}-4-O-methyl-D-erythro-pentitol The title compound was prepared in a fashion analogous to that described in Preparation Example 45. $^1$H NMR (400

MHz, CHLOROFORM-d) δ ppm 1.65-2.51 (m, 15H) 2.52-2.64 (m, 1H) 3.35 (s, 3H) 3.44 (d, J=13.7 Hz, 1H) 3.49-3.98 (m, 7H) 4.19 (dd, J=11.4, 4.6 Hz, 1H) 4.35 (d, J=14.0 Hz, 1H) 5.07-5.48 (m, 2H) 7.16 (d, J=6.5 Hz, 1H) 8.49 (d, J=6.5 Hz, 1H). HRMS calculated for C26H36N5O4F3: 540.2797; found: 540.2812.

Example 48

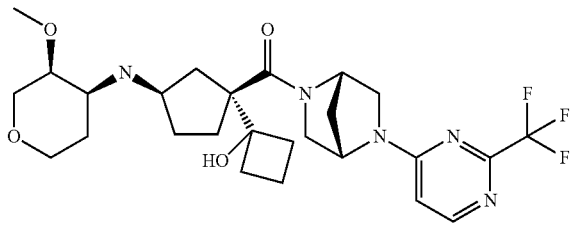

1,5-Anhydro-2,3-dideoxy-3-{[(1R,3S)-3-(1-hydroxycyclobutyl)-3-({(1S,4S)-5-[2-(trifluoromethyl)pyrimidin-4-yl]-2,5-diazabicyclo[2.2.1]hept-2-yl}carbonyl)cyclopentyl]amino}-4-O-methyl-D-erythro-pentitol The title compound was prepared in a fashion analogous to that described in Preparation Example 45. ¹H NMR (400 MHz, CHLOROFORM-d) δ ppm 1.57-2.53 (m, 16H) 3.31 (d, J=13.3 Hz, 1H) 3.35-3.79 (m, 10H) 4.03 (dd, J=11.4, 4.3 Hz, 1H) 4.23 (d, J=12.6 Hz, 1H) 5.11 (s, 1H) 5.29 (br. s., 1H) 6.23-6.75 (m, 2H) 8.30 (d, J=6.1 Hz, 1H). HRMS calculated for C26H36N5O4F3: 540.2797; found: 540.2891.

Example 49

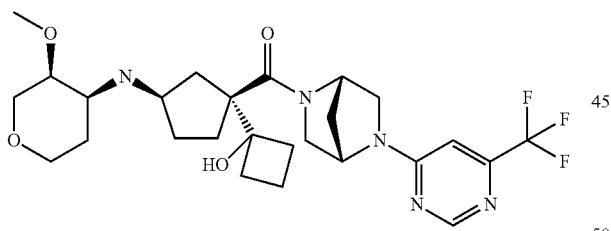

1,5-anhydro-2,3-dideoxy-3-{[(1R,3S)-3-(1-hydroxycyclobutyl)-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol The title compound was prepared in a fashion analogous to that described in Preparation Example 45. ¹H NMR (400 MHz, CHLOROFORM-d) δ ppm 1.56-2.35 (m, 14H) 2.36-2.44 (m, 1H) 2.45-2.54 (m, 1H) 3.32 (d, J=13.3 Hz, 1H) 3.36-3.92 (m, 10H) 4.04 (dd, J=12.3, 4.1 Hz, 1H) 4.24 (d, J=13.0 Hz, 1H) 5.15 (s, 1H) 5.23-5.30 (m, 1H) 6.45-7.05 (m, 3H) 8.67 (s, 1H). HRMS calculated for C26H36N5O4F3: 540.2797; found: 540.2830.

Example 50

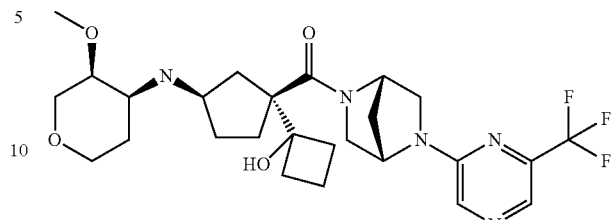

1,5-Anhydro-2,3-dideoxy-3-{[(1R,3S)-3-(1-hydroxycyclobutyl)-3-({(1S,4S)-5-[6-(trifluoromethyl)pyrazin-2-yl]-2,5-diazabicyclo[2.2.1]hept-2-yl}carbonyl)cyclopentyl]amino}-4-O-methyl-D-erythro-pentitol A solution of 93 mg (0.20 mmol) of 1,5-anhydro-2,3-dideoxy-3-{[(1R,3S)-3-[(1S,4S)-2,5-diazabicyclo[2.2.1]hept-2-ylcarbonyl]-3-(1-hydroxycyclobutyl)cyclopentyl]amino}-4-O-methyl-D-erythro-pentitol dihydrochloride 121 mg (0.442 mmol) of 2-iodo-6-trifluoromethylpyrazine, 326 mg (1.0 mmol) of cesium carbonate, 24 mg (40 umol) of XantPhos, and 16 mg (28 umol) of tris(dibenzylideneacetone)palladium (0) in 0.8 mL of dioxane and 0.4 mL of DMSO was heated at 80 C under argon for 18 h, then cooled and partitioned between ethyl acetate and water. The organic phase was dried (Na₂SO₄) and concentrated under reduced pressure. Flash chromatography of the residue on silica using 0-2-4% methanolic ammonia and 3% methanol in dichloromethane afforded 89 mg (82%) of the title compound. ¹H NMR (400 MHz, CHLOROFORM-d) δ ppm 1.51-2.40 (m, 16H) 2.65-2.74 (m, 1H) 3.09-3.49 (m, 10H) 3.54 (d, J=9.6 Hz, 1H) 3.61-3.80 (m, 2H) 3.88-3.96 (m, 1H) 4.06 (dd, J=12.5, 2.9 Hz, 1H) 4.96 (br. s., 1H) 5.21 (br. s., 1H) 8.02 (s, 1H) 8.15 (s, 1H). HRMS calculated for C26H36N5O4F3: 540.2797; found: 540.2896.

Example 51

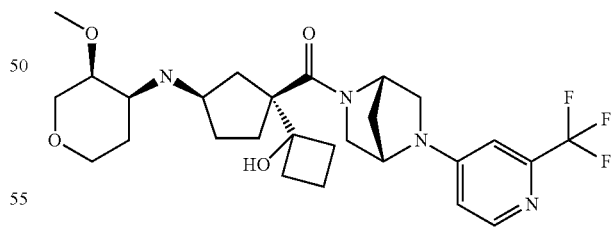

1,5-Anhydro-2,3-dideoxy-3-{[(1R,3S)-3-(1-hydroxycyclobutyl)-3-({(1S,4S)-5-[2-(trifluoromethyl)pyridin-4-yl]-2,5-diazabicyclo[2.2.1]hept-2-yl}carbonyl)cyclopentyl]amino}-4-O-methyl-D-erythro-pentitol The title compound was prepared in a fashion analogous to that described in Example 45. ¹H NMR (400 MHz, CHLO- ROFORM-d) δ ppm 1.51-2.40 (m, 18H) 2.65-2.73 (m, 1H) 3.04-3.47 (m, 8H) 3.59 (d, J=8.5 Hz, 1H) 3.70 (d, J=9.9 Hz, 1H) 3.86-3.95 (m, 1H) 4.05 (dd, J=12.3, 2.4 Hz, 1H) 4.52 (s, 1H) 5.17 (br. s., 1H) 6.48 (br. s., 1H) 6.72 (br. s., 1H) 8.26 (d, J=5.8 Hz, 1H). HRMS calculated for C27H37N4O4F3: 539.2845; found: 539.2979.

Example 52

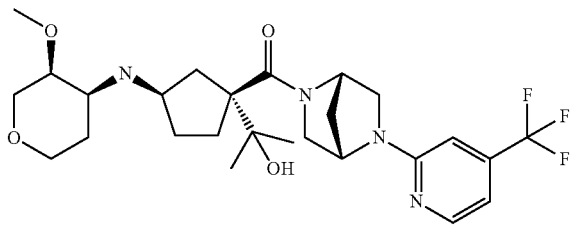

1,5-Anhydro-2,3-dideoxy-3-{[3-(1-hydroxy-1-methylethyl)-3-({5-[4-(trifluoromethyl)pyridin-2-yl]-2,5-diazabicyclo[2.2.1]hept-2-yl}carbonyl)cyclopentyl]amino}-4-O-methylpentitol Step 1. Benzyl 4-(2,5-dimethyl-1H-pyrrol-1-yl)-1-(1-hydroxy-1-methylethyl)cyclopent-2-ene-1-carboxylate

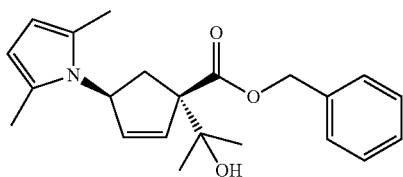

The title compound was prepared in a manner analogous to that described in Example 45, Step 2 above. $^1$H NMR (400 MHz, CHLOROFORM-d) δ ppm 1.18 (s, 3H) 1.22 (s, 3H) 2.11 (s, 6H) 2.22 (dd, J=14.7, 7.5 Hz, 1H) 2.88 (dd, J=14.7, 8.5 Hz, 1H) 3.43 (s, 1H) 5.15-5.23 (m, 2H) 5.24-5.31 (m, 1H) 5.71 (s, 2H) 5.99 (dd, 1H) 6.03 (dd, 1H) 7.30-7.40 (m, 5H). TLC Rf 0.29 (30% ethyl acetate in hexane). LC-MS ES+ 354.2.

Step 2 Benzyl 4-amino-1-(1-hydroxy-1-methylethyl)cyclopent-2-ene-1-carboxylate

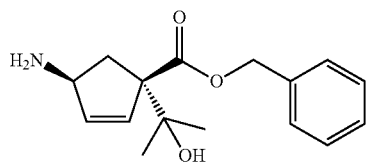

The title compound was prepared in a manner analogous to that described in Example 45, Step 3 above. $^1$H NMR (400 MHz, CHLOROFORM-d) δ ppm 1.11 (s, 3H) 1.14 (s, 3H) 1.81 (dd, J=14.5, 4.9 Hz, 1H) 1.85-1.92 (m, 1H) 2.67 (dd, J=14.3, 8.2 Hz, 1H) 3.97-4.03 (m, 1H) 5.18 (s, 2H) 5.83 (dd, 1H) 5.89 (dd, 1H) 7.32-7.42 (m, 5H). LC-MS ES+ 276.2.

Step 3 1,5-Anhydro-3-({4-[(benzyloxy)carbonyl]-4-(1-hydroxy-1-methylethyl)cyclopent-2-en-1-yl}amino)-2,3-dideoxy-4-O-methylpentitol

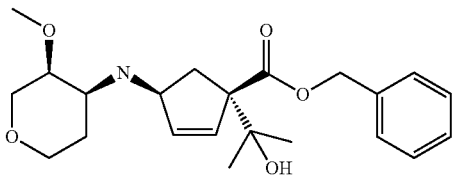

The title compound was prepared in a manner analogous to that described in Example 45, step 4 above. $^1$H NMR (400 MHz, CHLOROFORM-d) δ ppm 1.11 (s, 3H) 1.15 (s, 3H) 1.41-1.66 (m, 2H) 1.68-1.80 (m, 1H) 1.87-1.94 (m, 1H) 2.56-2.65 (m, 1H) 2.82-2.89 (m, 1H) 3.24-3.46 (m, 7H) 3.87-3.97 (m, 2H) 3.98-4.07 (m, 1H) 5.11-5.21 (m, 2H) 5.84-5.97 (m, 2H) 7.30-7.41 (m, 5H). TLC Rf 0.34 (4% methanolic ammonia in dichloromethane). LC-MS ES+ 390.2.

Step 4. 1,5-Anhydro-3-[{4-[(benzyloxy)carbonyl]-4-(1-hydroxy-1-methylethyl)cyclopent-2-en-1-yl}(trifluoroacetyl)amino]-2,3-dideoxy-4-O-methylpentitol

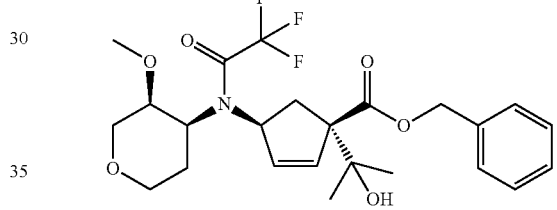

The title compound was prepared in a manner analogous to that described in example 45, step 5 above. $^1$H NMR (400 MHz, CHLOROFORM-d) δ ppm 1.35-1.75 (m, 2H) 1.78-2.08 (m, 4H) 2.24-2.54 (m, 4H) 3.31 (d, J=12.6 Hz, 1H) 3.38-3.45 (m, 2H) 3.43 (s, 3H) 3.45-3.55 (m, 1H) 3.84-3.94 (m, 1H) 4.07-4.14 (m, 1H) 4.19 (d, J=13.0 Hz, 1H) 4.95-5.05 (m, 1H) 5.14 (d, J=12.3 Hz, 1H) 5.31 (d, 1H) 5.78 (dd, J=5.6, 2.2 Hz, 1H) 6.12 (dd, J=5.8, 2.4 Hz, 1H) 7.27-7.44 (m, 5H). Rf ~0.34 (25% ethyl acetate-dichloromethane). LC-MS ES+ 498.2.

Step 5. 3-[{4-[1-(acetyloxy)-1-methylethyl]-4-[(benzyloxy)carbonyl]cyclopent-2-en-1-yl}(trifluoroacetyl)amino]-1,5-anhydro-2,3-dideoxy-4-O-methylpentitol

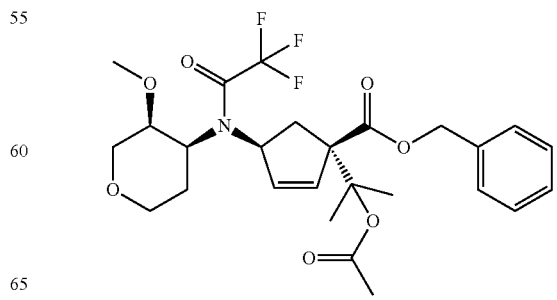

The title compound was prepared in a manner analogous to that described in example 45, step 6 above. ¹H NMR (400 MHz, CHLOROFORM-d) δ ppm 1.49 (s, 3H) 1.53-1.61 (m, 4H) 1.82-1.86 (m, 3H) 2.38-2.57 (m, 2H) 3.32 (d, J=13.0 Hz, 1H) 3.37-3.44 (m, 3H) 3.45-3.56 (m, 2H) 3.84-3.95 (m, 1H) 4.05-4.23 (m, 2H) 4.93-5.04 (m, 1H) 5.08-5.15 (m, 1H) 5.26-5.36 (m, 3H) 6.11 (dd, J=5.8, 2.4 Hz, 1H) 7.28-7.42 (m, 5H). TLC Rf 0.29 (40% ethyl acetate-hexane). LC-MS ES+ 550.2 for M+Na.

Step 6. 3-[{3-[1-(Acetyloxy)-1-methylethyl]-3-carboxycyclopentyl}(trifluoroacetyl)amino]-1,5-anhydro-2,3-dideoxy-4-O-methylpentitol

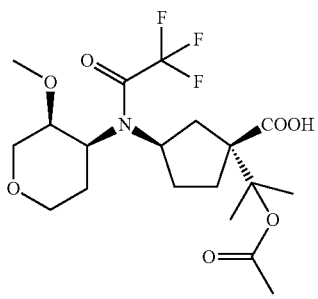

The title compound was prepared in a manner analogous to that described in example 45, step 7 above. ¹H NMR (400 MHz, CHLOROFORM-d) δ ppm 0.86 (none, 1H) 1.51-1.91 (m, 10H) 2.02-2.04 (m, 3H) 2.24-2.54 (m, 3H) 3.31 (d, J=13.0 Hz, 1H) 3.37 (br. s., 1H) 3.41-3.46 (m, 3H) 3.46-3.56 (m, 1H) 3.82-3.91 (m, 1H) 4.08-4.16 (m, 1H) 4.16-4.23 (m, 1H) 4.25-4.39 (m, 1H). LC-MS ES+ 440.2.

Step 7. 3-[(3-[1-(Acetyloxy)-1-methylethyl]-{[5-(tert-butoxycarbonyl)-2,5-diazabicyclo[2.2.1]hept-2-yl]carbonyl}cyclopentyl)(trifluoroacetyl)amino]-1,5-anhydro-2,3-dideoxy-4-O-methylpentitol

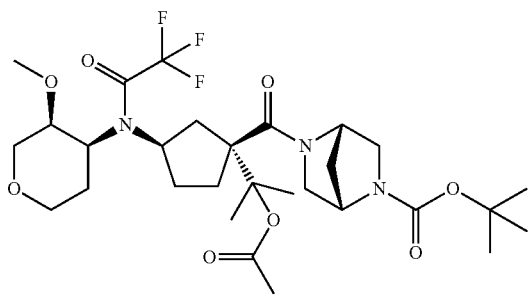

The title compound was prepared in a manner analogous to that described in example 45, step 8 above. ¹H NMR (400 MHz, CHLOROFORM-d) δ ppm 1.35-1.51 (m, 9H) 1.54-1.66 (m, 6H) 1.72-1.87 (m, 2H) 1.97-2.33 (m, 7H) 2.36-2.65 (m, 2H) 3.25-3.68 (m, 9H) 3.80-3.90 (m, 1H) 4.06-4.25 (m, 2H) 4.34-4.64 (m, 2H) 4.88-4.99 (m, 1H). TLC Rf 0.38. LC-MS ES+ 642.3 (M+Na).

Step 8. 1,5-Anhydro-3-{[3-{[5-(tert-butoxycarbonyl)-2,5-diazabicyclo[2.2.1]hept-2-yl]carbonyl}-3-(1-hydroxy-1-methylethyl)cyclopentyl](trifluoroacetyl)amino}-2,3-dideoxy-4-O-methylpentitol

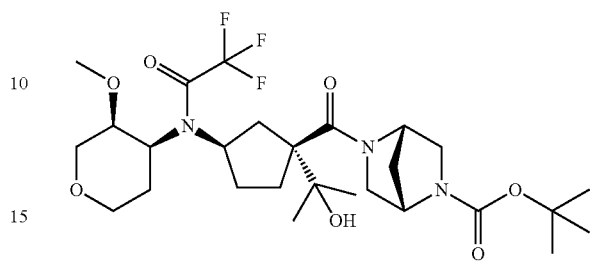

The title compound was prepared in a manner analogous to that described in example 45, Step 9 above. ¹H NMR (400 MHz, CHLOROFORM-d) δ ppm 1.08-1.28 (m, 5H) 1.36-2.77 (m, 18H) 3.25-3.57 (m, 8H) 3.68-3.91 (m, 2H) 4.06-4.24 (m, 2H) 4.37-4.73 (m, 2H) 4.82-5.00 (m, 1H). TLC Rf 0.30 (2% MeOH in ethyl acetate). LC-MS ES+ 578.3.

Step 9. 1,5-anhydro-3-{[3-{[5-(tert-butoxycarbonyl)-2,5-diazabicyclo[2.2.1]hept-2-yl]carbonyl}-3-(1-hydroxy-1-methylethyl)cyclopentyl]amino}-2,3-dideoxy-4-O-methylpentitol

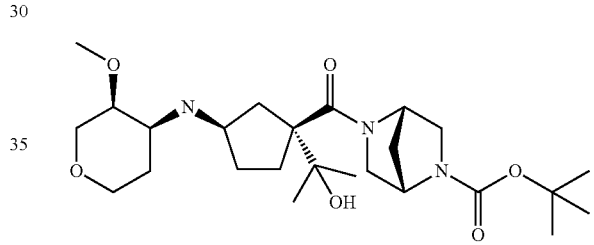

The title compound was prepared in a manner analogous to that described in example 45, step 10. ¹H NMR (400 MHz, CHLOROFORM-d) δ ppm 1.10-1.26 (m, 6H) 1.37-1.90 (m, 16H) 2.23-2.52 (m, 2H) 2.63-2.74 (m, 1H) 3.10-3.72 (m, 10H) 3.84-3.97 (m, 1H) 4.03-4.12 (m, 1H) 4.34-4.62 (m, 1H) 4.80-4.99 (m, 1H). TLC Rf 0.19 (4% methanolic ammonia in dichloromethane). HRMS calculated for C25H43N3O6: 482.3230; found: 482.3276.

Step 10 1,5-Anhydro-2,3-dideoxy-3-{[3-(2,5-diazabicyclo[2.2.1]hept-2-ylcarbonyl)-3-(1-hydroxy-1-methylethyl)cyclopentyl]amino}-4-O-methylpentitol

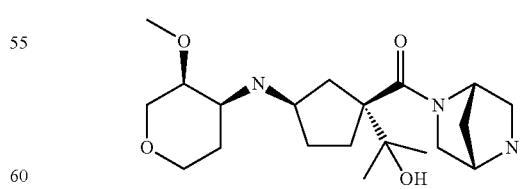

The title compound was prepared in a manner analogous to that described in example 45, step 11 above. ¹H NMR (400 MHz, CD3OD) δ ppm 1.16 (s, 3H) 1.23-1.25 (m, 3H) 1.62-2.34 (m, 7H) 2.66 (br. s., 2H) 3.33-3.68 (m, 14H) 3.98 (dd, J=11.8, 4.6 Hz, 1H) 4.26 (d, J=13.3 Hz, 1H) 4.44 (s, 1H). LC-MS ES+ 382.3.

Example 52

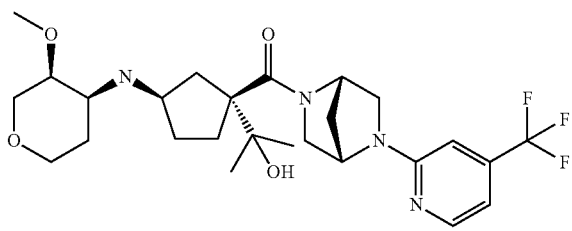

1,5-Anhydro-2,3-dideoxy-3-{[3-(1-hydroxy-1-methylethyl)-3-({5-[4-(trifluoromethyl)pyridin-2-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, DMSO-$d_6$) δ ppm 1.00-1.20 (m, 6H) 1.48-1.60 (m, 1H) 1.65-2.47 (m, 8H) 3.13-3.22 (m, 1H) 3.23-3.54 (m, 8H) 3.55-3.64 (m, 1H) 3.80-3.90 (m, 1H) 4.08-4.16 (m, 1H) 4.87-5.02 (m, 1H) 5.15-5.26 (m, 1H) 6.84 (d, J=5.1 Hz, 1H) 8.28 (d, J=5.5 Hz, 1H). HRMS calculated for C26H37N4O4F3: 527.2845; found: 527.2939.

Example 53

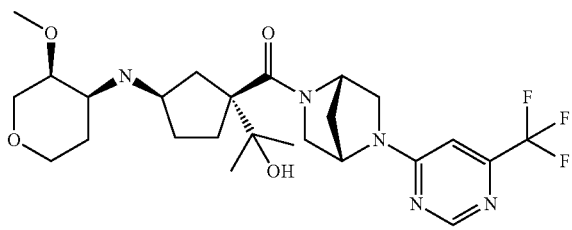

1,5-Anhydro-2,3-dideoxy-3-{[3-(1-hydroxy-1-methylethyl)-3-({5-[6-(trifluoromethyl)pyrimidin-4-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, DMSO-$d_6$) δ ppm 0.92-1.19 (m, 6H) 1.48-1.62 (m, 1H) 1.64-2.47 (m, 8H) 3.09-3.68 (m, 10H) 3.81-3.91 (m, 1H) 4.06-4.18 (m, 1H) 4.87-5.04 (m, 1H) 5.09-5.33 (m, 1H) 8.29-8.64 (m, 2H). HRMS calculated for C25H36N5O4F3: 528.2797; found: 528.2812.

Example 54

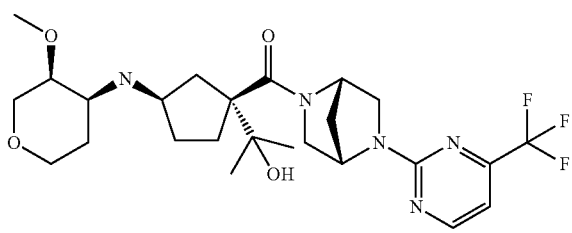

1,5-Anhydro-2,3-dideoxy-3-{[3-(1-hydroxy-1-methylethyl)-3-({5-[4-(trifluoromethyl)pyrimidin-2-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, DMSO-$d_6$) δ ppm 0.99-1.20 (m, 6H) 1.45-1.64 (m, 1H) 1.63-2.18 (m, 7H) 2.25-2.47 (m, 2H) 3.13-3.65 (m, 10H) 3.78-3.91 (m, 1H) 4.12 (dd, 1H) 4.87-5.04 (m, 2H) 5.20 (br. s., 1H) 8.67 (d, J=3.8 Hz, 1H). HRMS calculated for C25H36N5O4F3: 528.2797; found: 528.2856.

Example 55

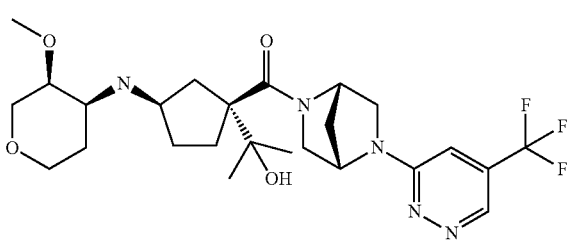

1,5-Anhydro-2,3-dideoxy-3-{[3-(1-hydroxy-1-methylethyl)-3-({5-[5-(trifluoromethyl)pyridazin-3-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, DMSO-$d_6$) δ ppm 0.87-1.20 (m, 7H) 1.49-2.46 (m, 10H) 3.16-3.73 (m, 10H) 3.79-3.89 (m, 1H) 4.08-4.17 (m, 1H) 5.20-5.31 (m, 1H) 8.30-8.61 (m, 2H) 8.84 (s, 1H). HRMS calculated for C25H36N5O4F3: 528.2797; found: 528.2863.

Example 56

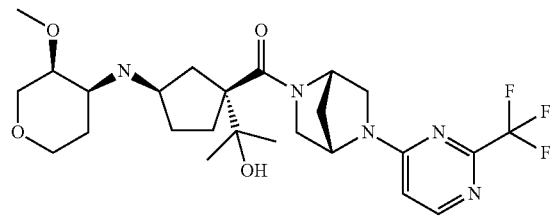

1,5-Anhydro-2,3-dideoxy-3-{[3-(1-hydroxy-1-methylethyl)-3-({5-[2-(trifluoromethyl)pyrimidin-4-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, DMSO-$d_6$) δ ppm 0.96-1.20 (m, 6H) 1.45-2.48 (m, 9H) 3.08-3.66 (m, 10H) 3.80-3.89 (m, 1H) 4.08-4.17 (m, 1H) 4.85-5.11 (m, 1H) 5.16-5.29 (m, 1H) 8.27-8.34 (m, 1H). HRMS calculated for C25H36N5O4F3: 528.2797; found: 528.2927.

Example 57

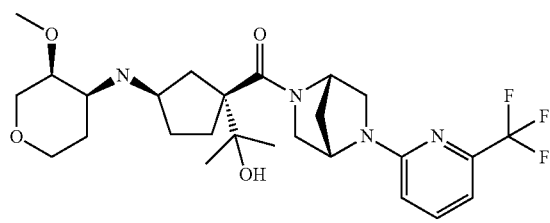

1,5-Anhydro-2,3-dideoxy-3-{[3-(1-hydroxy-1-methylethyl)-3-({5-[6-(trifluoromethyl)pyridin-2-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, CHLOROFORM-d) δ ppm 0.82-1.37 (m, 6H) 1.64-2.67 (m, 10H) 3.19-3.78 (m, 11H) 3.91-4.08 (m, 1H) 4.15-4.28 (m, 1H) 4.93-5.09 (m, 1H) 6.40-6.54 (m, 1H) 6.92 (d, J=7.2 Hz, 1H) 7.55 (t, J=8.0 Hz, 1H). HRMS calculated for C26H37N4O4F3: 527.2845; found: 527.2869.

Example 58

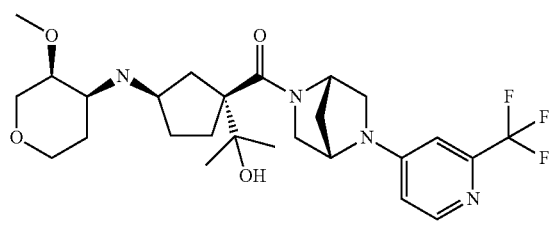

1,5-Anhydro-2,3-dideoxy-3-{[3-(1-hydroxy-1-methylethyl)-3-({5-[2-(trifluoromethyl)pyridin-4-yl]-2,5-diazabicyclo[2.2.1]hept-2-yl}carbonyl)cyclopentyl]amino}-4-O-methylpentitol The title compound was prepared in a manner analogous to that described in Example 45. $^1$H NMR (400 MHz, DMSO-d$_6$) δ ppm 0.99-1.19 (m, 6H) 1.47-1.62 (m, 1H) 1.64-2.46 (m, 9H) 3.08-3.68 (m, 11H) 3.80-3.91 (m, 1H) 4.07-4.18 (m, 1H) 4.75-5.28 (m, 2H) 8.24 (d, J=5.8 Hz, 1H) 8.30-8.77 (m, 2H). HRMS calculated for C26H37N4O4F3: 527.2845; found: 527.2943.

Example 59

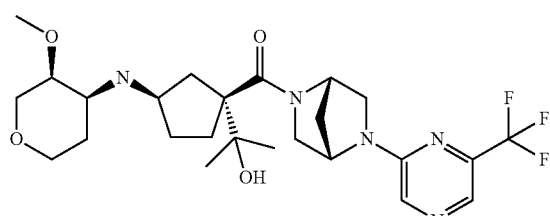

1,5-Anhydro-2,3-dideoxy-3-{[3-(1-hydroxy-1-methylethyl)-3-({5-[6-(trifluoromethyl)pyrazin-2-yl]-2,5-diazabicyclo[2.2.1]hept-2-yl}carbonyl)cyclopentyl]amino}-4-O-methylpentitol The title compound was prepared in a manner analogous to that described in Example 50. $^1$H NMR (400 MHz, DMSO-d$_6$) δ ppm 0.99-1.19 (m, 6H) 1.45-2.48 (m, 10H) 3.15-3.69 (m, 10H) 3.80-3.90 (m, 1H) 4.07-4.17 (m, 1H) 4.88-5.31 (m, 2H) 8.20 (s, 1H) 8.28-8.63 (m, 3H). HRMS calculated for C25H36N5O4F3: 528.2797; found: 528.2905.

Example 60/61

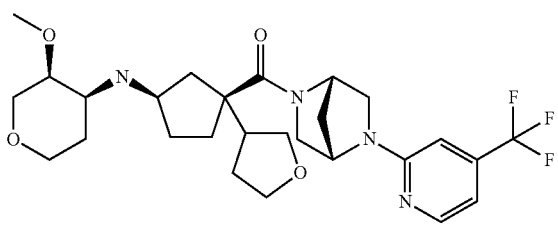

((1S,3R)-3-((3S,4S)-3-methoxy-tetrahydro-2H-pyran-4-ylamino)-1-(tetrahydrofuran-3-yl)cyclopentyl)((1S,4S)-5-(4-(trifluoromethyl)pyridin-2-yl)-2,5-diaza-bicyclo[2.2.1]heptan-2-yl)methanone $^1$HNMR (400 MHz, CD$_3$OD) δ 8.20 (d, 1H), 7.18 (s, 1H), 6.97 (d, 1H), 5.11 (m, 2H), 4.24 (d, 1H), 3.38-3.99 (m, 17H), 2.87 (m, 1H), 2.65 (m, 1H), 2.48 (m, 1H), 1.90-2.39 (m, 8H), 1.81 (m, 2H), 1.65 (m, 1H).

$^1$HNMR (400 MHz, CD$_3$OD) δ 8.20 (d, 1H), 7.18 (s, 1H), 6.97 (d, 1H), 5.11 (m, 2H), 4.24 (d, 1H), 3.38-3.99 (m, 17H), 2.87 (m, 1H), 2.65 (m, 1H), 2.48 (m, 1H), 1.90-2.39 (m, 8H), 1.81 (m, 2H), 1.65 (m, 1H).

Example 62/63

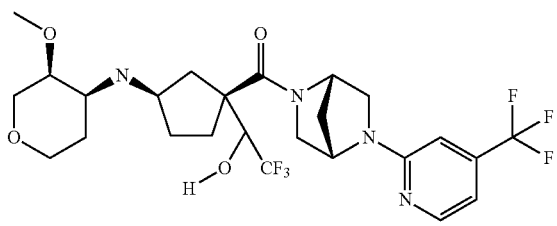

((1S,3R)-3-((3S,4S)-3-methoxy-tetrahydro-2H-pyran-4-ylamino)-1-(2,2,2-trifluoro-1-hydroxyethyl)cyclopentyl)((1S,4S)-5-(4-(trifluoromethyl)pyridin-2-yl)-2,5-diaza-bicyclo[2.2.1]heptan-2-yl)methanone $^1$HNMR (400 MHz, CD3OD) δ 8.23 (d, J=8 Hz, 1H), 6.8 (d, J=8 Hz, 1H), 6.72 (d, J=8 Hz, 1H), 5.0 (m, 1H), 4.2, (m, 1H), 3.85 (m, 2H), 3.6 (m, 1H), 3.52 (m, 1H), 3.30 (s, 3H) 3.4 (m, 4H), 2.7 (m, 2H), 2.4 (m, 1H), 2.0 (m, 4H), 1.8 (m, 4H), 1.6 (m, 4H)

1HNMR (400 MHz, CD3OD) δ 8.23 (d, J=8 Hz, 1H), 6.8 (d, J=8 Hz, 1H), 6.72 (d, J=8 Hz, 1H), 5.0 (m, 1H), 4.2, (m, 1H), 3.85 (m, 2H), 3.6 (m, 1H), 3.30 (s, 3H), 3.52 (m, 1H), 3.4 (m, 4H), 2.7 (m, 2H), 2.4 (m, 1H), 2.0 (m, 4H), 1.8 (m, 4H), 1.6 (m, 4H)

Example 64

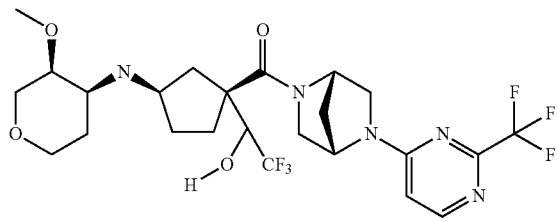

((1S,3R)-3-((3S,4S)-3-methoxy-tetrahydro-2H-pyran-4-ylamino)-1-(2,2,2-trifluoro-1-hydroxyethyl)cyclopentyl)((1S,4S)-5-(2-(trifluoromethyl)pyrimidin-4-yl)-2,5-diaza-bicyclo[2.2.1]heptan-2-yl)methanone ¹HNMR (400 MHz, CD3OD) δ 8.23 (m, 1H), 6.6 (m, 1H), 4.25 (m, 1H), 4.0 (m, 2H), 3.85 (m, 1H), 3.7 (m, 1H) 3.6 (m, 4H), 3.42 (m, 4H), 2.52 (m, 2H), 2.25 (m, 2H), 2.1 (m, 2H) 2.0 (m, 4H), 1.6 (m, 2H)

Example 65

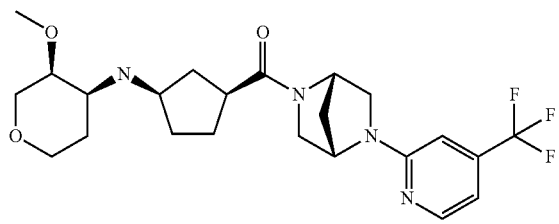

((1S,3R)-3-((3S,4S)-3-methoxy-tetrahydro-2H-pyran-4-ylamino)cyclopentyl)((1S,4S)-5-(4-(trifluoromethyl)pyridin-2-yl)-2,5-diaza-bicyclo[2.2.1]heptan-2-yl)methanone ¹HNMR (400 MHz, CD3OD) δ 8.23 (d, J=8 Hz, 1H), 6.8 (d, J=8 Hz, 1H), 6.72 (d, J=16 Hz, 1H), 5.0 (m, 1H), 4.2, (m, 1H), 3.9 (m, 1H), 3.85 (m, 1H), 3.8 (m, 4H), 3.4 (m, 4H), 3.30 (m, 3H), 3.2 (m, 4H), 2.0 (m, 4H), 1.8 (m, 4H)

Example 66

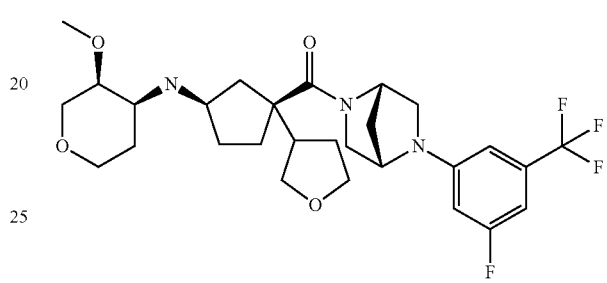

((1S,4S)-5-(3-fluoro-5-(trifluoromethyl)phenyl)-2,5-diaza-bicyclo[2.2.1]heptan-2-yl)((1S,3R)-3-((3S,4S)-3-methoxy-tetrahydro-2H-pyran-4-ylamino)-1-(tetrahydrofuran-3-yl)cyclopentyl)methanone 1HNMR (400 Mhz, CD3OD), δ 6.6 (m, 3H), 5.0 (m, 1H), 4.6 (m, 1H), 4.25 (d, J=4 Hz, 1H), 4.0 (m, 1H), 3.85 (m, 1H), 3.8 (m, 2H), 3.7 (m, 2H), 3.65 (m, 2H) 3.5 (m, 2H), 3.4 (3H), 3.2 (d, J=4 Hz, 2H), 2.8 (m, 1H), 2.6 (m, 1H), 2.5 (m, 1H), 2.35 (m, 1H), 2.2 (m, 1H), 2.1 (m, 2H), 2.05 (m, 2H), 2.0 (m, 2H), 1.8 (m, 2H), 1.6 (m, 2H)

Preparation of Examples 67-71

Scheme. Prep of F-221

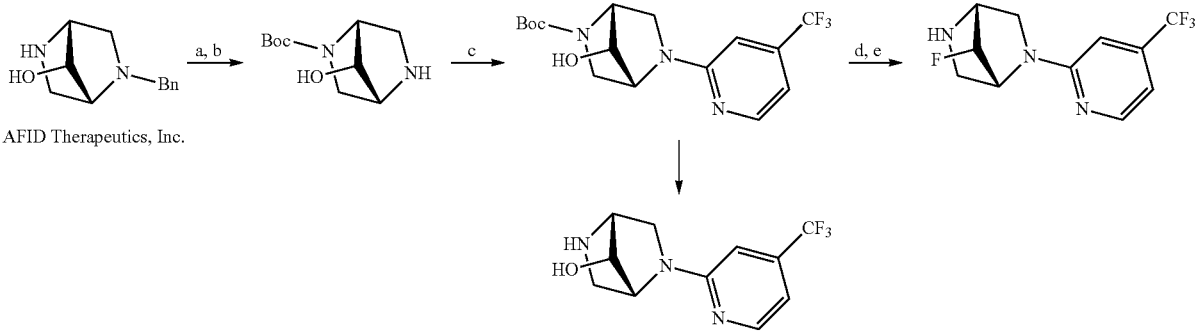

AFID Therapeutics, Inc.

a) Boc₂O, DIPEA; b) NBS, CCl₄ then 10% Pd/C, H₂; c) Cl-pyridine-CF₃, DIPEA, DMF; d) DAST, DCM, 0° C.; e) 4N HCl/dioxane, rt

Step 1. Preparation of (1R,4S)-tert-butyl 7-hydroxy-5-(4-(trifluoromethyl)pyridin-2-yl)-2,5-diaza-bicyclo[2.2.1]heptane-2-carboxylate To a solution of alcohol (2.48 g, 11.6 mmol) in DMSO (30 mL) was added 2-chloro-5-(trifluoromethyl)pyridine (2.0 g, 11.0 mmol) and TEA (3.4 mL, 24.2 mmol). After heating the mixture at 95° C. overnight the mixture was poured into $H_2O$ and the aqueous mixture extracted 2× with ether. The organic extracts were dried ($Na_2SO_4$) and the solvent removed to give an oil, which after chromatography (silica, EtOAc:Heptane) gave the product (1.0 g). LC/MS (M+Na)=382 exp, 382 obs.

Step 2. Preparation of (1R,4S)-tert-butyl 7-fluoro-5-(4-(trifluoromethyl)pyridin-2-yl)-2,5-diaza-bicyclo[2.2.1]heptane-2-carboxylate To a solution of alcohol in DCM at 0° C. was added DAST dropwise. After addition was complete the reaction mixture was allowed to warm to rt and stirred at rt overnight. The reaction mixture was poured into saturated $NaHCO_3$/DCM and the layers separated. The organic layer was collected, dried ($Na_2SO_4$) and the solvent removed to give an oil, which after chromatography (silica, EtOAc:Heptane) gave the desired product (750 mg). LC/MS (M+H)=362.1491 exp, 362.1491 obs. 1H NMR (400 MHz, DMSO-$d_6$) δ ppm 8.31 (1H, d, J=5.5 Hz), 6.85-6.96 (2H, m), 5.35 (1H, d, J=55.6 Hz), 4.90 (1H, br. s.), 4.47 (1H, d, J=22.7 Hz), 3.64 (1H, dd, J=10.2, 1.8 Hz), 3.47-3.57 (1H, m), 3.39-3.46 (1H, m), 3.26-3.32 (1H, m), 1.39 (9H, d, J=12.4 Hz).

Step 3. Preparation of (1S,4R)-7-fluoro-2-(4-(trifluoromethyl)pyridin-2-yl)-2,5-diaza-bicyclo[2.2.1]heptane To a solution of (1R,4S)-tert-butyl 7-fluoro-5-(4-(trifluoromethyl)pyridin-2-yl)-2,5-diaza-bicyclo[2.2.1]heptane-2-carboxylate (700 mg, 1.9 mmol) in dioxane (2 ml) was added 4N HCl/dioxane (5 mL). The reaction mixture was stirred at rt for 5 hr and then diluted with ether to give a precipitate that was filtered and collected to give the product as the HCl salt (506 mg). LC/MS (M+H)=262.0967 exp, 262.1308 obs; 1H NMR (400 MHz, METHANOL-$d_4$) δ ppm 8.26 (1H, d, J=6.1 Hz), 7.40 (1H, s), 7.20 (1H, dd, J=6.3, 1.0 Hz), 5.65 (1H, dd, J=52.4, 1.9 Hz), 5.28 (1H, s), 4.70 (1H, s), 3.92-4.09 (2H, m), 3.66-3.81 (2H, m), 3.62 (1H, s)

Step 4. Preparation of (1S,4R)-7-hydroxy-2-(4-(trifluoromethyl)pyridin-2-yl)-2,5-diaza-bicyclo[2.2.1]heptane To a solution of (1R,4S)-tert-butyl 7-hydroxy-5-(4-(trifluoromethyl)pyridin-2-yl)-2,5-diaza-bicyclo[2.2.1]heptane-2-carboxylate (5 g, 14 mmol) in dioxane (5 ml) was added 4N HCl/dioxane (15 mL). The reaction mixture was stirred at rt for 6 hr and then diluted with ether to give a precipitate that was filtered and collected to give the product as the HCl salt (4.0 g). LC/MS (M+H)=260.0 exp, 260.0 obs; 1H NMR (500 MHz, DMSO-$d_6$) δ ppm 3.42-3.50 (m, 1H) 3.67-3.72 (m, 1H) 3.75-3.82 (m, 1H) 4.16 (br. s., 1H) 4.50 (d, J=1.81 Hz, 1H) 4.72 (br. s., 1H) 6.95 (d, J=5.13 Hz, 2H) 8.31 (d, J=5.43 Hz, 1H) 9.34 (br. s., 1H) 9.75 (br. s., 1H)

Scheme 5

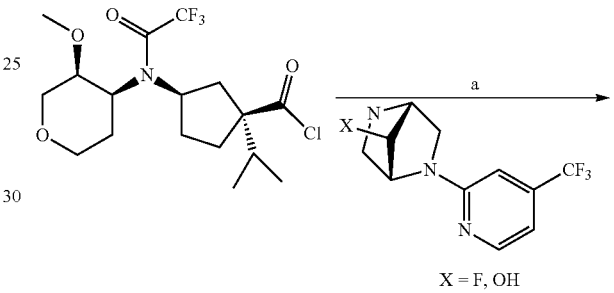

X = F, OH

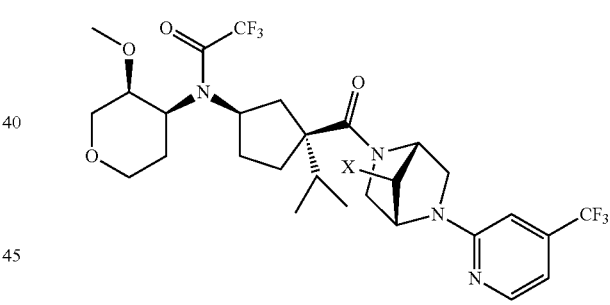

| b
| or c then b

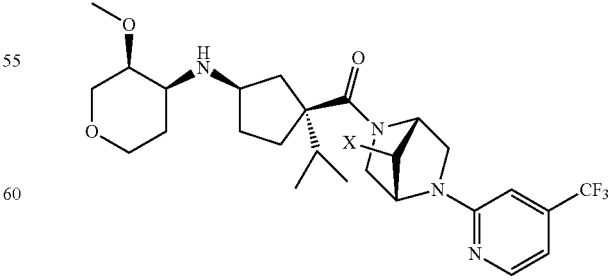

a) DCM, TEA, R1R2NH, rt; b) 50% NaOH, EtOH, rt; c) DAST, DCM, 0° C.

Scheme 6

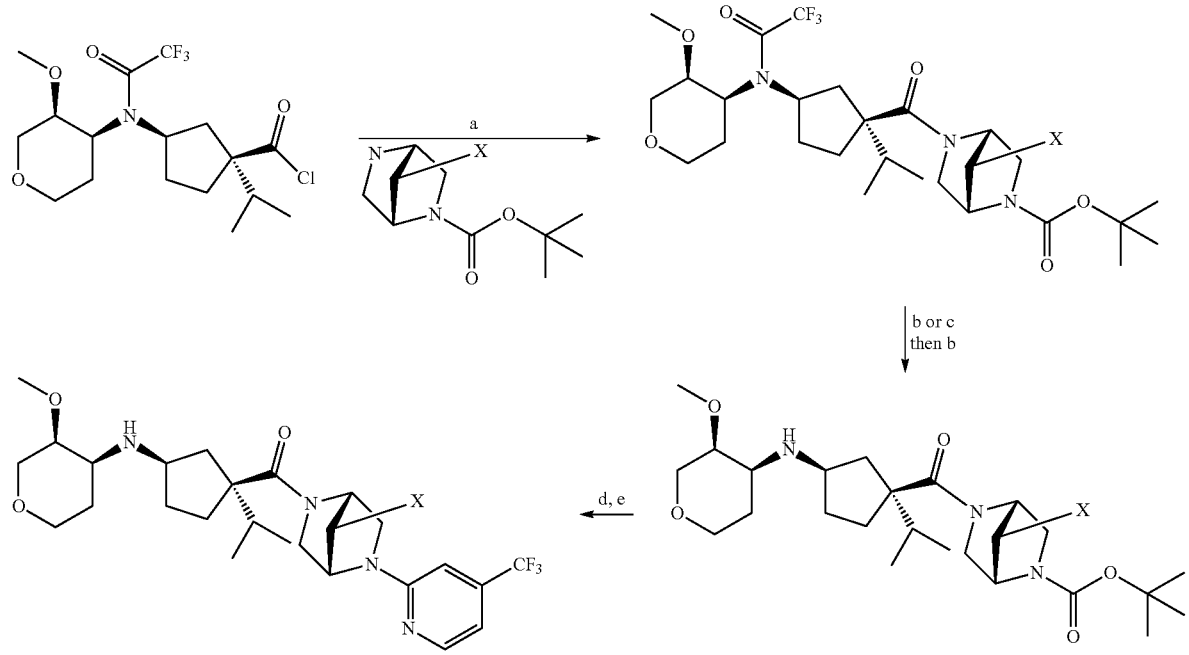

X = F, OH
a) DCM, TEA, R1R2NH, rt;
b) 50% NaOH, EtOH, rt;
c) DAST, DCM, 0° C.;
d) 4N HCl/dioxane;
e) Pyr—Cl Et3N, DMSO, 100° C.

Example 67

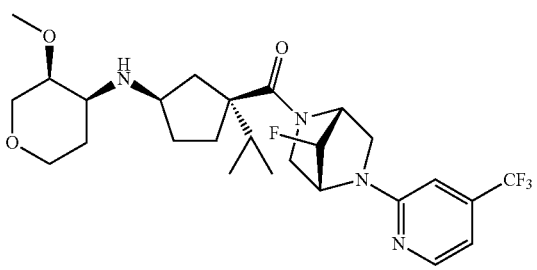

((1R,4R,7S)-7-fluoro-5-(4-(trifluoromethyl)pyridin-2-yl)-2,5-diaza-bicyclo[2.2.1]heptan-2-yl)((1S,3R)-1-isopropyl-3-((3S,4S)-3-methoxy-tetrahydro-2H-pyran-4-ylamino)cyclopentyl)methanone Prepared in a manner analogous to example 1, except using (1R,4R,7R)-7-fluoro-2-(4-(trifluoromethyl)pyridin-2-yl)-2,5-diaza-bicyclo[2.2.1]heptane as the coupling amine. LC/MS (M+H)=529 exp, 529 obs; 1H NMR (400 MHz, DMSO-$d_6$) δ ppm 8.31 (1H, d, J=5.1 Hz), 6.92 (2H, d, J=5.1 Hz), 5.39 (1H, d, J=55.6 Hz), 4.81-4.98 (2H, m), 3.78-3.88 (1H, m), 3.66-3.75 (2H, m), 3.57-3.65 (1H, m), 3.37-3.43 (1H, m), 3.23-3.31 (2H, m), 3.15-3.22 (4H, m), 3.06-3.10 (1H, m), 2.95-3.03 (1H, m), 2.68-2.77 (1H, m), 2.22-2.32 (1H, m), 1.93-2.09 (2H, m), 1.61-1.72 (2H, m), 1.35-1.53 (3H, m), 1.21-1.29 (1H, m), 1.08-1.20 (1H, m), 0.82 (2H, d, J=6.2 Hz), 0.64-0.77 (4H, m)

Example 68

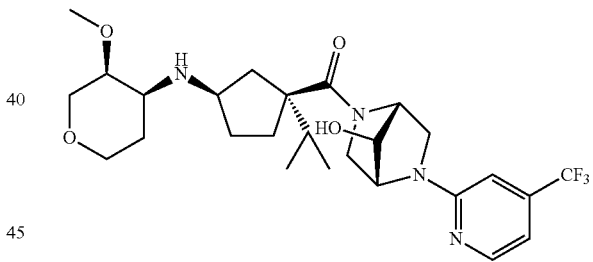

((1R,4R,7S)-7-hydroxy-5-(4-(trifluoromethyl)pyridin-2-yl)-2,5-diaza-bicyclo[2.2.1]heptan-2-yl)((1S,3R)-1-isopropyl-3-((3S,4S)-3-methoxy-tetrahydro-2H-pyran-4-ylamino)cyclopentyl)methanone To a solution of the (1S,3R)-1-isopropyl-3-(2,2,2-trifluoro-N-((3S,4S)-3-methoxy-tetrahydro-2H-pyran-4-yl)acetamido)cyclopentanecarbonyl chloride (185 mg, 0.463 mmol) in $CH_2Cl_2$ (2 mL) was added $Et_3N$ (0.161 ml, 1.16 mmol) and (1R,4R,7R)-7-hydroxy-2-(4-(trifluoromethyl)pyridin-2-yl)-2,5-diaza-bicyclo[2.2.1]heptane (100 mg, 0.386 mmol). The mixture was stirred for 4 hrs. at RT. The solution was then washed with $NaHCO_3$ (1×3 ml), and brine (1×3 ml). The organic layer was then dried over MgSO4, filtered and concentrated, purified by chromatopraphy with (100% EtOAc-70% MeOH/EtOAc) to yield TFA protected product, which was then treated with 2N NaOH (0.5 ml, 1 mmol) in THF (2 ml) at RT for 4 hrs., then purified by chromatography with (100% EtOAc-100% MeOH) to yield 60 mg desired product (30%). LC/MS (M+H)=527.2845 exp, 527.2996 obs; 1H NMR (400 MHz, DMSO-d$_6$) δ ppm 0.64-0.76 (m, 4H) 0.77-0.88 (m, 3H) 1.13 (d, J=1.83 Hz, 1H) 1.34 (br. s., 1H) 1.36-1.48 (m, 3H) 1.66 (dt, J=7.69, 3.84 Hz, 1H) 1.77-1.90 (m, 1H) 1.99 (dt, J=13.55, 6.77 Hz, 2H) 2.29 (dd, J=12.08, 8.05 Hz, 1H) 2.73-2.79 (m, 1H) 2.97-3.04 (m, 1H) 3.07-3.14 (m, 2H) 3.15-3.24 (m, 5H) 3.59 (br. s., 1H) 3.61-3.72 (m, 2H) 3.75-3.88 (m, 1H) 4.26 (d, J=0.73 Hz, 1H) 4.44-4.55 (m, 2H) 5.72 (d, J=3.29 Hz, 1H) 6.75-6.85 (m, 2H) 8.27 (d, J=5.49 Hz, 1H)

Example 69

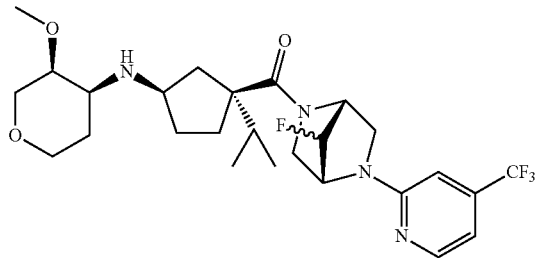

((1R,4R)-7-fluoro-5-(4-(trifluoromethyl)pyridin-2-yl)-2,5-diaza-bicyclo[2.2.1]heptan-2-yl)((1S,3R)-1-isopropyl-3-((3S,4S)-3-methoxy-tetrahydro-2H-pyran-4-ylamino)cyclopentyl)methanone 2,2,2-trifluoro-N-((1R,3S)-3-((1R,4R,7S)-7-hydroxyl-2-(4-(trifluoromethyl)pyridin-2-yl)-2,5-diaza-bicyclo[2.2.1]heptane-5-carbonyl)-3-isopropylcyclopentyl)-N-((3S,4S)-3-methoxy-tetrahydro-2H-pyran-4-yl)acetamide (30 mg, 0.057 mmol) in CH$_2$Cl$_2$ (2 ml) was cooled to 0° C. and DAST (0.025 ml, 0.086 mmol) was added to the solution. The reaction mixture was stirred overnight and purified by chromatography (10% EtOAc to 100% MeOH) to yield desired product (16 mg, 32%). LC/MS (M+H)=529.2802 exp, 529.3112 obs; 1H NMR (400 MHz, DMSO-d$_6$) δ ppm 0.67-0.78 (m, 5H) 0.82 (d, J=6.59 Hz, 3H) 1.23 (br. s., 1H) 1.50 (d, J=3.66 Hz, 3H) 1.75 (d, J=4.39 Hz, 2H) 1.94-2.03 (m, 1H) 2.24-2.32 (m, 1H) 2.98 (s, 1H) 3.12 (br. s., 1H) 3.18-3.23 (m, 4H) 3.31-3.34 (m, 1H) 3.40 (d, J=10.98 Hz, 1H) 3.62 (d, J=12.08 Hz, 1H) 3.72 (d, J=10.62 Hz, 3H) 3.80-3.92 (m, 1H) 4.87 (br. s., 1H) 4.90-4.96 (m, 1H) 5.31 (d, J=1.83 Hz, 1H) 5.40-5.46 (m, 1H) 6.86-6.94 (m, 2H) 8.31 (d, J=5.49 Hz, 1H)

Example 70

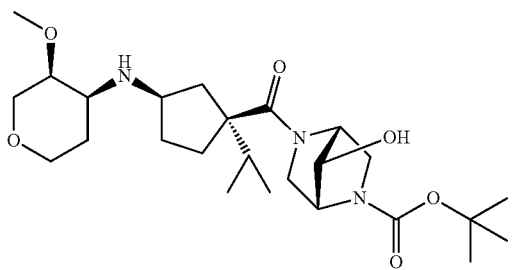

(1R,4R,7S)-tert-butyl 7-hydroxy-5-((1S)-1-isopropyl-3-(3-methoxy-tetrahydro-2H-pyran-4-ylamino)cyclopentanecarbonyl)-2,5-diaza-bicyclo[2.2.1]heptane-2-carboxylate To a solution of the (1S,3R)-1-isopropyl-3-(2,2,2-trifluoro-N-((3S,4S)-3-methoxy-tetrahydro-2H-pyran-4-yl)ac- etamido)cyclopentanecarboxylic acid (0.95 g, 2.5 mmol) in CH$_2$Cl$_2$ (5 mL) under N2 at 0° C. is added oxalyl chloride (623 mg, 4.98 mmol) and DMF (3 drops). The mixture is allowed to warm to RT and stir for 2 hr, It was then concentrated. The acid chloride was redissolved in DCM (10 ml), cooled to 0° C., and treated with (1R,4R,7S)-tert-butyl 7-hydroxy-2,5-diaza-bicyclo[2.2.1]heptane-2-carboxylate (534 mg, 0.249 mmol), followed by Et3N (0.1 ml, 0.75 mmol). The resulting mixture was warmed to RT and stirred for 2 hrs. The solution was then washed with NaHCO$_3$ (1×5 ml), and brine (1×5 ml). The organic layer was then dried over MgSO4, filtered and concentrated, purified by chromatography (100% EtOAc-60% MeOH/EtOAc) to yield crude intermediate which was dried and concentrated. Then it was dissolved in EtOH (2 ml) and treated with NaOH (3 ml, 7.5 mmol) overnight. The reaction mixture was then purified by chromatography (100% EtOAc-100% MeOH) to yield desired product (300 mg, 25%). LC/MS (M+H)=482.3230 exp, 482.3334 obs; 1H NMR (400 MHz, DMSO-d$_6$) δ ppm 0.67 (dd, J=6.95, 3.66 Hz, 3H) 0.80 (dd, J=6.59, 2.93 Hz, 3H) 1.22 (br. s., 1H) 1.35-1.41 (m, 12H) 1.43-1.48 (m, 2H) 1.55-1.68 (m, 2H) 1.85-1.93 (m, 1H) 1.95-2.04 (m, 1H) 2.16-2.28 (m, 1H) 2.66-2.80 (m, 1H) 2.97-3.02 (m, 1H) 3.03-3.10 (m, 2H) 3.17-3.29 (m, 5H) 3.37-3.47 (m, 1H) 3.47-3.58 (m, 1H) 3.61-3.74 (m, 1H) 3.81-3.89 (m, 1H) 3.94-4.04 (m, 2H) 4.24 (br. s., 1H) 5.65-5.77 (m, 1H)

Example 71

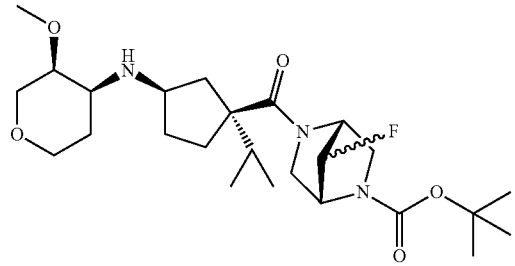

tert-butyl 7-fluoro-5-((1S,3R)-1-isopropyl-3-((3S,4S)-3-methoxy-tetrahydro-2H-pyran-4-ylamino)cyclopentanecarbonyl)-2,5-diaza-bicyclo[2.2.1]heptane-2-carboxylate tert-butyl 7-hydroxy-5-((1S)-1-isopropyl-3-(2,2,2-trifluoro-N-(3-methoxy-tetrahydro-2H-pyran-4-yl)acetamido)cyclopentanecarbonyl)-2,5-diaza-bicyclo[2.2.1]heptane-2-carboxylate (100 mg, 0.173 mmol) in CH$_2$Cl$_2$ (2 ml) was cooled to 0° C. and DAST (0.036 ml, 0.259 mmol) was added to the solution. The reaction mixture was stirred overnight and purified by chromatography (10% EtOAc to 100% MeOH) to yield TFA protected product, which was then treated with 2.5N NaOH (0.014 ml, 0.5 mmol) in THF (2 ml) at RT for 4 hrs., then purified by chromatopraphy with (100% EtOAc-100% MeOH) to yield 12 mg desired product (14%). LC/MS (M+H)=484.3187 exp, 484.3197 obs; 1H NMR (400 MHz, DMSO-d$_6$) δ ppm 0.63-0.72 (m, 3H) 0.81 (dd, J=7.14, 1.65 Hz, 3H) 1.22 (br. s., 1H) 1.36-1.48 (m, 13H) 1.56-1.68 (m, 2H) 1.85-1.96 (m, 2H) 2.16-2.28 (m, 1H) 2.68-2.79 (m, 1H) 2.95-3.05 (m, 1H) 3.15 (br. s., 1H) 3.17-3.29 (m, 7H) 3.52 (d, J=10.62 Hz, 2H) 3.66-3.74 (m, 1H) 3.82-3.90 (m, 1H) 4.27-4.37 (m, 1H) 4.69 (br. s., 1H) 5.08-5.35 (m, 1H)

Biological Data
CCR2 In Vitro Assays

The capacity of the novel compounds of the invention to antagonize chemokine receptor (e.g., CCR2) function can be determined using a suitable screen (e.g., high through-put assay). For example, an agent can be tested in an extracellular acidification assay, calcium flux assay, ligand binding assay or chemotaxis assay (see, for example, Hesselgesser et al., J Biol. Chem. 273(25):15687-15692 (1998); WO 00/05265 and WO 98/02151).

In a suitable assay, a CCR2 protein which can be isolated or recombinantly derived is used which has at least one property, activity or functional characteristic of a mammalian CCR2 protein. The specific property can be a binding property (to, for example, a ligand or inhibitor), a signalling activity (e.g., activation of a mammalian G protein, induction of rapid and transient increase in the concentration of cytosolic free calcium [Ca++]i, cellular response function (e.g., stimulation of chemotaxis or inflammatory mediator release by leukocytes), and the like.

In an example binding assay, a composition containing a CCR2 protein or variant thereof is maintained under conditions suitable for binding. The CCR2 receptor is contacted with a compound to be tested, and binding is detected or measured.

In an example cell-based assay, cells are used which are stably or transiently transfected with a vector or expression cassette having a nucleic acid sequence which encodes the CCR2 receptor. The cells are maintained under conditions appropriate for expression of the receptor and are contacted with an agent under conditions appropriate for binding to occur. Binding can be detected using standard techniques. For example, the extent of binding can be determined relative to a suitable control. Also, a cellular fraction, such as a membrane fraction, containing the receptor can be used in lieu of whole cells.

Detection of binding or complex formation in an assay can be detected directly or indirectly. For example, the agent can be labeled with a suitable label (e.g., fluorescent label, label, isotope label, enzyme label, and the like) and binding can be determined by detection of the label. Specific and/or competitive binding can be assessed by competition or displacement studies, using unlabeled agent or a ligand as a competitor.

The CCR2 antagonist activity of compounds of the invention can be reported as the inhibitor concentration required for 50% inhibition (IC50 values) of specific binding in receptor binding assays using 125I-labeled MCP-1, as ligand, and Peripheral Blood Mononuclear Cells (PBMCs) prepared from normal human whole blood via density gradient centrifugation. Specific binding is defined as the total binding (e.g., total cpm on filters) minus the non-specific binding. Non-specific binding is defined as the amount of cpm still detected in the presence of excess unlabeled competitor (e.g., MCP-1).

CCR2 Binding $IC_{50}$

Human PBMCs were used to test compounds of the invention in a binding assay. For example, 200,000 to 500,000 cells were incubated with 0.1 to 0.2 nM 125I-labeled MCP-1, with or without unlabeled competitor (10 nM MCP-1) or various concentrations of compounds to be tested. 125I-labeled MCP-1, were prepared by suitable methods or purchased from commercial vendors (Perkin Elmer, Boston Mass.). The binding reactions were performed in 50 to 250 µL of a binding buffer consisting of 1M HEPES pH 7.2, and 0.1% BSA (bovine serum albumin), for 30 minutes at room temperature. The binding reactions were terminated by harvesting the membranes by rapid filtration through glass fiber filters (Perkin Elmer) which was presoaked in 0.3% polyethyleneimine or Phosphate Buffered Saline (PBS). The filters were rinsed with approximately 600 µL of binding buffer containing 0.5 M NaCl or PBS, then dried, and the amount of bound radioactivity was determined by counting on a Gamma Counter (Perkin Elmer).

More specifically, the following assay may be employed to determine $IC_{50}$ values for the compounds of the present invention.

hCCR2 (125-I hMCP-1) Small Molecule Binding Assay

The following reagents and supplies have been used in the preceding assay:

MCP-1
Biosource #PHC1013
1 mg
reconstitute with 2 ml binding buffer (0.5 mg per ml or 60 uM)
125I MCP-1
Perkin Elmer #NEX332
25 uCi
reconstitute with 0.2 ml PBS
RPMI 1640 with L-glutamine
MediaTech/Cellgro #10-040-CM
BSA
Sigma #A2153
HEPES
1 M solution
MediaTech/Cellgro #25-060-CL
NaCl
Sigma #S7653
Supplies
Muliscreen BV Filter Plates
Millipore #MABVN1250
Multiscreen Punch Tips
Millipore #MADP19650
Multiscreen Filtration System Vacuum Manifold
Millipore #MAVM0960R Normal human leukophoresis pack contents, available from Biological Specialty Corporation, Colmar, Pa., is diluted 1:1 with PBS, divided into 50 ml conical tubes (preferably less than 40 mls per tube), and underlayed with 10 mls of Ficoll-Paque PLUS (GE Healthcare 17-1440-02). The tubes are centrifuged at 2800 rpm in a clinical centrifuge at room temperature for 30 minutes, with no brake. The plasma layer is suctioned, and the buffycoat layer is collected. The collected buffycoat layer is washed twice with 50 mls PBS, and centrifuged at 1400 rpm with brake. The cells are counted. The cells are then diluted to $1 \times 10^7$ cells per ml in binding buffer.

96 well plates (such as, for example, Millipore Multi-Screen96 plates) are pre-wet with about 100 µl binding buffer (RPMI+0.1% BSA+20 mM HEPES), and blotted just prior to compound addition.

Plates with compound to be tested may be advantagously stored or managed with an automated system, such as, for example, TelCel (Hamilton Storage Technologies, Inc., 103 South Street, Hopkinton, Mass. 01748 USA)

5 µl of 50 µM test compounds in 100% DMSO are dotted onto U-bottom polypropylene 96-well plates.

245 µl per well of Binding Buffer is added to each well for 1 µM compound concentration in 2% DMSO.

50 µl of 1 µM compound is transferred to pre-wetted Millipore plates. 50 µl per well of 1×10E7 cells per ml of freshly prepared human PBMCs are added.

The samples are pre-incubated at room temperature for 30 minutes or 1 hour.

50 µl of 450 µM 125-I-hMCP-1 (Perkin-Elmer/NEN cat#NEX332025UC) is added for a final concentration 125-I-hMCP-1 of 150 pM per well.

The final test compound concentration is 0.333 uM in 150 µl total volume with 0.67% DMSO in all wells. Controls for this assay consist of 0% inhibition and 100% inhibition with 1 uM hMCP-1 (saturating conditions). All wells are run in duplicate. Controls may be in replicates of eight.

The samples are incubated at room temperature for 30 minutes.

The buffer is suctioned through the Millipore plates. The plates are washed three times with Wash Buffer (PRMI+0.1% BSA+20 mM HEPES+0.4 M NaC).

The plate underdrain is removed. The plate filters are allowed to dry. The filters are then punched out into plastic tubes.

Finally, the sample is counted on a Gamma Counter.

All IC50 plates were repeated for an n=2.

The following table summarizes the $IC_{50}$ values identified through the described assay.

TABLE 1

| Biological Data | | |
|---|---|---|
| Example | $IC_{50}$ (nM) 30 min preinc | $IC_{50}$ (nM) 1 hr preinc |
| 1 | 2.47 | |
| 2 | 3.16 | |
| 3 | 17.8 | |
| 4 | 3.98 | |
| 5 | 13.3 | |
| 6 | 1.73 | |
| 7 | 17.1 | |
| 8 | 10.7 | |
| 9 | 30.7 | |
| 10 | 83.8 | |
| 11 | 6.72 | 2.44 |
| 12 | 11.1 | 1.7 |
| 13 | 25.4 | 3.68 |
| 14 | 10.4 | 2.3 |
| 15 | 40 | 4.6 |
| 16 | 9.95 | 1.1 |
| 17 | 13.7 | 5.8 |
| 18 | 37.6 | 8.5 |
| 19 | 20.4 | 6.35 |
| 20 | 8.59 | |
| 21 | | 3.1 |
| 22 | | 1.1 |
| 23 | | 0.94 |
| 24 | 79.7 | 8.87 |
| 25 | 6.58 | 0.93 |
| 26 | 29.3 | 7.85 |
| 27 | 16.2 | 2.04 |
| 28 | | 1.88 |
| 29 | | 2.75 |
| 30 | 32.9 | 11.8 |
| 31 | | 6.35 |
| 32 | 13.8 | 11.7 |
| 33 | 57.3 | 11.7 |
| 34 | 66.5 | 6.94 |
| 35 | 28.4 | 5.52 |
| 36 | 12.6 | 2.19 |
| 37 | | 3.68 |
| 38 | 68.7 | 2.02 |
| 39 | 82.9 | 5.81 |
| 40 | 18.3 | |
| 41 | 63.6 | |
| 42 | 70.9 | |
| 43 | 47.3 | |
| 44 | | 8.1 |
| 45 | 25.3 | |
| 46 | 3.19 | |
| 47 | 6.16 | |
| 48 | 25.3 | |
| 49 | 35.8 | |
| 50 | 7.14 | |
| 51 | 22.8 | |
| 52 | 5.4 | |
| 53 | 27.6 | |
| 54 | 8.46 | |
| 55 | 28.3 | |
| 56 | 32.8 | |
| 57 | 4.34 | |
| 58 | 38.5 | |
| 59 | 17.7 | |
| 60 | 2.4 | |
| 61 | 5.9 | |
| 62 | 1.3 | |
| 63 | | 1.1 |
| 64 | | 4.7 |
| 65 | | 1.5% @300 nM |
| 66 | 1.7 | |
| 67 | 3.4 | |
| 68 | 5.4 | |
| 69 | 4.3 | |
| 70 | 8.7 | |
| 71 | 3.7 | |

Diabetic Nephropathy Rat Model

A rat model of diabetic nephropathy was used to determine the renal protective effect of pharmacological inhibition of CCR2. The streptozotocin (STZ)-induced diabetic rat model has been extensively used for studying the progression of diabetic renal disease. STZ injection causes immediate destruction of pancreatic β-cells, consequently hyperglycemia and progression of nephropathy similar to that seen in human diabetes mellitus. Diabetes was induced in male Wistar rats by single administration of STZ (45 mg/kg, iv). Three days after the induction of diabetes, fasting blood glucose levels were assessed. Animals with fasting blood glucose levels higher than 200 mg/dL were included in the study. All the treatments were then initiated. 1,5-anhydro-2,3-dideoxy-3-{[(1R,3S)-3-isopropyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol was administered at doses of 0.03, 0.3, 1, and 10 mg/kg (mpk) (in the chow) for 11 weeks. 24-hour urine collections were obtained at 1, 4, 8, and 11 weeks, after the treatment for assessing 24-hour urinary albumin excretion (UAE). As expected, following the induction of diabetes there was a persistent elevation in UAE over the 11 week course of this study. 1,5-anhydro-2,3-dideoxy-3-{[(1R,3S)-3-isopropyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol treatment significantly reduced UAE at doses of 0.3 mpk (1.73±0.69 mg/24 h), 1 mpk (1.09±0.20 mg/24 h), and 10 mpk (0.71±0.22 mg/24 h) compared to untreated STZ rats (4.32±1.34 mg/24 h) at week 8, and at all doses (2.17±1.31, 1.96±0.85, 1.66±0.65, and 1.02±0.32 mg/24 h, at 0.03, 0.3, 1, and 10 mpk dose, respectively, vs. 6.36±2.08 mg/24 h, untreated STZ rats) at week 11. These data demonstrate that pharmacological inhibition of CCR2 provides renal protection during the development and progression of diabetic nephropathy and support CCR2 antagonism as a new therapeutic strategy to treat diabetic renal disease.

What is claimed is:

1. 1,5-anhydro-2,3-dideoxy-3-{[(1R,3S)-3-isopropyl-3-({(1S,4S)-5-[6-(trifluoromethyl)pyrimidin-4-yl]-2,5-diazabicyclo[2.2.1]hept-2-yl}carbonyl)cyclopentyl]amino}-4-O-methyl-D-erythro-pentitol.

2. A compound of formula:

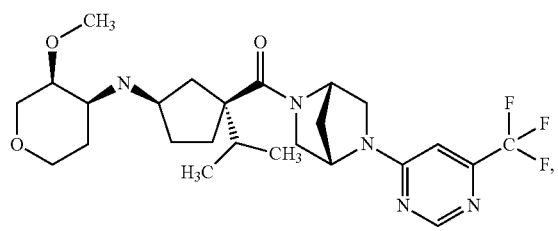

or a pharmaceutically acceptable salt thereof.

3. A pharmaceutical composition comprising a compound of claim 2, or a pharmaceutically acceptable salt thereof, and a carrier.

4. A method of treating a disease associated with expression or activity of a chemokine receptor in a patient comprising administering to said patient a compound of claim 2, or a pharmaceutically acceptable salt thereof, wherein the disease is diabetic nephropathy.

* * * * *